(12) United States Patent
Floeder et al.

(10) Patent No.: US 7,542,821 B2
(45) Date of Patent: Jun. 2, 2009

(54) MULTI-UNIT PROCESS SPATIAL SYNCHRONIZATION OF IMAGE INSPECTION SYSTEMS

(75) Inventors: Steven P. Floeder, Shoreview, MN (US); Kenneth G. Brittain, Cottage Grove, MN (US); James A. Masterman, Lake Elmo, MN (US); Carl J. Skeps, Lakeville, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 194 days.

(21) Appl. No.: 11/828,383

(22) Filed: Jul. 26, 2007

(65) Prior Publication Data

US 2009/0030544 A1    Jan. 29, 2009

(51) Int. Cl.
*G06F 19/00* (2006.01)
*G01B 5/28* (2006.01)
*G01B 5/30* (2006.01)
*G01N 21/84* (2006.01)
*G06K 9/00* (2006.01)

(52) U.S. Cl. .................. 700/124; 700/108; 700/109; 700/110; 700/122; 700/125; 702/35; 702/36; 702/182; 702/185; 250/559.44; 250/559.46; 356/429; 356/430; 356/435; 382/141; 382/143; 382/149

(58) Field of Classification Search ......... 700/108–110, 700/122, 124–125; 702/35–36, 182, 185; 250/559.44, 559.46; 356/429–430, 435; 382/141, 143, 149
See application file for complete search history.

(56) References Cited

U.S. PATENT DOCUMENTS

| 3,759,620 A | 9/1973 | Cushing et al. |
| 4,134,684 A | 1/1979 | Jette |
| 4,173,441 A | 11/1979 | Wolf |
| 4,211,132 A | 7/1980 | Nichols, III et al. |

(Continued)

FOREIGN PATENT DOCUMENTS

EP    0 681 183 A2    11/1995

(Continued)

OTHER PUBLICATIONS

Internatioanl Preliminary Examination Report, PCT/US2005/009741, Mar. 23, 2005, (19 pages).

(Continued)

*Primary Examiner*—Ramesh B Patel
(74) *Attorney, Agent, or Firm*—Steven A. Bern

(57) ABSTRACT

A conversion control system is described that includes a database to store data defining a set of rules and an interface to receive local anomaly information from a plurality of different analysis machines associated with a plurality of manufacturing process lines that perform a plurality of operations on a web of material, and each of the manufacturing process lines includes position data for a set of regions on the web containing anomalies. The system also includes a computer that registers the position data of the local anomaly information for the plurality of manufacturing process lines to produce aggregate anomaly information. The system further includes a conversion control engine that applies the rules to the aggregate anomaly information to determine which anomalies represent actual defects in the web for a plurality of different products.

46 Claims, 25 Drawing Sheets

U.S. PATENT DOCUMENTS

| | | | |
|---|---|---|---|
| 4,330,356 A | 5/1982 | Grollimund et al. | |
| 4,458,852 A | 7/1984 | Calvert et al. | |
| 4,567,064 A | 1/1986 | Wöste | |
| 4,629,312 A | 12/1986 | Pearce et al. | |
| 4,700,627 A | 10/1987 | Hagler | |
| 4,746,020 A | 5/1988 | Schenk | |
| 4,752,897 A | 6/1988 | Zoeller et al. | |
| 4,776,023 A | 10/1988 | Hamada et al. | |
| 4,828,156 A | 5/1989 | Whiteley et al. | |
| 4,877,323 A | 10/1989 | Stillwagon | |
| 4,905,159 A | 2/1990 | Loriot | |
| 4,927,180 A | 5/1990 | Trundle et al. | |
| 4,951,223 A | 8/1990 | Wales et al. | |
| 4,972,326 A | 11/1990 | Jung et al. | |
| 4,982,600 A | 1/1991 | Kiso et al. | |
| 5,062,331 A | 11/1991 | Michal et al. | |
| 5,068,799 A * | 11/1991 | Jarrett, Jr. | 702/40 |
| 5,301,129 A | 4/1994 | McKaughan et al. | |
| 5,305,392 A | 4/1994 | Longest, Jr. et al. | |
| 5,351,202 A * | 9/1994 | Kurtzberg et al. | 702/81 |
| 5,365,596 A | 11/1994 | Dante et al. | |
| 5,403,722 A | 4/1995 | Floeder et al. | |
| 5,415,123 A | 5/1995 | Ryder | |
| 5,434,629 A | 7/1995 | Pearson et al. | |
| 5,440,648 A | 8/1995 | Roberts et al. | |
| 5,450,116 A | 9/1995 | Weiselfish et al. | |
| 5,544,256 A | 8/1996 | Brecher et al. | |
| 5,696,591 A | 12/1997 | Bilhorn et al. | |
| 5,710,420 A | 1/1998 | Martin et al. | |
| 5,760,414 A | 6/1998 | Taylor | |
| 5,774,177 A | 6/1998 | Lane | |
| 5,873,392 A | 2/1999 | Meyer et al. | |
| 5,949,550 A | 9/1999 | Arndt et al. | |
| 6,014,209 A | 1/2000 | Bishop | |
| 6,031,931 A | 2/2000 | Chiu et al. | |
| 6,092,059 A | 7/2000 | Straforini et al. | |
| 6,100,989 A | 8/2000 | Leuenberger | |
| 6,137,967 A | 10/2000 | Laussermair et al. | |
| 6,252,237 B1 | 6/2001 | Ramthun et al. | |
| 6,266,436 B1 | 7/2001 | Bett et al. | |
| 6,266,437 B1 * | 7/2001 | Eichel et al. | 382/149 |
| 6,272,437 B1 | 8/2001 | Woods et al. | |
| 6,295,129 B1 | 9/2001 | Björk | |
| 6,314,379 B1 | 11/2001 | Hu et al. | |
| 6,330,350 B1 | 12/2001 | Ahn et al. | |
| 6,404,910 B1 | 6/2002 | Ungpiyakul et al. | |
| 6,407,373 B1 | 6/2002 | Dotan | |
| 6,452,679 B1 * | 9/2002 | Workman, Jr. | 356/429 |
| 6,484,306 B1 | 11/2002 | Bokor et al. | |
| 6,496,596 B1 | 12/2002 | Zika et al. | |
| 6,661,507 B2 | 12/2003 | Yoda et al. | |
| 6,665,432 B1 | 12/2003 | Evans et al. | |
| 6,750,466 B2 * | 6/2004 | Guha et al. | 250/559.46 |
| 6,765,224 B1 * | 7/2004 | Favreau et al. | 250/559.4 |
| 6,778,694 B1 | 8/2004 | Alexandre | |
| 6,798,925 B1 | 9/2004 | Wagman | |
| 6,804,381 B2 * | 10/2004 | Pang et al. | 382/111 |
| 6,812,997 B2 * | 11/2004 | Kaltenbach et al. | 355/40 |
| 6,814,514 B2 | 11/2004 | Korngold et al. | |
| 6,845,278 B2 | 1/2005 | Popp et al. | |
| 6,934,028 B2 | 8/2005 | Ho et al. | |
| 6,950,547 B2 | 9/2005 | Floeder et al. | |
| 7,027,934 B2 | 4/2006 | Skeps et al. | |
| 7,117,057 B1 * | 10/2006 | Kuo et al. | 700/108 |
| 7,120,515 B2 | 10/2006 | Floeder et al. | |
| 7,187,995 B2 | 3/2007 | Floeder et al. | |
| 2002/0020704 A1 | 2/2002 | Zacharias | |
| 2002/0030704 A1 | 3/2002 | Korngold et al. | |
| 2002/0039436 A1 | 4/2002 | Alumot et al. | |
| 2002/0080347 A1 | 6/2002 | Yoda et al. | |
| 2002/0109112 A1 | 8/2002 | Guha et al. | |
| 2002/0110269 A1 | 8/2002 | Floeder et al. | |
| 2002/0176617 A1 | 11/2002 | Simonetti | |
| 2003/0189704 A1 | 10/2003 | Floeder et al. | |
| 2004/0030435 A1 | 2/2004 | Popp et al. | |
| 2004/0058540 A1 * | 3/2004 | Matsumoto et al. | 438/689 |
| 2005/0075801 A1 | 4/2005 | Skeps et al. | |
| 2005/0141760 A1 | 6/2005 | Floeder et al. | |
| 2005/0144094 A1 | 6/2005 | Floeder et al. | |
| 2005/0154485 A1 * | 7/2005 | Popp et al. | 700/124 |
| 2005/0232475 A1 | 10/2005 | Floeder et al. | |
| 2006/0164645 A1 * | 7/2006 | Hietanen et al. | 356/430 |
| 2009/0028416 A1 | 1/2009 | Floeder et al. | |
| 2009/0028417 A1 | 1/2009 | Floeder et al. | |

FOREIGN PATENT DOCUMENTS

| | | |
|---|---|---|
| EP | 0 898 163 A1 | 8/1997 |
| EP | 1 022 906 A1 | 1/2000 |
| EP | 1 348 946 A1 | 10/2003 |
| JP | 62/093637 | 4/1987 |
| JP | 11/248641 | 9/1999 |
| JP | 2000/009447 | 1/2000 |
| JP | 2001/261191 | 9/2001 |
| JP | 2002/243648 | 8/2002 |
| WO | WO 95/14805 | 6/1995 |
| WO | WO 98/44336 | 10/1998 |
| WO | WO 99/10833 | 3/1999 |
| WO | WO 00/07031 | 2/2000 |
| WO | WO 01/02840 A1 | 1/2001 |
| WO | WO 01/53811 A1 | 7/2001 |
| WO | WO 02/21105 A1 | 3/2002 |
| WO | WO 02/065106 A1 | 8/2002 |
| WO | WO 02/065107 A2 | 8/2002 |
| WO | WO 03/081219 A1 | 10/2003 |
| WO | WO 2005/065367 A2 | 7/2005 |
| WO | WO 2005/106104 A1 | 11/2005 |
| WO | WO 2006/066398 A1 | 9/2006 |
| WO | WO 2007/026174 A2 | 3/2007 |

OTHER PUBLICATIONS

"A PC-Based Real Time Defect Imaging System for High Speed Web Inspection", by J.W. Roberts, S.D.Rose, G.Julien, L.Nichols, G.Moroscher, P.T.Jenkins, S.G.Chamberlain, R.Mantha, and D.J. Litwiller, DALSA Inc., pp. 7-29-7-41.

"Real-Time Computer Vision on PC-Cluster and Its Application to Real-Time Motion Capture", by Daisaku Arita, Satoshi Yonemoto, and Rin-ichiro Taniguchi, Kyushu University, Japan, 2000, pp. 205-206.

Technical Paper "The Application of a Flexible Machine Vision Architecture to the Inspection of Continuous Process Materials", by Brad Harkavy, from VISION '89 Conference, Chicago, Illinois, MS89-165, attended on Apr. 24-27, 1989.

"Flexible Circuits, Roll-to-Roll AOI" by Brian Tithecott, PC FAB, pp. 26-28, 30, and 32.

"A New Design Environment for Defect Detection in Web Inspection Systems," by S. Hossain Hajimowlana, Roberto Muscedere, Graham A. Jullien, James W. Roberts, DALSA Inc., SPIE vol. 3205, 1997, pp. 125-136.

"Parsytec HTS-2, Defect Detection and Classification Through Software vs. Dedicated Hardware", by Reinhard Rinn, Scott A. Thompson, Dr. Ralph Foehr, Friedrich Luecking, and John Toree; SPIE vol. 3645; Jan. 1999, pp. 110-121.

Wenyuan Xu et al., "Industrial Web Inspection for Manufacturing Process Understanding and Control", Proceedings of the SPIE—The International Society for Optical Engineering SPIE-INT. Soc. Opt. Eng USA, vol. 3652, Jan. 1, 1999, pp. 10-20, XP002307220, ISSN: 0277-786X, Figure 1.

Floeder et al., "Multi-Roller Registered Repeat Defect Detection of a Web Process Line", U.S. Appl. No. 12/207,582, filed Sep. 10, 2008.

* cited by examiner

MULTI-UNIT PROCESS SPATIAL SYNCHRONIZATION OF IMAGE INSPECTION SYSTEMS

TECHNICAL FIELD

The present invention relates to automated inspection of systems, and more particularly, to inspection of continuously moving webs.

BACKGROUND

Inspection systems for the analysis of moving web materials have proven critical to modern manufacturing operations. Industries as varied as metal fabrication, paper, nonwovens, and films rely on these inspection systems for both product certification and online process monitoring. One major difficulty in the industry is related to the extremely high data processing rates required to keep up with current manufacturing processes. With webs of commercially viable width and web speeds that are typically used and pixel resolution that is typically needed, data acquisition speeds of tens or even hundreds of megabytes per second are required of the inspection systems. It is a continual challenge to process images and perform accurate defect detection at these data rates.

In addition, web process manufacturing operations are becoming more complicated with multiple unit operations being performed on a single roll of material during its production. For example, certain complex web-based products, such as flexible circuits, may require as many as fifteen distinct manufacturing operations over the course of days or even weeks, often utilizing multiple production lines at different physical sites. In these circumstances, it is typical to collect the web into a roll after each process and ship the roll to a different location where it is then unrolled, processed, and again collected into a roll. Each process may introduce new anomalies into a web which may or may not cause the web to be defective. Moreover, subsequent processes may make detection of earlier anomalies difficult, if not impossible.

SUMMARY

In general, techniques are described for the automated inspection of moving webs. More specifically, the techniques described herein are directed to performing spatial registration and combination of anomaly data collected throughout the production of a web. That is, the techniques provide for the spatial registration and combination of anomaly data collected throughout multiple unit operations being performed on a roll of material during its production, even though production may require use of multiple production lines over an extended period of time at different physical sites.

For example, during each manufacturing process for the web, one or more inspection systems acquire anomaly information for the web. The inspection systems may analyze this so called "local" anomaly information and perform a preliminary examination. Image information about any regions of the web containing anomalies is stored for subsequent processing. Similar techniques are applied at each process within the multi-process production of the web, thereby generating local anomaly information for each of the manufacturing processes, i.e., stages.

The anomaly information generated during the various production processes for the moving web may be communicated to a system, where the anomaly information from the different processes for the web can be spatially registered. That is, the respective anomaly information from the different processes can be aligned such that the anomalies from the different manufacturing processes have spatial relevance with each other to produce "aggregate" anomaly information for the web.

The local anomaly data produced by each manufacturing process for a web can be stored and reconciled with newly acquired anomaly data such that the positions of all anomalies detected at all stages of web processing can be analyzed at a later time. Once aggregated, more sophisticated algorithms can be applied to the aggregate anomaly information to determine any actual defects based on a variety of factors. For example, a conversion control system may subsequently apply one or more defect detection algorithms to the aggregate anomaly data to ultimately generate a conversion plan for a web roll. That is, the conversion control system may select a conversion plan having defined instructions for processing the web roll. The defect detection algorithms applied by the conversion control system may be application-specific, i.e., specific to different potential products, to provide for increased or optimal utilization of the web roll based on the aggregate anomaly data. The conversion control system may communicate this aggregate anomaly information and the conversion plan to one or more conversion sites for producing products from the web.

The use of spatially registered anomaly information that spans multiple manufacturing processes for a single web may provide many advantages, such as significantly enhanced process quality analysis and control, defective product containment, increased utilization of the web, reduced cost, increase revenue or profit and a variety of other potential benefits.

For example, it may be possible to maintain registration of defect position within 0-2 mm throughout the entire production process. As another example, it may be possible to identify waste-by-cause for each sub-process. Furthermore, the gathered data may prove useful in optimizing parts combined from different operations. It may also be possible to automatically reject defective parts even if the defect is undetectable in the final product.

In one embodiment, the invention is directed to a method comprising performing a plurality of operations on a web at a plurality of manufacturing process lines, imaging a sequential portion of the web to provide digital information at each of the manufacturing process lines, processing the digital information to produce local anomaly information for each of the manufacturing process lines, wherein the local anomaly information for each of the manufacturing process lines includes position data for a set of regions on the web containing anomalies, registering the position data of the local anomaly information for the plurality of manufacturing process lines to produce aggregate anomaly information, analyzing at least a portion of the aggregate anomaly information to determine which of the anomalies represent actual defects in the web, and outputting a conversion control plan.

In another embodiment, the invention is directed to a system including a plurality of manufacturing process lines that perform a plurality of operations on a web. The system also includes a plurality of imaging devices positioned within a plurality of manufacturing process lines, wherein each of the imaging devices sequentially images at least a portion of the web to provide digital information. The system further includes one or more analysis computers to process the digital information to produce local anomaly information for each of the manufacturing process lines, wherein the local anomaly information for each of the manufacturing process lines includes position data for a set of regions on the web containing anomalies. Moreover, the system includes a computer that registers the position data of the local anomaly information for the plurality of manufacturing process lines to produce aggregate anomaly information. The system also includes a conversion control system that analyzes at least a portion of the aggregate anomaly information to determine which anomalies represent actual defects in the web for a plurality of different products.

In another embodiment, the invention is directed to a conversion control system comprising a database storing data defining a set of rules and an interface to receive local anomaly information from a plurality of different analysis machines associated with a plurality of manufacturing process lines that perform a plurality of operations on a web of material, wherein each of the manufacturing process lines includes position data for a set of regions on the web containing anomalies. The conversion control system also includes a computer that registers the position data of the local anomaly information for the plurality of manufacturing process lines to produce aggregate anomaly information. The conversion control system further includes a conversion control engine that applies the rules to the aggregate anomaly information to determine which anomalies represent actual defects in the web for a plurality of different products.

In another embodiment, a method comprises performing a plurality of operations on a web at a plurality of manufacturing process lines, generating digital information at each of the manufacturing process lines, processing the digital information to produce local anomaly information for each of the manufacturing process lines, wherein the local anomaly information for each of the manufacturing process lines includes position data for a set of regions on the web containing anomalies, registering the position data of the local anomaly information for the plurality of manufacturing process lines to produce aggregate anomaly information, analyzing at least a portion of the aggregate anomaly information to determine which of the anomalies represent actual defects in the web, and outputting a conversion control plan.

In another embodiment, a method comprises performing a plurality of operations on a web at a plurality of manufacturing process lines, imaging a sequential portion of the web to provide digital information at each of the manufacturing process lines, processing the digital information to produce local anomaly information for each of the manufacturing process lines, wherein the local anomaly information for each of the manufacturing process lines includes position data for a set of regions on the web containing anomalies, registering the position data of the local anomaly information for the plurality of manufacturing process lines to produce aggregate anomaly information, analyzing at least a portion of the aggregate anomaly information to determine which of the anomalies represent defects in the web, and outputting a conversion control plan.

Although discussed primarily with respect to gathering anomaly information, the techniques described herein are not limited to gathering only anomaly information from which defect information may be generated. For example, in another embodiment, determination of actual defect may be performed without first identifying anomalies (i.e., potential defects), for subsequent analysis. As an example, a method comprises performing a plurality of operations on a web at a plurality of manufacturing process lines, imaging a sequential portion of the web to provide digital information at each of the manufacturing process lines, processing the digital information to produce local defect information for each of the manufacturing process lines, wherein the local defect information for each of the manufacturing process lines includes position data for a set of regions on the web containing defects, registering the position data of the local defect information for the plurality of manufacturing process lines to produce aggregate defect information, and outputting a conversion control plan.

The details of one or more embodiments of the invention are set forth in the accompanying drawings and the description below. Other features, objects, and advantages of the invention will be apparent from the description and drawings, and from the claims.

DEFINITIONS

For purposes of the present invention, the following terms used in this application are defined as follows:

"web" means a sheet of material having a fixed dimension in one direction and either a predetermined or indeterminate length in the orthogonal direction;

"sequential" means that an image is formed by a succession of single lines, or areas of the web that optically map to a single row of sensor elements (pixels);

"pixel" means a picture element represented by one or more digital values;

"defect" means an undesirable occurrence in a product;

"anomaly" or "anomalies" mean a deviation from normal product that may or may not be a defect, depending on its characteristics and severity.

"filter" is a mathematical transformation of an input image to a desired output image, filters are typically used to enhance contrast of a desired property within an image;

"application-specific" means defining requirements, e.g., grade levels, based on the intended use for the web;

"yield" represents a utilization of a web expressed in percentage of material, unit number of products or some other manner;

"products" are the individual sheets (also referred to as component) produced from a web, e.g., a rectangular sheet of film for a cell phone display or a television screen; and "conversion" is the process of physically cutting a web into products.

DETAILED DESCRIPTION

Figure 1:
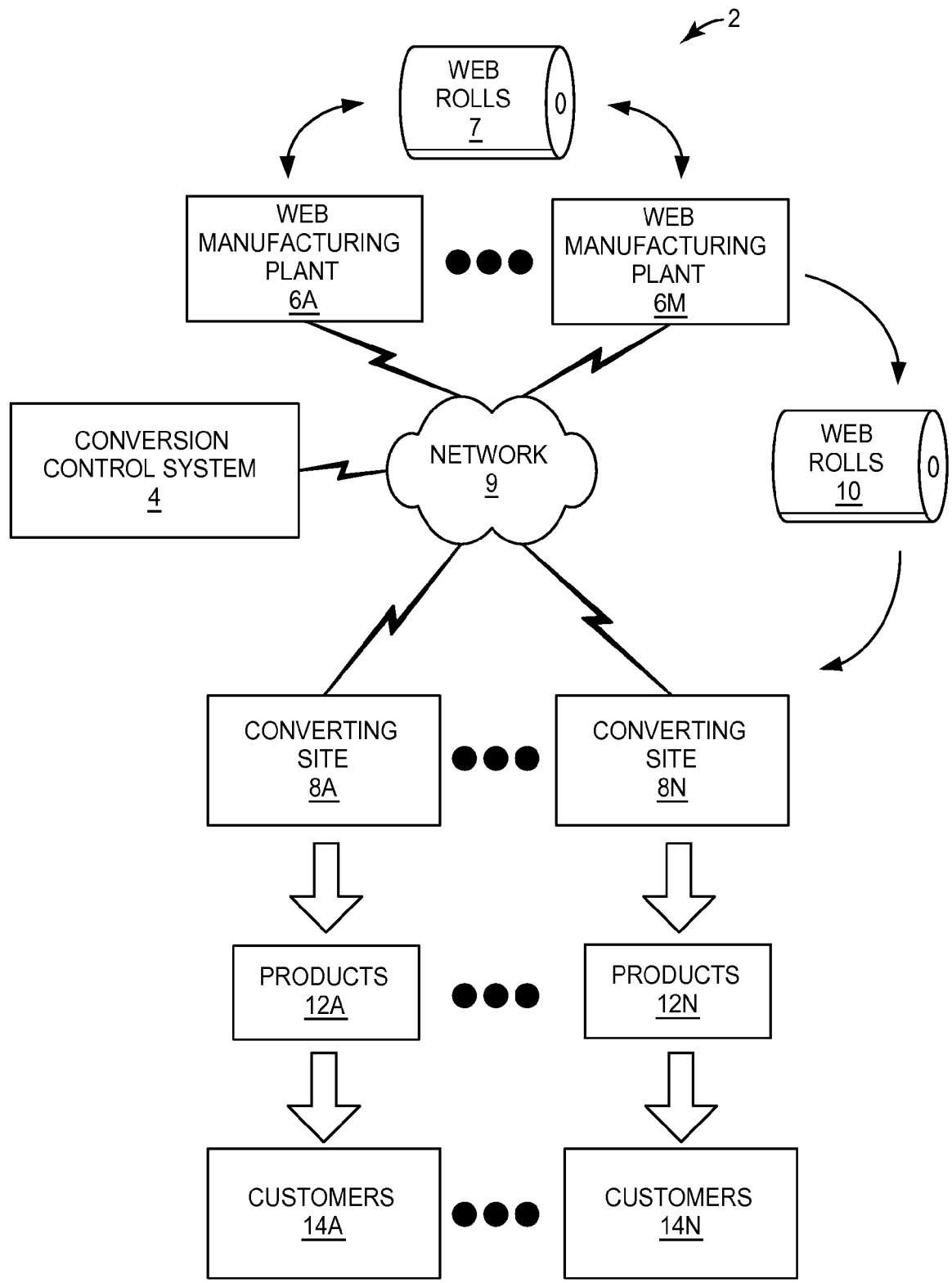
FIG. 1 is a block diagram illustrating a global network environment in which a conversion control system controls conversion of web material.
Figure 3:
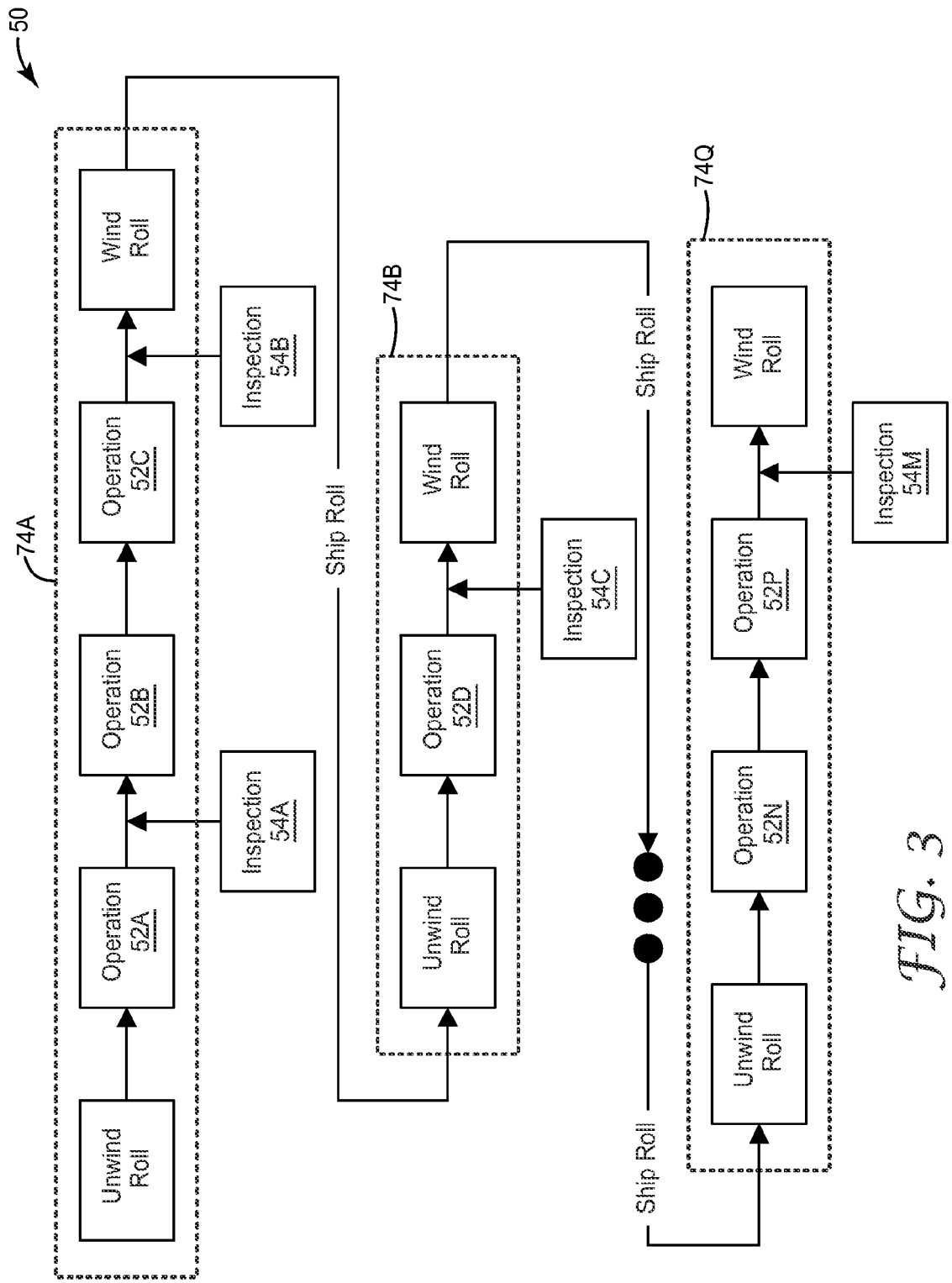
FIG. 3 is a block diagram illustrating an exemplary sequence of procedures and inspections for a web.

FIG. 1 is a block diagram illustrating a global network environment 2 in which conversion control system 4 controls conversion of web material. More specifically, web manufacturing plants 6A-6N ("web manufacturing plants 6") represent manufacturing sites that produce and ship web material in the form of web rolls 7 between each other and ship finished web rolls 10 to converting sites 8A-8N. Web manufacturing plants 6 may be geographically distributed, and each of the web manufacturing plants may include one or more manufacturing process lines (FIG. 3).

In general, web rolls 7 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

In order to manufacture a finished web roll 10 which is ready for conversion into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced.

For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof. A given coating may be applied to only a portion of the web material or may fully cover the exposed surface of the web material. Further, the web materials may be patterned or unpatterned.

Figure 2:
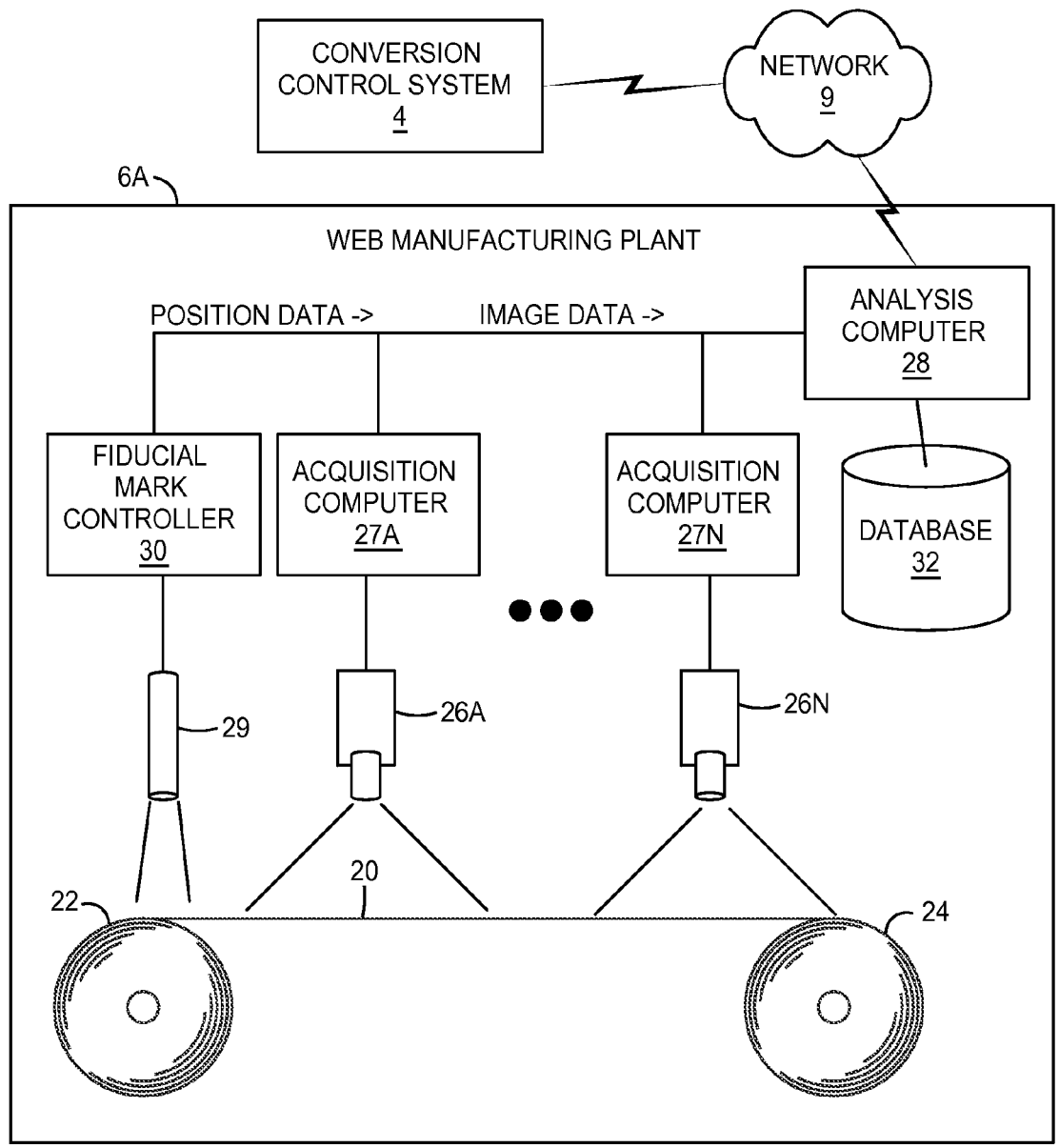
FIG. 2 is a block diagram illustrating an exemplary embodiment of a web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital image data. The inspection systems may analyze the image data with one or more algorithms to produce so called "local" anomaly information. The anomaly information may be referred to herein as local anomaly information in that the anomaly information generally includes position information that is specific to a coordinate system local to, or generally used by, the production line currently in use. As described below, this local position information may be meaningless to other manufacturing plants or even other production lines within the same manufacturing plant. For these reasons, the local anomaly information obtained during the production for each of web rolls 7 is spatially registered with other local anomaly information for the same web roll. That is, the position information associated with the local anomaly is translated to a common coordinate system to align position information from different manufacturing processes applied to the same web roll 7 or a segment of web roll 7. The anomaly information is referred to herein as aggregate anomaly information once collected and aligned with anomaly information for at least one or possibly all of the manufacturing processes for the same web roll 7.

More specifically, during each manufacturing process, the image information (i.e., raw pixel information) for any regions of the web containing anomalies is stored for subsequent processing. That is, the raw image data surrounding an identified anomaly is extracted from the stream of pixel information obtained from the image acquisition device and stored along with position information indicating the specific location of the anomaly within the web, both with respect to the dimension across the web and the dimension running the length of the web. Image data not associated with anomalies is discarded. Similar techniques are applied at each process within the multi-process production of a given web roll 7, thereby generating local anomaly information for each of the manufacturing processes, i.e., stages.

The local anomaly information generated during the various production processes for the moving web is then communicated to conversion control system 4, where the local anomaly information from the different processes for the web can be spatially registered. That is, the respective anomaly information from the different processes can be aligned such that the anomalies from the different manufacturing processes have spatial relevance with each other to produce the aggregate anomaly information for a given web roll 7. Spatial registration may occur at any time during the overall manufacturing process, e.g., between each stage of the multi-process production for a web roll or after completion of all the processes. Moreover, spatial registration may be performed centrally, such as within conversion control system 4, or locally at a given web manufacturing plant 6 using the local anomaly information obtained from the production lines previously used for the given web roll 7.

In general, conversion control system 4 applies one or more defect detection algorithms that may be application-specific, i.e., specific to products 12, to select and generate a conversion plan for each web roll 10. A certain anomaly may result in a defect in one product, for instance product 12A, whereas the anomaly is not a defect in a different product, for instance, product 12B. Each conversion plan represents defined instructions for processing a corresponding finished web roll 10. Conversion control system 4 communicates the conversion plans for web rolls 10 via network 9 to the appropriate converting sites 8 for use in converting the web rolls into products 12.

In order to properly create a conversion plan for converting a finished web roll 10 which has undergone multiple manufacturing processes, the data collected by web manufacturing plants 6 is spatially reconciled and analyzed to form a composite defect map. As noted above, collected anomaly data generally includes small regions of raw image data along with position information representing the locations of anomalies on a web roll. Spatial reconciliation of anomaly data can either be done at a central location, such as conversion control system 4, once all processes have finished or at various intermediate process locations. Moreover, a predefined, spatial coordinate system may be used for registration of the data. In this case, all of the position data associated with the local anomaly information is translated to this predefined coordinate system. As an alternative, a coordinate system used within a first process (or any other process) applied to a given web roll 7 can act as a reference coordinate system to which all local anomaly data is registered for subsequent processes applied to the same web roll.

For example, an inspection system for a first manufacturing process applied to a given web roll 7 can submit its local anomaly information to conversion control system 4 once the first process has finished. This may include coordinate system reference data describing a coordinate system utilized by the inspection system while collecting the initial local anomaly information. Then, inspection systems or other computing devices associated with each subsequent manufacturing process applied to that same web roll 7 may retrieve the coordinate system reference data used by the first process from conversion control system 4 and adjust the position data for any newly gathered local anomaly information according to the coordinate system used during the first manufacturing process. As mentioned, alternatively, conversion control system 4 may process local anomaly information from each of the manufacturing processes. In this manner, all of the position data of the local anomaly information gathered from all manufacturing processes for the same web roll 7 can be reconciled so that all anomalous regions in web roll 10 are known regardless of when, that is, from which process, each anomaly was introduced.

Conversion control system 4 applies one or more defect detection algorithms to the aggregate anomaly information to ultimately select and generate a conversion plan for each web roll 10. Conversion control system 4 may select converting sites 8 based on one or more parameters, and ultimately may direct the conversion of web rolls 10 into products 12. That is, conversion control system 4 selects, in an automated or semi-automated manner, converting sites 8 for converting web rolls 10 based on one or more site selection parameters, such as current product inventory levels at the various converting sites. Conversion control system 4 may utilize other site selection parameters, such as order information associated with each of products 12 at the various converting sites 8, current product demand experienced within the geographic regions serviced by the converting sites, shipping costs and transportation options associated with each of the converting sites, and any time-critical orders pending at the converting sites.

Based on the selections made by conversion control system 4, web rolls 10 are shipped to converting sites 8A-8N ("converting sites 8"), which may be geographically distributed within different countries. Converting sites 8 convert each web roll 10 into one or more products. Specifically, each of converting sites 8 includes one or more process lines that physically cut the web for a given web roll 10 into numerous individual sheets, individual parts, or numerous web rolls, referred to as products 12A-12N ("products 12"). As one example, converting site 8A may convert web rolls 10 of film into individual sheets for use in automobile lighting systems. Similarly, other forms of web materials may be converted into products 12 of different shapes and sizes depending upon the intended application by customers 14A-14N ("customers 14"). Each of converting sites 8 may be capable of receiving different types of web rolls 10, and each converting site may produce different products 12 depending on the location of the converting site and the particular needs of customers 14.

The use of spatially registered anomaly information that spans multiple manufacturing processes for a single web may provide many advantages, such as significantly enhanced process quality analysis and control, defective product containment, increased utilization of the web, reduced cost, increase revenue or profit and a variety of other potential benefits. For example, it may be possible to maintain registration of defect position within 0-5 mm or preferably within 0-2 mm throughout the entire production process. As another example, it may be possible to identify waste-by-cause for each sub-process. Furthermore, the gathered data may prove useful in optimizing parts combined from different operations. It may also be possible to automatically reject defective parts even if the defect is undetectable in the final product.

FIG. 2 is a block diagram illustrating an exemplary embodiment of one process line in an exemplary embodiment of web manufacturing plant 6A of FIG. 1. In the exemplary embodiment, a segment of a web 20 is positioned between two support rolls 22, 24. Image acquisition devices 26A-26N ("image acquisition devices 26") are positioned in close proximity to the continuously moving web 20. Image acquisition devices 26 scan sequential portions of the continuously moving web 20 to obtain image data. Acquisition computers 27 collect image data from image acquisition devices 26, and transmit the image data to analysis computer 28 for preliminary analysis.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Model#LD21 from Perkin Elmer (Sunnyvale, Calif.), Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

Fiducial mark controller 30 controls fiducial mark reader 29 to collect roll and position information from web 20. For example, fiducial mark controller may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. For example, fiducial mark controller 30 may produce position information locating each detected fiducial mark within a coordinate system applied to the process line. Alternatively, analysis computer 28 may place each of the detected fiducial marks within the coordinate system based on the position data received from fiducial mark controller 30. In this case, the position data provided by fiducial mark controller 30 may represent distances between each fiducial mark in a dimension along the length of web 20. In either case, fiducial mark controller 30 communicates the roll and position information to analysis computer 28.

Analysis computer 28 processes image streams from acquisition computers 27. Analysis computer 28 processes the digital information with one or more initial algorithms to generate local anomaly information that identifies any regions of web 20 containing anomalies that may ultimately qualify as defects. For each identified anomaly, analysis computer 28 extracts from the image data an anomaly image that contains pixel data encompassing the anomaly and possibly a surrounding portion of web 20. Analysis computer 28 may classify an anomaly into different defect classes if necessary. For instance, there may be unique defect classes to distinguish between spots, scratches, and oil drips. Other classes may distinguish between further types of defects.

Based the position data produced by fiducial mark controller 30, analysis computer 28 determines the spatial position of each anomaly within the coordinate system of the process line. That is, based on the position data from fiducial mark controller 30, analysis computer 28 determines the x-y and possibly z position for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20. The coordinate system defined for the current process line may not be (and is typically not) the same coordinate system for any previous or subsequent processes applied to web 20.

In any case, analysis computer 28 records in database 32 the spatial location of each anomaly with respect to the coordinate system of the process line, this information being referred to herein as local anomaly information. That is, analysis computer 28 stores the local anomaly information for web 20, including roll information for the web 20 and position information for each anomaly, within database 32. As described below, the local anomaly information generated for the current process line is subsequently spatially registered with local anomaly information generated by the other process lines for the same web. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Once the process has ended, analysis computer 28 will transmit the data collected in database 32 to conversion control system 4 via network 9. Specifically, analysis computer 28 communicates the roll information as well as the local anomaly information and respective sub-images to conversion control system 4 for subsequent, offline, detailed analysis. For example, the information may be communicated by way of a database synchronization between database 32 and conversion control system 4.

Spatial registration of anomaly data can be performed subsequently at conversion control system 4, either after one or more processes or once all processes have finished. Alternatively, analysis computer 28 may perform the spatial registration. For example, in such an embodiment, conversion control system 4 may communicate through network 9 with analysis computer 28 to inform analysis computer 28 of a coordinate system that is to be used for reconciled anomaly data. In this case, analysis computer 28 may spatially register position local anomaly data for web 20, which is typically based on a coordinate system of the current process line, with the representative coordinate system specified by conversion control system. Conversion control system 4 may select the representative coordinate system that is to be used for spatial registration based on a coordinate system associated with the first manufacturing process line applied to web 20. Alternatively, coordinate system of any other process line used or scheduled to be used for web 20 may be selected. Moreover, conversion control system 4 may define a coordinate system different from any of the coordinate systems associated with the product lines.

As an example, a first manufacturing process may have recorded fiducial mark "38" at a position of 76.027 meters (m) along the length of web 20. The current process, however, may record fiducial mark "38" at 76.038 m, an offset of 0.011 m. Analysis computer 28 (or optionally conversion control system 4 or some other centralized computing device) may adjust measurements of position data for the current process to align the position data with position data from the first process. That is, from the example above, analysis computer 28 may translate the position data for the detected fiducial mark "38" to match the position 76.027 m within the first process. Likewise, if analysis computer 28 detects an anomaly at position 76.592 m, analysis computer 28 applied a similar degree of translation to record this anomaly as being present at position 76.581 m. This translation may, for example, be effected by adjusting the position of the anomaly as measured by the current process according to an offset or other translation function determined based on the current position of fiducial mark "38" and the prior recorded position of the same fiducial mark. Analysis computer 28 may use the same offset or other translation function for each fiducial mark and anomaly, or analysis computer 28 may determine a unique offset or other translation function for each section of a web occurring between two consecutive fiducial marks. That is, analysis computer 28 may determine that the offset to be applied to anomalies between fiducial marks "38" and "39" is 0.011 m, while the offset to be applied to anomalies between fiducial marks "76" and "77" is 0.008 m.

In another embodiment, each process line may gather the local anomaly data independently of all other processes. That is, an analysis computer 28 for each manufacturing plant or product line records the positional data of fiducial marks and anomalies in database 32 as measured with respect to the coordinate system of the current process without regard to the position data recorded for the fiducial marks by any other process. Analysis computer 28 transmits this data to conversion control system 4 via network 9. Once all of the processes have finished, conversion control system 4 may reconcile all of the collected data.

As an example, the first process may have recorded fiducial mark "38" at a position of 76.027 m along the length of the web, while a subsequent manufacturing process applied to the web may have recorded fiducial mark "38" at 76.038 m. Likewise, the subsequent process may have recorded an anomaly at position 76.592 m. Conversion control system 4 may spatially register the fiducial mark "38" measured by the subsequent process by translating the position data to match 76.027 m measured during the first manufacturing process. Conversion control system 4 may then perform a similar translation on the position data for the anomaly detected during the subsequent process to record this anomaly as being present at position 76.581 m according to the calculated offset of 0.011 mm. As discussed above, conversion control system 4 may use the same offset for each fiducial mark and anomaly from each process, or conversion control system 4 may determine a unique offset for each section of a web from each process occurring between two consecutive fiducial marks. For example, conversion control system 4 may determine that the offset between fiducial marks "38" and "39" from process 5 is 0.011 m, while the offset between fiducial marks "76" and "77" from process 5 is 0.008 m. Other functions may be used to spatially register the data. For example, conversion control system 4 defines a coordinate system for use in spatially registering the locally anomaly data, conversion control system 4 may apply one or more mapping functions to map position data into the coordinate system.

FIG. 3 is a block diagram illustrating an exemplary sequence of manufacturing processes 50 applied to a single web. In an exemplary embodiment, the sequence of manufacturing processes 50 may perform numerous individual manufacturing processes upon web roll 7 by passing web roll 7 through individual process lines 74A-74Q ("process lines 74"). Process lines 74 may be provided by a single manufacturing plant 6 or may be located within different manufacturing plants.

In general, each of process lines 74 includes equipment to perform a number of operations 52 and one or more inspection systems to perform a number of inspection operations 54. There may be one or more inspections systems for each of process lines 74. Alternatively, there may be certain subset of process lines 74 that do not have inspection systems, while the rest of process lines 74 have one or more product inspections.

In an exemplary sequence of processes and inspections, such as that depicted in FIG. 3, a web roll 7 may be a plastic film, which may begin on process line 74A where the base film is first formed in accordance with operation 52A. On this process line, web roll 7 may be unwound and subjected to an initial inspection 54A. Operation 52A may, for example, clean web roll 7, operation 52B may prime web roll 7, and operation 52C may cure web roll 7. Web roll 7 may then be inspected a second time by inspection 54B and then wound into a roll.

Web roll 7 may subsequently be moved or shipped to process line 74B, where web roll 7 is then unwound for feeding into the process line 74B. In this example, operation 52D imparts web roll 7 with an embossed pattern and then 7 an inspection operation 54C is performed before being collected into a roll.

Additional manufacturing processes may be performed by subsequent process lines, until web roll 7 is shipped to a final process line 74Q, where web roll 7 is again unwound. As examples, operation 52N may coat web roll 7 with an opaque adhesive, operation 52P may uv-cure web roll 7 and laminate web roll 7 to a liner film, where there is one more inspection 54M before web roll 7 is rewound into the final form as web roll 10. Web roll 10 is then ready to be converted into products 12.

Any one of processes 52 may impart anomalies into web roll 7 that are subsequently identified as defects. Therefore, it may be desirable to inspect for defects within one or more of the different manufacturing process lines 74. For example, as shown in FIG. 3, there may be one or more inspections 54 for each of process lines 74. By frequently inspecting the web, the local anomaly data captured from the inspections at each of the process lines can be examined to individually optimize each of processes 52. This may allow for identification of the causes of defects for expeditious correction.

Moreover, the local anomaly data captured from the inspections at each of the process lines can later be spatially registered to form aggregate anomaly information that can be used for a variety of purposes. For example, the aggregate anomaly information can be examined to further optimize each of processes 52 based on their contribution to the overall defects in the end products. That is, depending upon the product application ultimately selected for the web, some of the operations performed by processes 52 may act to eliminate, cover or otherwise act to effectively remove or lessen the effect of an anomaly introduced by a previous one of the processes. An anomaly introduced into a base material of the web, for example, may be subsequently covered by coatings applied to the web. In addition, some so-called hidden anomalies may have little or no impact on the ultimate performance of the end products. The use of spatially registered aggregate anomaly information may allow conversion control system 4 to identify only the relevant anomalies from the multi-process production of a web based on a variety of factors, including the application selected.

Figure 4:
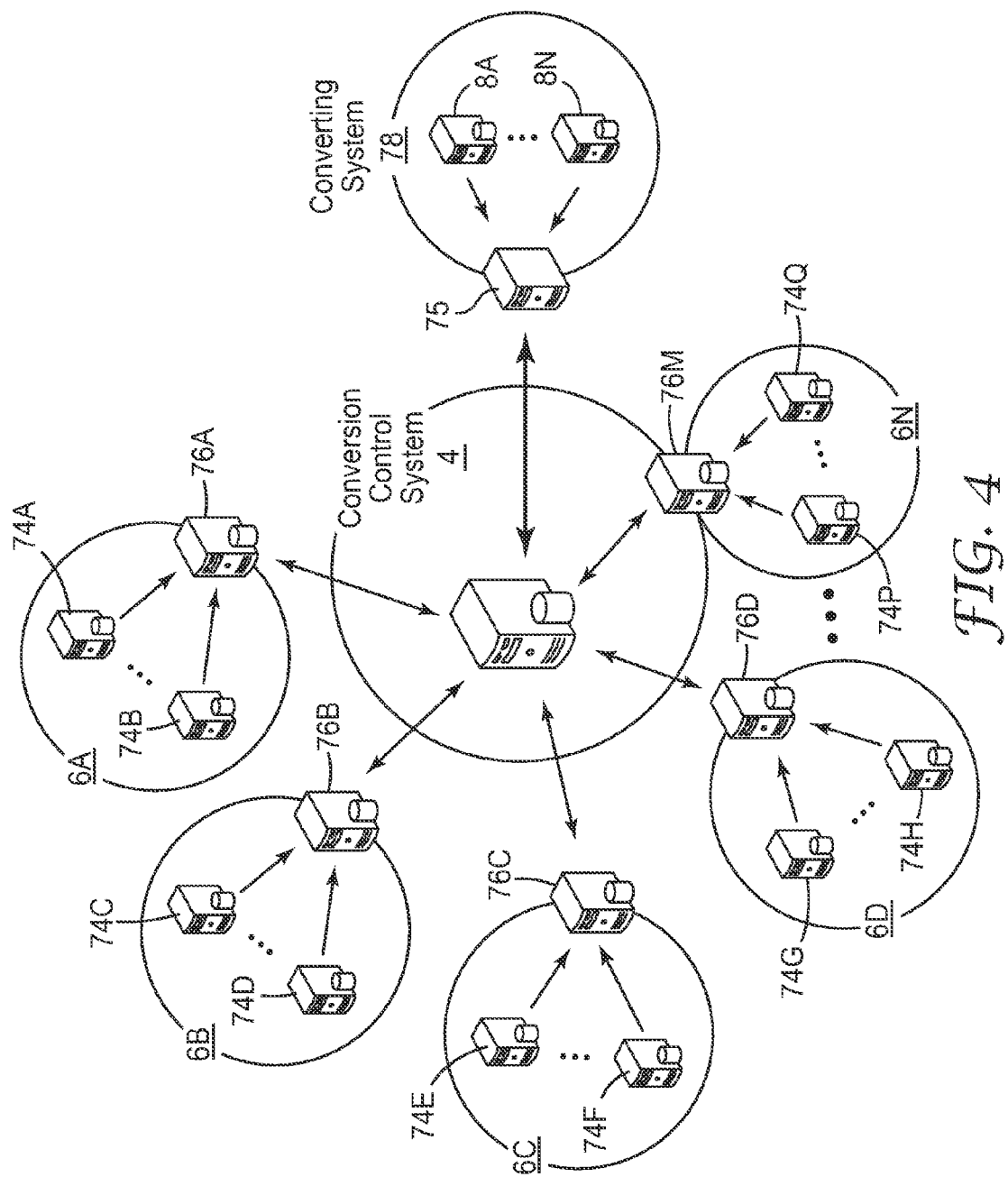
FIG. 4 is an illustration of the web manufacturing data collection and analysis system.

FIG. 4 is an illustration of an example embodiment of distributed web manufacturing system 2 shown in FIG. 1. Specifically, FIG. 4 depicts the certain elements of the example system FIG. 1 in greater detail. Each of web manufacturing plants 6 may comprise one or more process lines 74 having inspection systems and analysis computers as shown in FIGS. 2 and 3. In addition, each web manufacturing plant, for instance, web manufacturing plant 6A, may comprise a consolidation server, for instance, consolidation server 76A.

In some embodiments, a single processing line 74 may perform multiple operations on a web at various times. For example, process line 74A may be configured to perform a first operation or set of operations on web roll 7 using a first set of one or more coordinate systems and/or fiducial markings. Once process line 74A has finished the first operation, process line 74A may be reconfigured to perform a second operation or set of operations, potentially using a second set of one or more coordinate systems and/or fiducial markings. Web roll 7 may then be "reloaded," i.e. again placed at the start of process line 74A, and then process line 74A may perform the second operation or set of operations on web roll 7. In this way, a single process line, e.g. process line 74A, could potentially perform all necessary operations in the conversion process of web roll 7, and the position data for the first set of operations and the second set of operations can be spatially registered in accordance with the techniques described herein.

Each web manufacturing plant, for instance, web manufacturing plant 6A, may comprise one or more consolidation servers, for instance, consolidation server 76A for collection and communication of data. Consolidation server 76A may collect data from a respective analysis computer 28 of each of processes 74A-74B to transmit to conversion control system 4. Conversion control system 4 may collect and store global data corresponding to web rolls 10 as well as copies of the local anomaly information and the aggregate anomaly information for each of the rolls. In one embodiment, consolidation servers 76 assign particular "roll names" to each of web rolls 7. In another embodiment, consolidation servers 76 may assign roll names to segments of web rolls 7, 10. In one embodiment, consolidation servers 76 may associate roll names with particular web rolls or segments of web rolls and particular process lines 74; that is, any one web roll 7 may comprise a plurality of various roll names, each roll name corresponding to a different process line 74. In yet another embodiment, consolidation servers 76 do not assign any roll names to web rolls 7 but only identify web rolls 7 according to fiducial marks, for example, a series of fiducial marks as one of the fiducial marks depicted in FIG. 5.

In some embodiments, a consolidation server, for instance, consolidation server 76A, reconciles anomaly information produced at process lines 74B, for example, with the data collected from the first process line, for example, process line 74A, prior to communication to conversion control system 4. In another embodiment, each of consolidation servers 76A-76N may store local anomaly information received from each of process lines 74 without registration; conversion control system 4 may subsequently collect the local anomaly information from each of consolidation servers 76A-76N and reconcile all of the data internally within conversion control system 4 at a later time to form a composite map. In yet another embodiment, consolidation server 76A, for example, may receive instruction from conversion control system 4 in order to reconcile on-site any anomaly information generated for a web.

In one example, conversion control system 4 may gather and merge all data corresponding to each web roll 10 from consolidation servers 76. In another example, conversion control system 4 may create metadata which describes the external location of data regarding each web roll 10 (, e.g. by specifying a network address for each of consolidation servers 76); conversion control system 4 may later use the metadata to control merging of data from each of consolidation servers 76 regarding a particular web roll 10.

In one example, data may originate from a process line, e.g. process line 74A, of a particular location, e.g. plant 6A. Each web roll 10 may be assigned an identifier which may describe the product or products for which the particular web roll 10 is intended. The identifier may also uniquely identify the particular web roll 10.

In one example, each of web rolls 10 may undergo a particular "recipe." A recipe, generally, is a combination or defined sequence of process lines which operate to manipulate the particular web roll 10. For example, one recipe may be process line 74A of plant 6A, process line 74E of plant 6C, and process line 74Q of plant 6N.

Because web rolls 10 are unwound and rewound at process lines 74, conversion control system 4 may identify the direction in which the roll was traveling on the process line in order to facilitate merger of the data. Direction of the web roll may be determined based on analysis of the fiducial marks. In one embodiment, for example, fiducial marks may be a sequence of integers which increment by one for each sequential fiducial mark; thus it may be possible to determine direction of the web roll (i.e., which end of the roll was fed first into the manufacturing process) by analyzing whether the fiducial marks are ascending or descending.

Once all of the data has been reconciled, conversion control system 4 may transmit the composite map and a conversion plan to server 75 of converting system 78, such as by using the File Transfer Protocol (FTP) or any other data communications protocol. Web rolls 10 may be shipped to one of converting sites 8A-8N ("converting sites 8"). Converting sites 8 may utilize the composite map and the conversion plan from conversion control system 4 in transforming web rolls 10 into products 12.

Figure 5A:
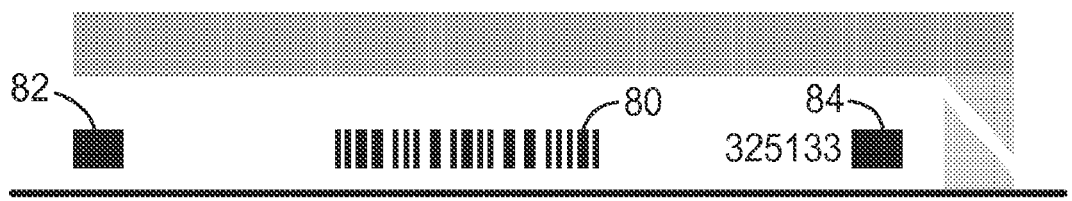
FIGS. 5A-5B are diagrams illustrating exemplary fiducial marks.

FIG. 5A is a diagram illustrating one embodiment of an example fiducial mark that may be printed or otherwise formed on an individual web. More specifically, fiducial marks are placed at regular intervals throughout the length of a web (FIG. 7), preferably outside of the salable area of the web, in order to accurately locate and uniquely identify a physical location on the web. As described herein, the techniques may utilize fiducial marks to enable electronic position data to be accurately spatially registered and combined for multiple unit operations containing various error sources, production lines and even manufacturing plants. In other words, the fiducial marks allow a reader to later detect and record errors relative to the position of the fiducial mark(s). Although shown as including a barcode and other features, other forms of indicia may server such purposes.

In an embodiment of a fiducial mark as depicted in FIG. 5A, a fiducial mark has one or more locating marks 82, 84 and a barcode 80. Locating marks 82, 84 enable a fiducial mark reader to accurately locate the position of barcode 80. Barcode 80 represents information provided in a machine-readable format. Barcode 80 may, for example, encode a unique identifier for each fiducial mark. Barcode 80 may encode other information, such as position information based on a coordinate system used when applying the mark, an identifier for the web to which the mark has been applied, designation of production lines used or scheduled to be used for manufacturing the web, routing information defining a route for the web through manufacturing process lines and/or manufacturing plants, information identifying the material applied and in which order and area of the web, environmental conditions measured during the process, instructions for downstream processing of the web, and a host of other information.

In one embodiment, barcode 80 may conform to the interleaved "2 of 5" symbology standard. In one embodiment, barcode 80 may represent a simple integer in the range from 0 to 999,999. In one embodiment, each fiducial mark placed on a web is one greater than the previous fiducial mark. In one embodiment, fiducial marks may be applied to a web using an inkjet printer. The process of placing fiducial marks on a web is described in further detail in co-pending application Floeder et al., U.S. App. No. 2005/0232475, Apparatus and Method for the Automated Marking of Defects on Webs of Material (published 2005), which is hereby incorporated by reference in its entirety.

Other embodiments may represent fiducial marks in a variety of other ways. For example, data may be represented by a 1D barcode, a 2D barcode, optical character recognition (OCR), or magnetically encoded. Furthermore, other embodiments may apply fiducial marks to a web using inkjet printing, laser printing, or by securing mechanical labels to the web. Other means of representing a fiducial mark, as well as other application methods, may also be used. Further, fiducial marks need not be iterating nor periodically spaced, as fiducial marks merely serve as a reference point for anomalies; iterating fiducial marks is merely a convenient way of producing fiducial marks.

In general, fiducial marks are used to combine electronic data of anomalies recorded from various inspections. During a first manufacturing process, fiducial marks may already be present on the web, preferably near the edge of the web outside of the salable product. If fiducial marks are not present, the first manufacturing process applied to the web should apply fiducial marks, e.g., at regular intervals along the edge of the web. In one embodiment, each fiducial mark represents an integer one unit greater than the previous fiducial mark. In one embodiment, fiducial marks are recorded on the web approximately two meters apart. Precise distance may not be required between fiducial marks, as fiducial marks serve as a relative indicator of position.

Figure 5B:
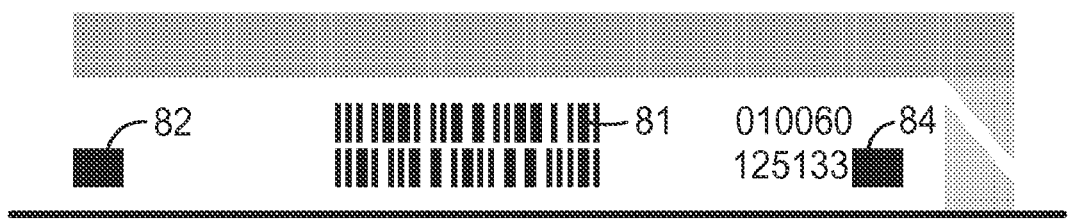

FIG. 5B depicts another example embodiment of a fiducial mark. In this embodiment, the fiducial mark comprises two locating marks 82, 84 which are substantially similar in purpose and function as those depicted in FIG. 5A. However, barcode 81 of FIG. 5B is substantially different from barcode 80 of FIG. 5A and is represented as a compound fiducial mark that includes a barcode 81 having a first mark to represent manufacturing data and a second mark to uniquely identify the fiducial mark. Specifically, in this example, barcode 81 comprises twelve digits of information in the interleaved 2 of 5 format, six digits in each of an upper tier and a lower tier. Although discussed with respect to the interleaved 2 of 5 format, other barcode formats may be used as well. In this example, the lower tier digits form a simple integer in the range from 0 to 999,999. The upper tier comprises three pieces of information, a system identifier (ID) indicating the manufacturing process line that applied the fiducial mark and a date represented as day and year indicating when the fiducial mark was applied. The upper tier digits may be arranged as SSYDDD, and the lower tier digits may be arranged as a six digit integer ######. The contents of exemplary barcode 81 are summarized in Table 1 below.

TABLE 1

| Description | Representation | # of Digits |
| --- | --- | --- |
| System ID | SS | 2 |
| Year | Y | 1 |
| Day of Year | DDD | 3 |
| Six Digit Identifier | ###### | 6 |

The system IDs may be divided among manufacturing plants 6. For example, the system IDs could be distributed as shown in Table 2 below.

TABLE 2

| System ID | Plant | Description |
| --- | --- | --- |
| 00-04 | Plant 6A | Plastic Film |
| 05-09 | Plant 6B | Adhesive Coating |
| 10-19 | Plant 6C | Abrasive Products |
| 20-29 | Plant 6D | Metal Coating |
| 30-79 | RESERVED | RESERVED |
| 80-99 | Plant 6N | Film Lamination |

The use of multi-tiered barcodes may provide several advantages. For example, multi-tiered barcodes are compatible with readers designed to read only a single tiered barcode (e.g., FIG. 6) by simply utilizing multiple readers. Likewise, this multi-tiered barcode may encompass all information needed to uniquely identify all processes and specific systems across an entire manufacturing chain of operations. Fiducial marks from different processes may be applied to the same web without any loss of information or creating ambiguities. One exemplary method for inserting fiducial marks one a moving web is discussed below with respect to FIG. 15.

Figure 6:
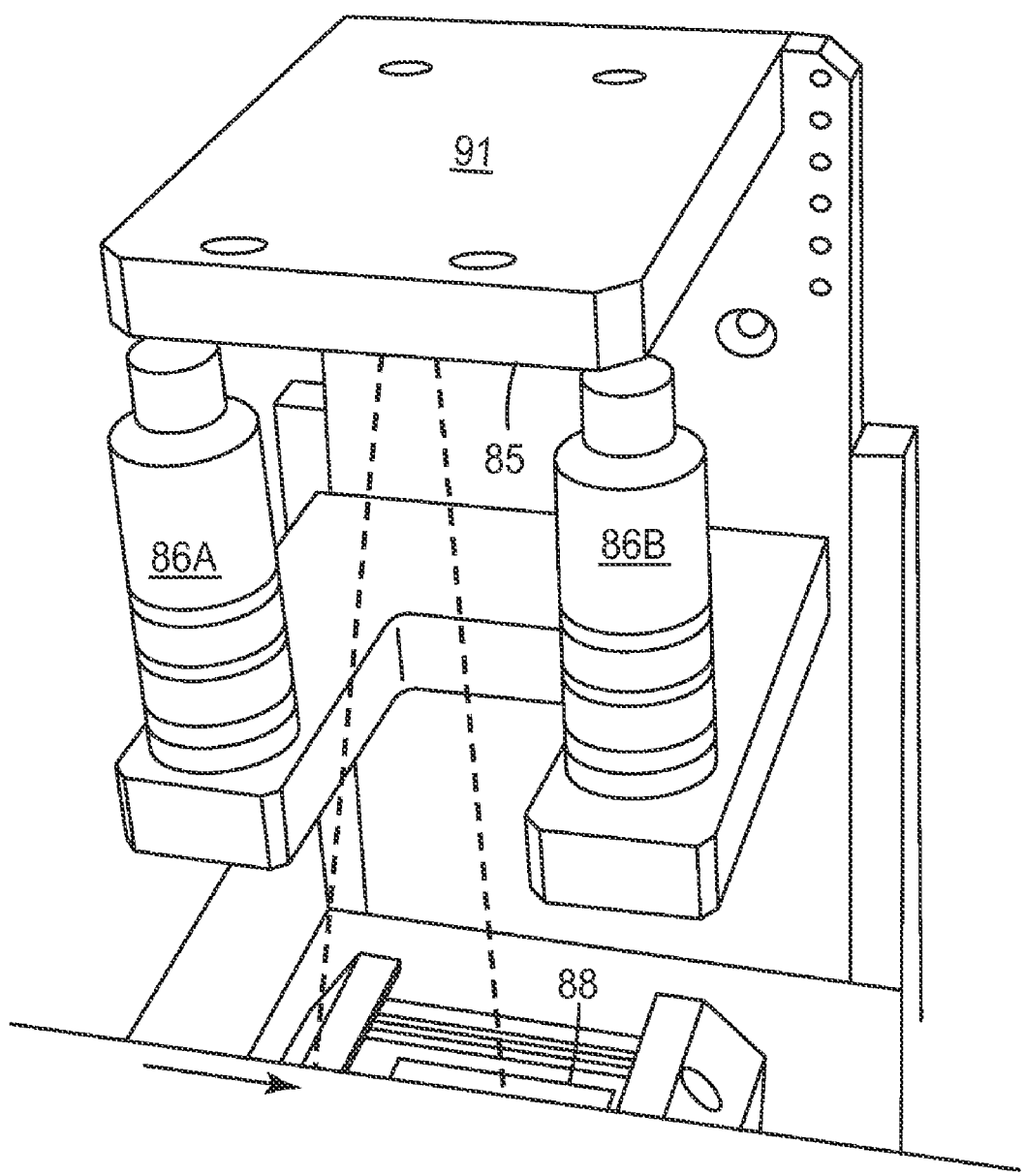
FIG. 6 is a picture of an exemplary fiducial mark reader.

FIG. 6 is an illustration of an exemplary fiducial mark reader 29 (FIG. 2). In the illustrated example, fiducial mark reader 29 includes a frame having a barcode reader 85, two fiducial sensors 86A, 86B, and a light source 88 mounted thereon. In addition, fiducial mark controller 30, which may be a microcontroller or general processor, may be embedded within fiducial mark reader 29 or coupled to reader 29 by a suitable electronic data path.

Fiducial mark controller 30 receives signals from fiducial sensors 86A and 86B and activates bar code scanning upon detecting both locating marks 82, 84 of a fiducial mark either simultaneously or within a predefined time period, e.g., 0-10 milliseconds. In this manner, fiducial sensors 86A and 86B are used to determine when the barcode is within a read zone associated with barcode reader 85. Fiducial sensors 86A and 86B may be photo-optic sensors accompanied by focusing optics. In one embodiment, fiducial locators 82, 84 are printed or otherwise placed at a predefined width W apart on the web, and fiducial sensors 86A and 86B are mounted on the frame of fiducial mark reader at the width W apart in order to substantially simultaneously detect both locating marks 82, 84. In one example, the width W is selected to be 100 mm.

When both sensors 86A and 86B detect a corresponding locating mark, fiducial mark controller 30 activates light source 88 in order to read barcode 80 of the fiducial mark. In some embodiments, light source 88 may remain lit at all times. In other embodiments, light source 88 may be illuminated only when both fiducial sensors 86A, 86B detect locating marks substantially simultaneously. In one embodiment, when both fiducial sensors 86A and 86B detect locating marks 82, 84, barcode reader 85 captures an image of barcode 80 rather than processing the image data to read the bar code in real-time. Fiducial mark controller 30 may store the image in database 32, and image data representative of the captured barcode 80 may be read and interpreted at some later time. In another embodiment, fiducial mark controller 30 directs barcode reader 85 to capture an image of barcode 80 for processing in real-time to read the barcode. That is, barcode reader 85 may extract the data from the image of barcode 80 and analyze the image data to determine the machine-readable information contained therein.

Once barcode reader 85 has read barcode 80, fiducial mark reader 29 may convert the information read from barcode 80 into digital data in the form of an integer. Fiducial mark reader 29 may transmit this data to fiducial mark controller 30. At this time, fiducial mark controller 30 may determine the position of the moving web based on encoded reference signals received from encoder wheels engaged with the web. Fiducial mark controller 30 may then transmit the position information as well as the barcode data to analysis computer 28. Analysis computer 28 may combine the identifier read from barcode 80 with the data representing the physical location of the fiducial mark and store this information in database 32. In one embodiment, fiducial mark controller 30 communicates data to analysis computer 28 over a computer network using networked sockets or other network communication protocols. Other suitable means for communicating data may also be used.

Figure 7:
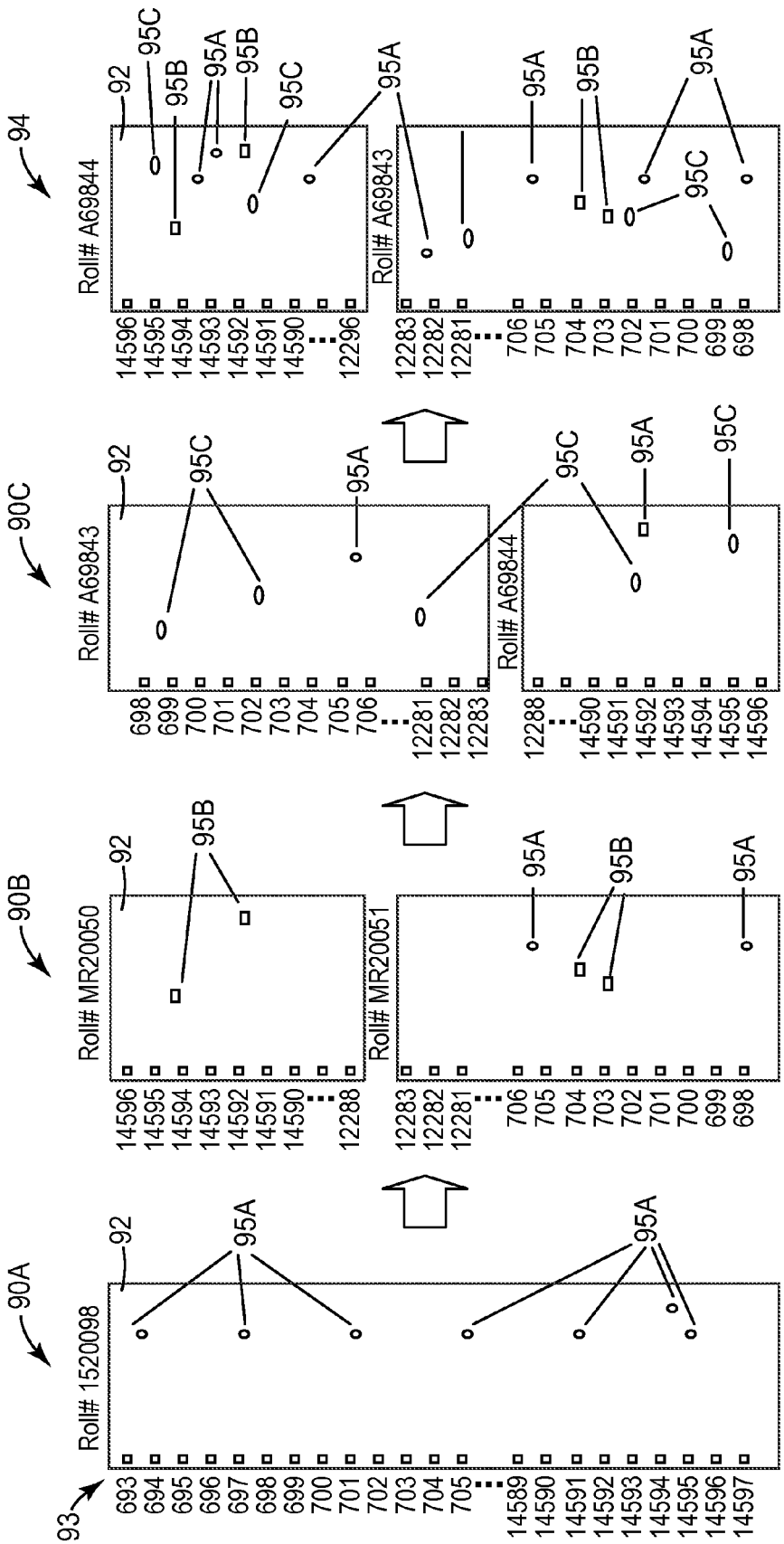
FIG. 7 is a diagram illustrating a web and the changes it may undergo, including the later introduction of new anomalies and masking of previous anomalies.

FIG. 7 is a diagram illustrating an example web 92 and example changes the web may experience, including the initial introduction of anomalies, followed by the subsequent introduction of new anomalies and masking of some of the previous anomalies. In this example, a web is manufactured using three sequential manufacturing processes 90A, 90B and 90C corresponding, potentially, to three different production lines. In order to properly manufacture the web, the web may need to be transferred between multiple process lines 74 to reach the correct processes 90A-90C in the correct order. This transferring may include winding the web into a roll and moving it to a different process line in the same manufacturing plant or even shipping it to a different plant, as depicted with respect to FIGS. 1, 3.

As shown in FIG. 7, each of manufacturing processes 90A-90C may introduce its own anomalies into web 92. Furthermore, each manufacturing processes 90A-90C may change the web 92 in such a way that earlier anomalies would be difficult, if not impossible, to detect. As certain processes 90A-90C operate on the web, the operations (e.g., cleaning, coating, etc.) may change web 92 in a way that makes it difficult or impossible to discover anomalies introduced by an earlier process in the final web. As described, each of manufacturing process 90A-90C may inspect the web at least once, thereby collecting data regarding the anomalies detectable during each of the manufacturing processes.

Specifically, in the example of FIG. 7, a first roll (Roll # 1520098) is initially processed in manufacturing process 90A at which time a set of fiducial marks 93 to the web 92. As shown, the fiducial marks are assigned identifiers of 693-14597 and are physical "registration markers" that enable electronic data to be accurately combined in multiple unit operations containing various error sources. During the first manufacturing process 90A, a first set of anomalies 95A are created within web 92 and detected by one or more inspection systems.

Next, web 92 is cut and wound into two rolls (MR20050 and MR20051) for processing by a second manufacturing process 90B. In this process, web 92 is unwound form the rolls and fed in the opposite direction through manufacturing process 90B. As shown, manufacturing process 90B has introduced a second set of anomalies 95B. A subset of the initial anomalies 95A is still detectable, with the remaining portion being hidden from the inspection systems of manufacturing process 90B.

Next, web 92 is wound into two rolls (A69844 and A69843) for processing by a third manufacturing process 90C. In this process, web 92 is unwound form the rolls and fed through manufacturing process 90B in the original direction used during the first manufacturing process 90A. As shown, manufacturing process 90C has introduced a third set of anomalies 95C. A subset of the anomalies 95A, 95C are detectable, with the other anomalies being hidden from the inspection systems of manufacturing process 90C.

Composite map 94 shows the local anomaly data from each of processes 90A-90C once spatially registered and consolidated to form aggregate anomaly data. Composite map 94 may include registered data. Registered data may be considered data corresponding to a common segment of web roll 7 from a plurality of processes 74, wherein the data is aligned to within an acceptable tolerance. That is, data generated by different processes 74 is correctly associated with substantially the same physical locations on the web within the acceptable tolerance. To create the composite map 94, conversion control system 4 may spatially synchronize the local anomaly data from each process 90A-90C, including position data for detected anomalies as well as position data for the fiducial marks 93 read during each of the processes, to a specified tolerance, i.e. a degree of accuracy. A high degree of accuracy may be, for example, on the order of 0-2 mm. A standard degree of accuracy may be, for example, within 5 mm. A registration falling outside of 150 mm, or about 6 inches, may be considered "unregistered" because of a high degree of error. As shown in FIG. 7, the exemplary composite map 94 includes all of the anomalies 95 detected by the inspection systems for all processes 90A-90C.

Composite map 94 describing the combined anomalies may be used to accept or reject an individual portion of web 92 when converting the web into finished products. Composite map 94 may also be used to selectively optimize each individual of the manufacturing process 90A-90C.

As an example, if a web consists of a printed circuit pattern, an anomaly causing a defect may be an erroneous piece of conductive material causing a short. In a later process, the board may be coated with an opaque dielectric which makes the short undetectable. By inspecting this web once after the process of printing the conductive material, but before coating the web with the insulator, it may be possible at a later time to determine that this shorted region of the web will be defective even though it is not possible to detect the anomaly in the final form of the web due to the opaque, insulating coating. Another similar example may be if, rather than a short, the conductive material printer failed to print, causing a circuit to remain open. Again, later application of an opaque dielectric would make the "open" circuit undetectable. Due to the inspection before the application of the dielectric, this defect may be discovered, and the defective product removed from the pool of products to be delivered, before a delivery is ever made to a customer.

Figure 8A:
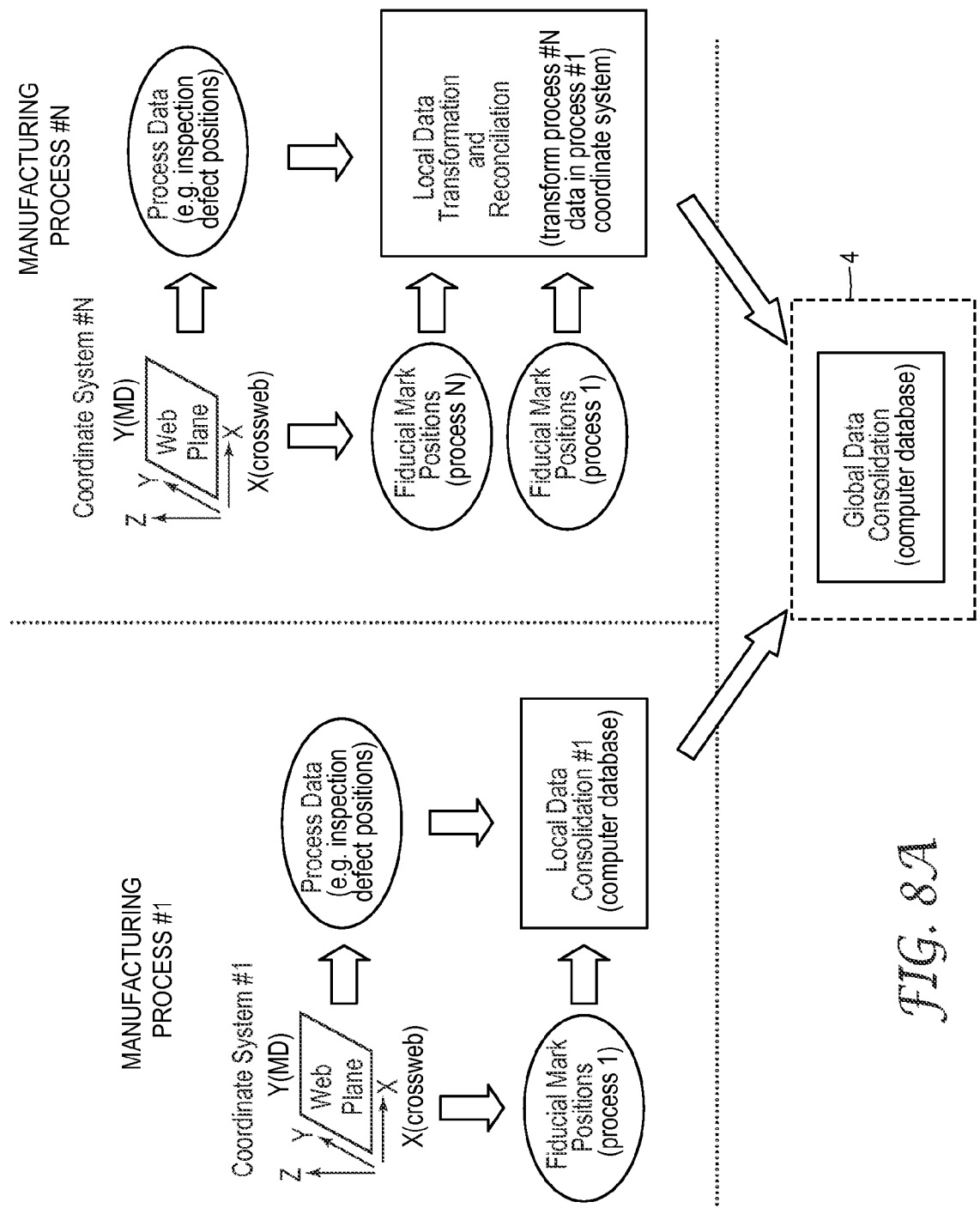
FIGS. 8A and 8B are block diagrams illustrating the aggregation of data in accordance with two exemplary embodiments of the techniques described herein.
Figure 8B:
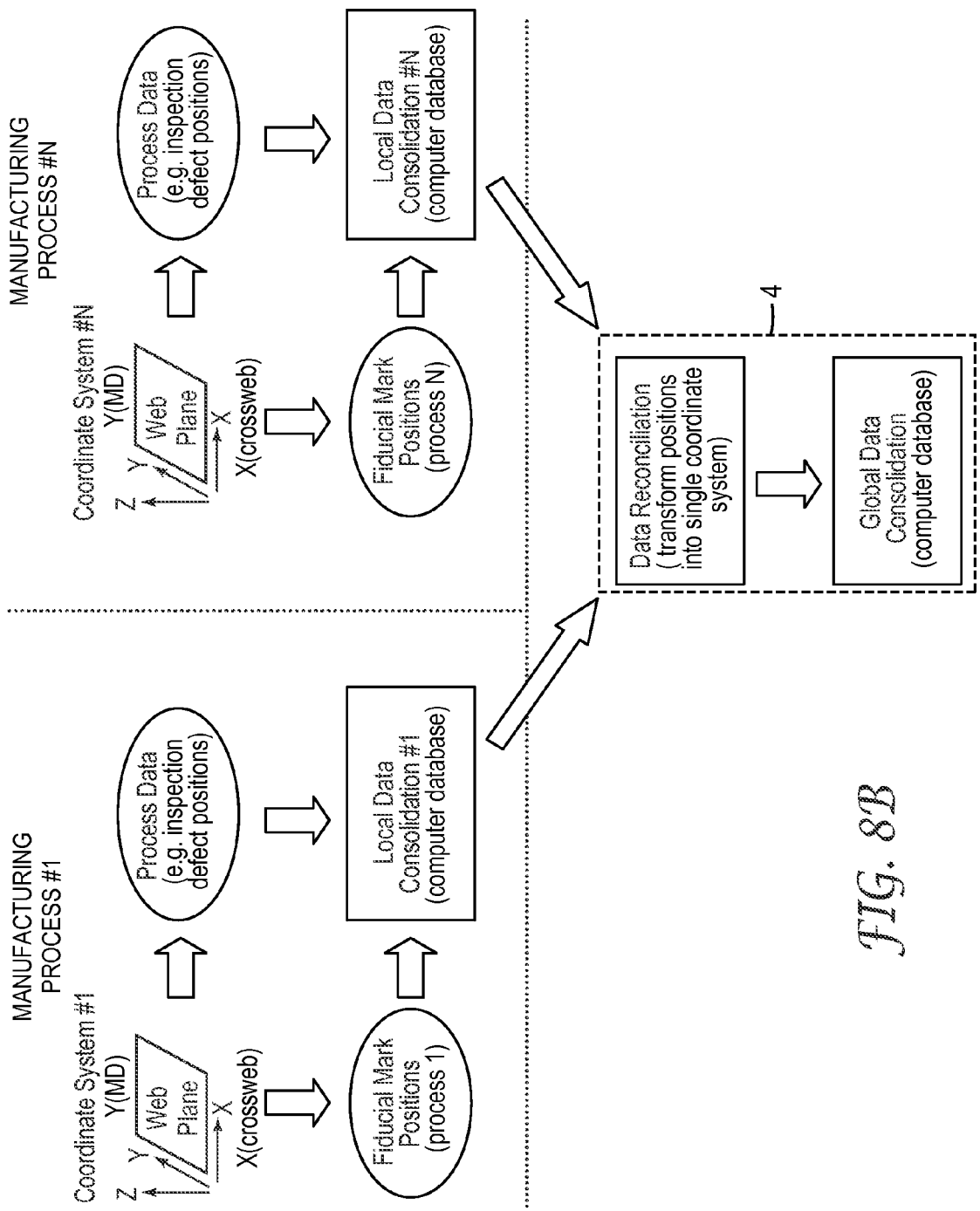

FIGS. 8A and 8B illustrate exemplary embodiments the functional operations and data communications performed within the network environment 2 (FIG. 1) when consolidating and spatially registering anomaly data from a plurality of different manufacturing process. In FIGS. 8A and 8B, the first manufacturing process (Unit Process #1) records data relative to its own local coordinate system. That is, if the first process determines that fiducial mark "7684" is at 11,367.885 m, the first process will record fiducial mark "7684" at 11367.885 m. Likewise, if the first process determines that there is an anomaly after mark "7684" at position 11,368.265 m, the first process will record an anomaly at position 11,368.265 m. Alternatively, the first manufacturing process may translate data to a coordinate system defined by conversion control system 4. In either case, every local manufacturing process is referenced to a pre-defined coordinate system so that all processes are automatically spatially synchronized.

In the example of FIG. 8A, each subsequent manufacturing process N applies its own coordinate system (coordinate system #N) when reading the fiducial marks and the positions associated with the fiducial marks and anomalies in a manner similar to the initial process. However, the way in which this information is recorded within these subsequent manufacturing processes record is different than the initial process. These subsequent processes record the distance of fiducial marks and anomalies by applying a transformation function to adjust the measured distances based on the data obtained from the initial process. That is, these subsequent manufacturing processes register position data by transforming the position data from the coordinate system N of the current process N to the coordinate system of the initial process. As inputs, an analysis computer 28 for the subsequent manufacturing process N uses position data read during the current manufacturing process N as well as initial position data for the same fiducial marks with respect to the target coordinate system, e.g., coordinate system #1 for manufacturing process #1 in this example.

A variety of transformation functions may be used. For example, position data for the current manufacturing process N may be transformed with respect to either a global offset, that is, an offset common to the entire web, or an offset calculated for each segment of a web between two fiducial marks. For example, the respective analysis computer may process the position data for the relevant fiducial marks and determine that an offset of 0.004 m should be applied to position data for anomalies detected between fiducial marks "13" and "14," but an offset of 0.007 m should be applied to position data for anomalies detected between fiducial marks "20" and "21." Other techniques, such as linear interpolation or application of linear scale factors, may be applied.

As another example, the first manufacturing process may record fiducial mark "61" at position 112.343 m. A subsequent manufacturing process N, however, may record the position of fiducial mark "61" at 112.356 m, an offset of 0.013 m. The subsequent manufacturing process N, according to an embodiment as illustrated in FIG. 8A, may adjust its data accordingly to record fiducial mark "61" as being present at location 112.343 m, and analysis computer 28 of the subsequent unit operation may also adjust data about anomalies detected after this fiducial mark to reflect this offset as well. For example, if the subsequent unit operation detects an anomaly at 112.487 m, analysis computer 28 may utilize the offset of 0.013 m to adjust the position of the anomaly, recording the anomaly at position 112.474 m.

In this manner, each manufacturing process will have produced spatially registered local anomaly data that is based on a common coordinate system. Alternatively, as shown in the example of FIG. 8B, conversion control system 4 may apply similar technique to spatially register the anomaly data. In either case, conversion control system 4 may collect the local anomaly data and store the data as aggregate anomaly data for the web. Conversion control system 4 then forms a composite map showing the aggregate anomalies from the data gathered from each manufacturing process by, for example, utilizing an "or" function. That is, conversion control system 4 may record an anomaly at a certain position on the composite map if any one of the processes have recorded that an anomaly is present at that position to within an acceptable degree of accuracy as described in greater detail below. Conversion control system 4 may also categorize the anomaly by class. The composite map can be used later to determine whether a certain anomaly in a certain position will cause a defect in a certain product.

FIG. 8B illustrates another embodiment in which spatial registration is performed centrally, e.g., within conversion control system 4. In this embodiment, each individual manufacturing process defines and references its own coordinate system. That is, position data gathered during each individual manufacturing process, such as the physical location of fiducial marks and anomalies, are recorded with respect to this individual coordinate system. After all of the manufacturing process have finished, or optionally as position data is received from the manufacturing processes, conversion control system 4 adjusts the position data from all of the operations according to a common coordinate system and used to generate a composite map. The composite map may comprise all previously recorded data in a single coordinate system.

As an example, an analysis computer 28 for a first manufacturing process may record fiducial mark "61" at position 112.343 m in database 32. An analysis computer 28 associated with a subsequent manufacturing process, however, may record the position of fiducial mark "61" at 112.356 m, an offset of 0.013 m. The subsequent manufacturing process, according to an embodiment as illustrated in FIG. 8B, may record fiducial mark "61" as being present at 112.356 m. At some time later, conversion control system 4 may generate a composite map in which fiducial mark "61" is recorded at 112.343 m, taking into account the 0.013 m offset, and accordingly adjusting all position data regarding defects and anomalies neighboring fiducial mark 61. For example, if the subsequent process recorded an anomaly at 112.487 m, conversion control system 4 will record the position of the anomaly at 112.474 m according to the offset at 0.013 m. Alternatively, a scale factor may be used, as discussed in detail below. In any case, conversion control system 4 utilizes a single coordinate system and translates position data for fiducial marks and anomalies to the single coordinate system when generating the composite map. Conversion control system 4 may furthermore generate the composite map from the data gathered from each process by utilizing an "or" function. That is, conversion control system 4 will record an anomaly at a certain position on the composite map if any one of the manufacturing processes have recorded that an anomaly is present at that position.

The techniques described herein may be applied to overcome a variety of factors that would prevent anomaly information from multiple manufacturing processes from being used. For example, position data relative to local process coordinate systems generated by external devices, such as rotational encoders engaged with a moving web, may differ from each other. However, differences in position data from different manufacturing processes are not only a result of differences in the measurement systems, but also the result of spatial changes in the product itself. For example, processing, winding, transportation, unwinding and reprocessing of webs may cause the webs to stretch during the multiple manufacturing processes.

The differences in position data between manufacturing processes can cause the position of web events, such as anomalies and defects, measured in one coordinate system to effectively "drift" relative to another coordinate system as a web is traversed, i.e., fed through the manufacturing process. In some case, positional differences in excess of 0.75% have been observed. In a system where fiducial marks are placed 2 meters apart, such differences would result in a discrepancy of 14 mm before re-registration by a subsequent fiducial mark. That is, the "drift" caused by system differences across unit operations can result in absolution positional errors up to 14 mm with variability ranging from 0 to 14 mm depending on the distance from the most recent barcode.

The techniques described herein may be applied to spatially register anomaly information produced by web inspection systems at each of the manufacturing process. For example, one technique to correct this uncertainty and inaccuracy is a positional correction method using a linear transformation. In one embodiment, as discussed with respect to FIG. 8A, after the initial manufacturing process, each subsequent manufacturing process may perform linear transformations to register position data for detected anomalies. In another embodiment, a centralized system, such as conversion control system 4, performs the linear transformation for all data.

In either case, one example of a linear transformation is as follows: for the first unit process, let $EP_n$ be the measured position of fiducial mark n and let $D_n = EP_n - EP_{n-1}$. For the process being adjusted, let $P_n$ be the measured position of fiducial mark n and let $M_n = P_n - P_{n-1}$. Let the scaling factor (SF) be: $SF_1 = 1$ and $SF_n = M_n / D_n$ for all n>1. For an anomaly j, initially measured in position $IP_j$ between fiducial marks k and k+1, the adjusted position $AP_j$ is $[(IP_j - EP_k) * SF_{k+1}] + P_k$. In other words, the distances between the fiducial marks k and k+1 as originally measured and as measured in a subsequent process are used to form a scaling factor SF specific to those two fiducial marks K and K+1. The distance between any anomaly and the fiducial mark after which the anomaly occurred is scaled to fit the target coordinate system according to the scaling factor as described above.

Figure 15:
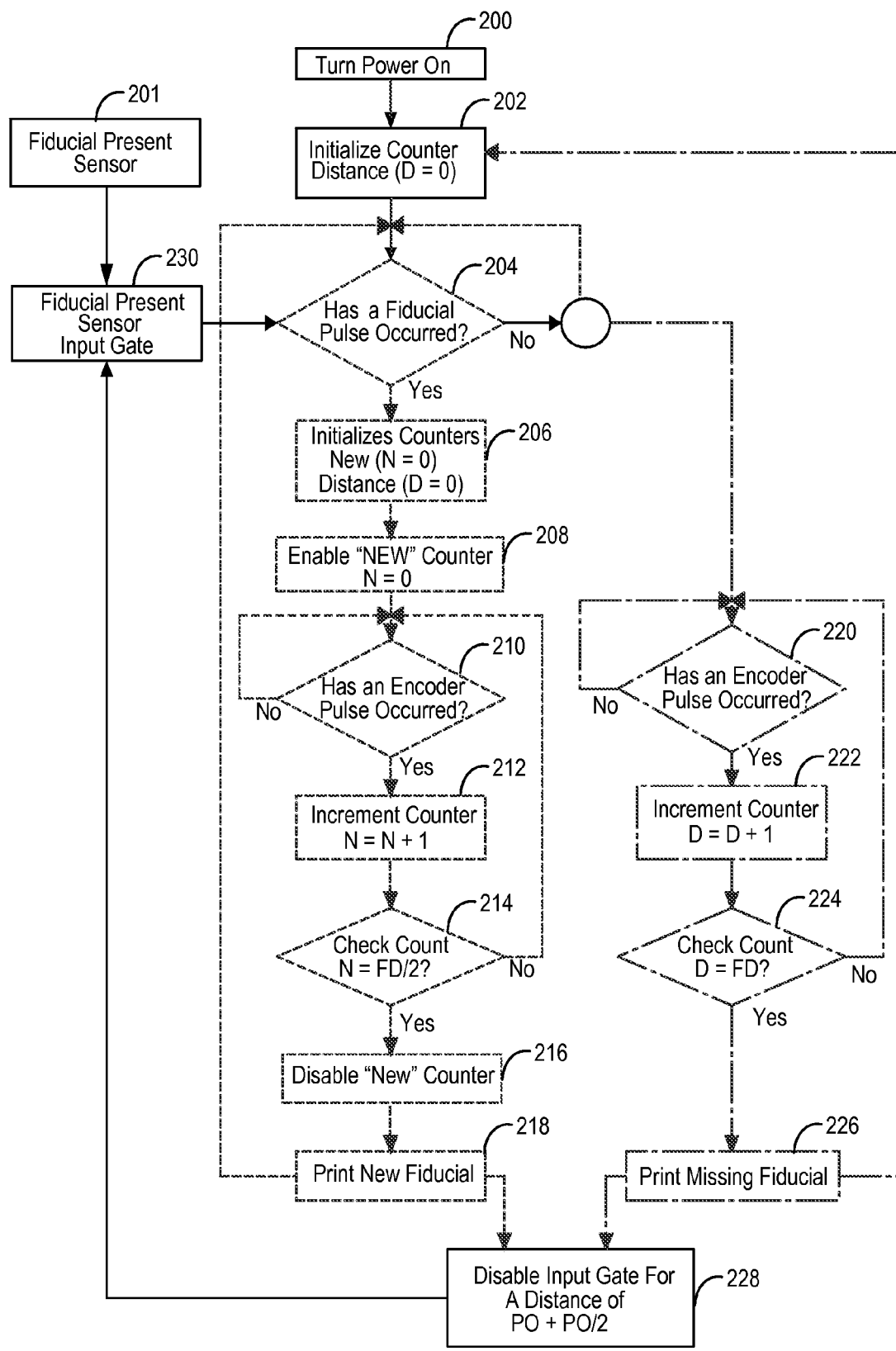
FIG. 15 is a flowchart illustrating exemplary operations involved in application of fiducial marks to a web.

Table 3 compares the difference between using a simple offset computed for each pair of fiducial marks, and the linear transformation that applies a scaling factor as discussed above. In Table 3, the "distance from mark" measurement is the difference between the mark position and the event position. The simple offset error is the difference between the "distance from mark" measurements of the two processes. As shown in Table 3, when only using re-registration and a simple offset, positional accuracy can vary significantly with a maximum discrepancy of 13 mm. However, the linear transformation and application of a scaling factor has virtually eliminated any residual error that would otherwise result from application of a simple offset.

applying fiducial marks to a web is described in further detail herein, such as with respect to FIG. 15.

The web is then collected into a web roll 7 and shipped to one of process lines 74, for instance, process line 74A, at one of web manufacturing plants 6 (104). Process line 74A then processes web roll 7, during processing, the process line also collects inspection data from the web (106). The process line may collect inspection data one or more times during processing. Example operation of a process line 74A, including data collection and spatial registration, is discussed in further detail with respect to FIG. 10.

Once process line 74A is finished, the web may be sent to another of process lines 74 for further processing (108). That is, if the completed process line was not the last process line for the web ("NO" branch of 108), web roll 7 may be shipped to another process line, e.g., another one of processing lines 74 (110).

If, however, the completed process line is the last process line ("YES" branch of 108), the web represents a finished web roll 10 and is shipped to one of converting sites 8 (112). Conversion control system 4 electronically communicates data representing a composite map of the anomaly information regarding web roll 10 to the converting site with web roll 10. In one embodiment, conversion control system 4 creates the composite map from anomaly information collected from each of the process lines 74 which were involved in manufacturing web roll 10. In forming the composite map, conversion control system 4 may spatially register the anomaly information using, for example, a linear transformation function, discussed herein and in detail with respect to FIGS. 13, 14.

Figure 10:
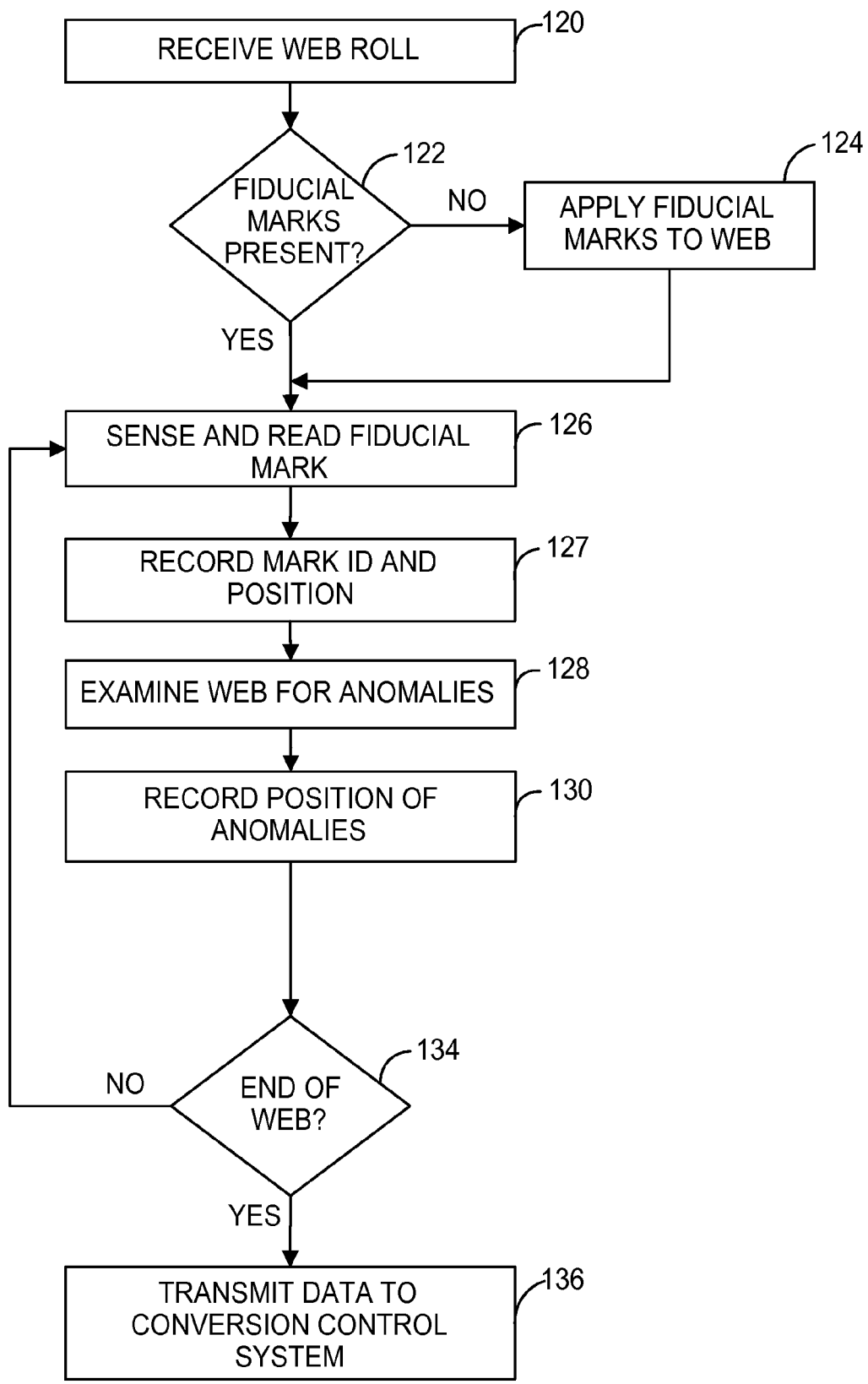
FIG. 10 is a flowchart illustrating the inspection steps of a process line.

FIG. 10 is a flowchart illustrating example operation carried out by a manufacturing process line, for instance, process line 74A. Initially, process line 74A receives web roll 7 (120).

TABLE 3

| | Process #1 Coordinate System | | | Process #N Coordinate System | | | Consolidation Error | |
|---|---|---|---|---|---|---|---|---|
| Fid. Mark Label | Fid. Mark Position | Event Position | Dist. From Mark | Fid. Mark Position | Event Position | Dist. From Mark | Simple Offset | Linear Correction |
| 96855 | 132.687 | 132.991 | 0.304 | 133.616 | 133.922 | 0.306 | 0.002 | 0.000 |
| 96855 | 132.687 | 134.428 | 1.741 | 133.616 | 135.369 | 1.756 | 0.012 | 0.000 |
| 96856 | 134.680 | 135.433 | 0.753 | 135.623 | 136.381 | 0.758 | 0.005 | 0.000 |
| 96857 | 136.590 | 136.594 | 0.004 | 137.546 | 137.550 | 0.004 | 0.000 | 0.000 |
| 96857 | 136.590 | 137.555 | 0.965 | 137.546 | 138.518 | 0.972 | 0.007 | 0.000 |
| 96857 | 136.590 | 138.399 | 1.809 | 137.546 | 139.368 | 1.822 | 0.013 | 0.000 |
| 96858 | 138.641 | 139.874 | 1.233 | 139.611 | 140.853 | 1.242 | 0.009 | 0.000 |
| | | | | | | Max | 0.013 | 0.000 |
| | | | | | | Mean | 0.007 | 0.000 |
| | | | | | | Min | 0.000 | 0.000 |

Figure 9:
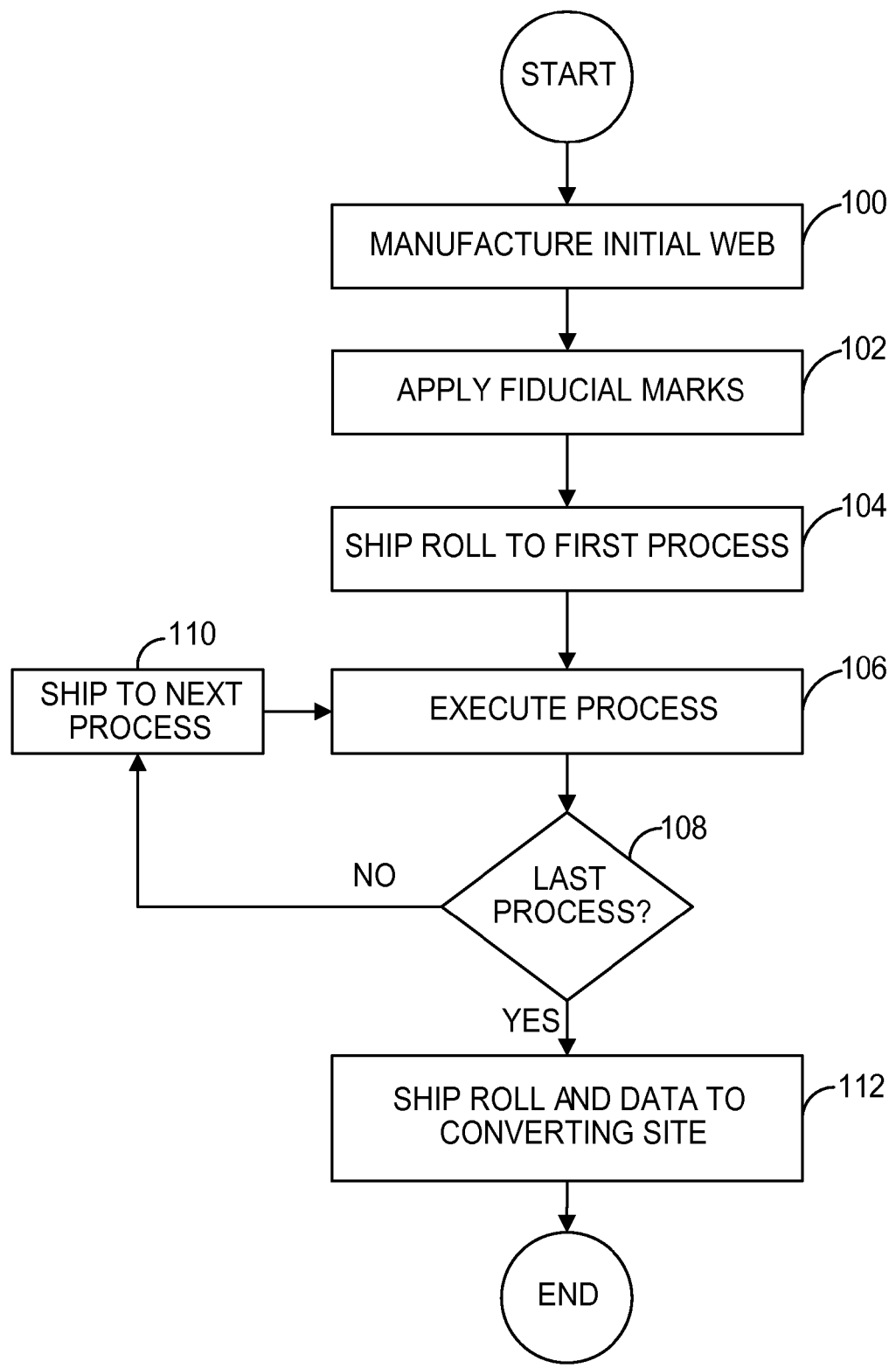
FIG. 9 is a flowchart illustrating the production of a web.

FIG. 9 is a flowchart that provides a high-level overview of the production of a web. Initially, a customer, or a set of customers with similar needs is identified or requests a product according to certain specifications. For example, a group of customers may request a film for glass protection; customer A may request films cut to fit automobiles, customer B may request similar films, but cut to fit home windows, and customer C may request films cut to fit commercial building windows.

An initial web is manufactured, e.g., at web manufacturing plant 6A, to serve as the base for the products (100). Fiducial marks may be applied at this time to the edge of the web outside of the salable product area (102). The process of In one embodiment, process line 74A may also receive data from conversion control system 4 from the previous process line, for example, process line 74B. For example, conversion control system 4 may provide instructions as to whether spatial registration should be performed locally, i.e., by the current process line 74A or whether the conversion control system will subsequently perform the registration. As another example, conversion control system 4 may provide data necessary for the current process line to spatially register position data to a given coordinate system, such as the coordinate system used by the first processing line applied to the web.

Next, the web roll is loaded and feeding of the web into the process line 74A commences. If fiducial marks are not already present on the web (122), process line 74A is configured to apply fiducial marks at an early stage. Typically, fiducial marks should be in place before web roll 7 is applied to the first process line, though there may be instances where fiducial marks are corrupted and need to be replaced. In addition, a process line may be configured to apply additional fiducial marks to a web already having fiducial marks if additional information need be provided. The application of fiducial marks is discussed in greater detail with respect to FIGS. 13, 14.

As the web moves through the process line, the inspection systems of process line 74A acquire information regarding fiducial marks and anomalies using fiducial mark reader 29 and image acquisition devices 26A-26N ("image acquisition devices 26"). That is, the inspection systems will begin inspecting the web for anomalies. Although the process of collecting data is continuous (that is, the web may be constantly moving), the data collection process is described with respect to discrete segments of a web between fiducial marks for the purpose of clarity.

Analysis computer 28 detects and records anomalies with respect to the most proximate fiducial marks. Specifically, analysis computer 28 locates fiducial marks using fiducial mark reader 29 (126). That is, fiducial mark controller 30 acquires identifying information about the fiducial marks from fiducial mark reader 29 and transmits the information to analysis computer 28. Analysis computer 28, in turn, records this identifying information, along with the position of the fiducial mark on the web, in database 32 (127).

During this process, image acquisition devices 26 scan the web to produce image data useful for detecting anomalies (128). When one of image acquisition devices 26, for example, image acquisition device 26A, discovers an anomaly, the respective acquisition computer, for example, acquisition computer 27A, will inform analysis computer 28 of the presence and position of the anomaly. Analysis computer 28 will record the most recent fiducial mark, the position of the anomaly, and the distance from the fiducial mark to the anomaly in database 32 (130). In one embodiment, analysis computer 28 will adjust positional data with respect to positional data received from conversion control system 4 in order to maintain a single coordinate system for creating a composite map. In another embodiment, analysis computer 28 will utilize the coordinate system local to process 74A and conversion control system 4 will spatially register the anomaly information and form the composite map after all process lines 74 have finished processing the web, as discussed with respect to FIG. 11.

If the end of the web has not been reached ("NO" branch of 134), analysis of web roll 7 will continue as above with respect to this fiducial mark and anomalies occurring after this fiducial mark. If the end of the web has been reached, however, ("YES" branch of 134), analysis computer 28 extracts the data about anomalies in web roll 7, gathered during this inspection, from database 32 and transmit the data to conversion control system 4 (136).

Figure 11:
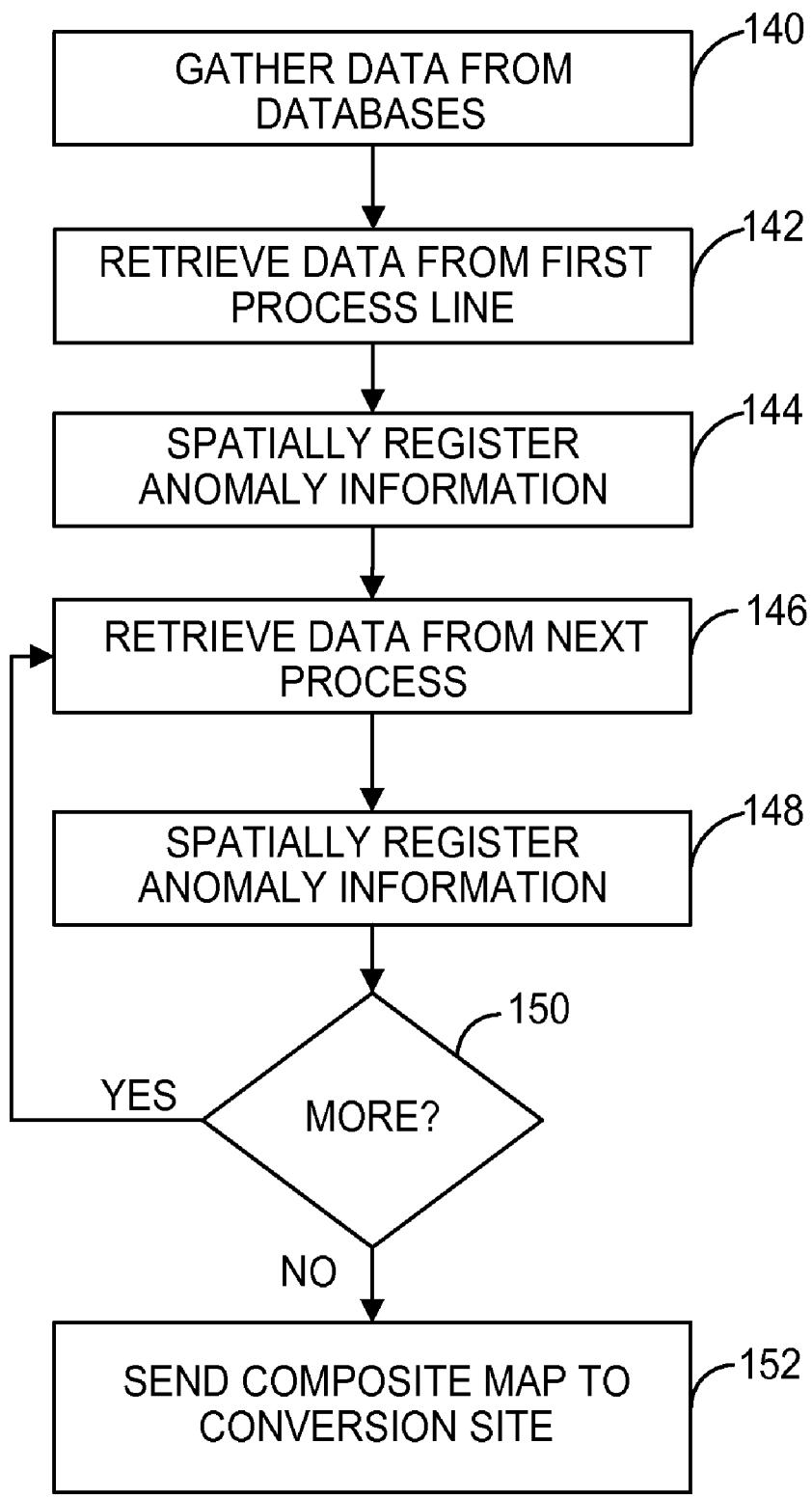
FIG. 11 is a flowchart illustrating central reconciliation of data gathered from a plurality of processes in one exemplary embodiment.

FIG. 11 is a flowchart illustrating central reconciliation of data gathered from a plurality of processes in one exemplary embodiment. In this example, it is assumed that all of process lines 74 have utilized local coordinate systems to collect data without registration. As a result, conversion control system 4 spatially registers the local anomaly information to conform to a single coordinate system. This embodiment may reduce the overhead of each of process lines 74 while collecting information from the inspection of web roll 7.

Either during the multi-process line production or after all process lines 74 have finished processing web roll 7 to produce finished web roll 10, conversion control system 4 receives the local anomaly information produced by each of process lines 74 (140). As discussed below, conversion control system 4 analyzes and converts the local anomaly information from each of process lines 74 one-by-one to register the position data to a common coordinate system. After conversion control system 4 has retrieved all of the data, it aligns the data to a composite map of the web which has its own coordinate system, which may match one or more of the coordinate systems of process lines 74.

Conversion control system 4 begins by retrieving the local anomaly information generated by the first process line, for example, process line 74A (142). This first process line may or may not be the first process line to have performed processing of web roll 7. Conversion control system 4 then spatially registers the local anomaly information from process line 74A to a target coordinate system, which may be a target coordinate system defined by conversion control system 4 or may be a coordinate system used by one of the other manufacturing processes (144). That is, conversion control system 4 processes each anomaly data entry and adjusts the position data using a translation function determined based on use of the fiducial marks within each of the process lines. In one embodiment, the retrieved data may look similar to that depicted in Table 3.

Next, conversion control system 4 retrieves the anomaly information for another one of the process lines, for instance process line 74B, used by the web (146). Process line 74B may or may not be the process line immediately subsequent to process line 74A; process line 74B may have processed web roll 7 before process line 74A, immediately after process line 74A, or after another of process lines 74. After retrieving the anomaly information from process line 74B, conversion control system 4 spatially registers the anomaly information in a similar manner (148). The spatial registration adjusts the positions of the anomaly information so as to compensate for a variety of factors, including that the web may have been trimmed or combined with another web, or may have stretched during processing, which may cause the positions of fiducial marks, and likewise anomalies, to vary from the positions recorded by other processes.

Once finished with all of the data from process line 74B, conversion control system 4 determines whether any local anomaly information for the web remains unregistered (150). If there is more anomaly information to be registered ("YES" branch of 150), then conversion control system 4 will retrieve the local anomaly information for the process (146) and spatially register the data as discussed above (148). If no more unregistered anomaly information remains, however, ("NO" branch of 150), conversion control system 4 generates a composite map based on the spatial registered anomaly information, determines a converting plan for the web roll, and sends the composite map to the converting site, for example, converting site 8A, along with the finished web roll 10. Thus converting site 8A may convert finished web roll 10 into product 12A according to the data in the composite defect map and the conversion plan.

Figure 12:
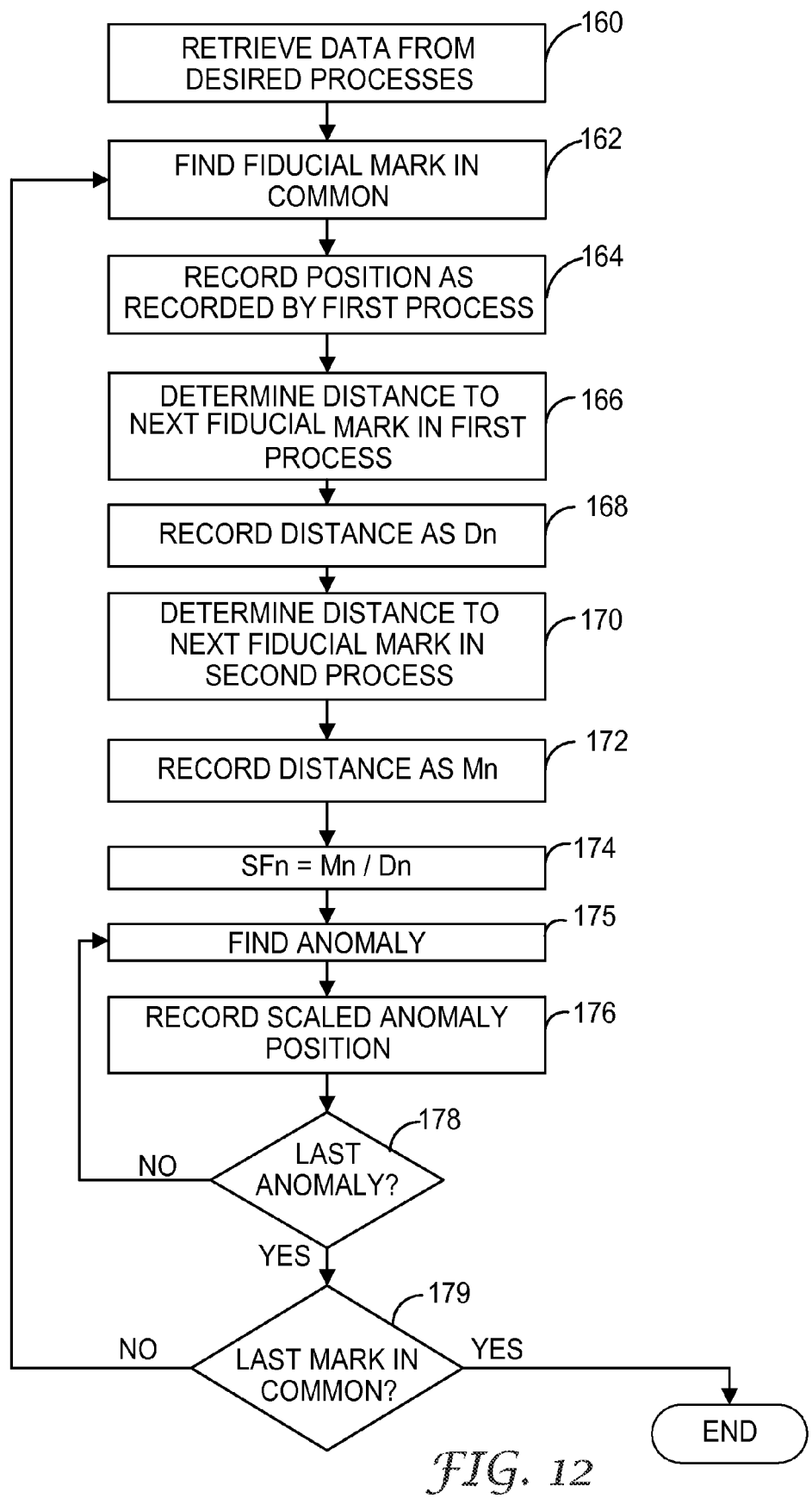
FIG. 12 is a flowchart illustrating the steps for reconciling the data gathered from a plurality of processes in an exemplary embodiment.

FIG. 12 is a flowchart illustrating operations for performing a linear transformation on position data collected from two different process lines, for example, process lines 74A and 74B. Although discussed with respect to conversion control system 4, analysis computer 28 may also perform linear transformation of data collected by the current process line. Conversion control system 4 may need to perform a linear transformation on the data collected from multiple process lines for a number of reasons, including because the web may have stretched during processing or for other reasons.

Generally, a linear transformation is used to map data from one coordinate system onto a different coordinate system. In this example, anomaly positions are linearly transformed from the coordinate system of process line 74B to fit the coordinate system of process line 74A. A distinct linear transformation may be performed for each portion of web between two fiducial marks.

First, conversion control system 4 retrieves relevant data from both process lines 74A and 74B (160). Conversion control system 4 ensures that the data from both process lines 74A and 74B is considered as oriented along the web in the same direction. This may be necessary due to the nature of a web roll being wound and unwound, i.e., that a given process may begin with either end of the web depending on where the process falls within the recipe. Conversion control system 4 may determine the direction of the data according to the fiducial mark data. If the data direction does not match, conversion control system 4 may logically reverse the direction of one of the two process lines such that the data direction matches. In one example, conversion control system 4 reverses the direction by offsetting the data from the end of the web roll rather than the beginning as may occur in the forward case.

After ensuring that the data is flowing in the same direction for each process, conversion control system 4 processes the data to locate a first fiducial mark in common between process lines 74A and 74B (162). Conversion control system 4 records the position of this mark as recorded by process line 74A (164). Conversion control system 4 then locates the position of the next fiducial mark as recorded by process line 74A (166). Conversion control system 4 records the difference between the two fiducial marks as $D_n$ (168). Next, conversion control system 4 finds the position of the next fiducial mark within the data recorded by process line 74B (170) and records the difference between the mark and the previous mark within the data of process line 74B as the difference $M_n$ (172).

Conversion control system 4 uses the differences $D_n$ and $M_n$ to create a scaling factor $SF_n$ for each data point between the two fiducial marks, such that $SF_n = M_n/D_n$ (174). Conversion control system 4 then processes the local anomaly information for process 74B to determine locate any anomaly positions which need to be scaled (175). For each anomaly data point recorded by process line 74B, conversion control system 4 uses the scaling factor $SF_n$ to transform each data point into the coordinate system or process line 74A. To do so, the distance from the fiducial mark to the anomaly is recorded as $IP_j$. This distance is "scaled" by determining $SD_j = IP_j * SF_n$. Then, to locate the new, adjusted position $AP_j$ on the common coordinate system, conversion control system 4 adds the scaled distance $SD_j$ to the position of the fiducial mark as recorded by process line 74B (176). Conversion control system 4 adjusts the position of each anomaly between these two fiducial marks in this manner (178). Conversion control system 4 then finds the next fiducial mark in common and repeats the process until no more fiducial marks are in common (179).

Once all anomalies between these two fiducial marks have been adjusted, conversion control system 4 determines whether it has reached the end of the data gathered for either process lines 74A and 74B (180). If both have more data to analyze ("NO" branch of 180), conversion control system 4 will find the position of the next fiducial mark as recorded by each of process lines 74A and 74B and transform the anomaly data according to the method above. However, if the end of the data has been reached for either process line (which may be possible due to a web being split, combined with another web, or for other reasons) ("YES" branch of 180), conversion control system 4 has finished linearly transforming this set of data, so conversion control system 4 continues with other processing, either linearly transforming a new pair of process lines 74, combining data from process lines 74, or transmitting data to one of converting sites 8.

In some embodiments, a modeling engineer may generate one or more mathematical models for the manufacturing operations performed on the web throughout the plurality of manufacturing process lines. During operation, data from the mathematical models may be used to spatially register the position data for the different manufacturing process lines. For example, a linear or nonlinear transformation may be applied to spatially register the position data for each of the anomalies, wherein the transformation is calculated using previously generated mathematical models of the web process for the web region of interest.

Figure 13:
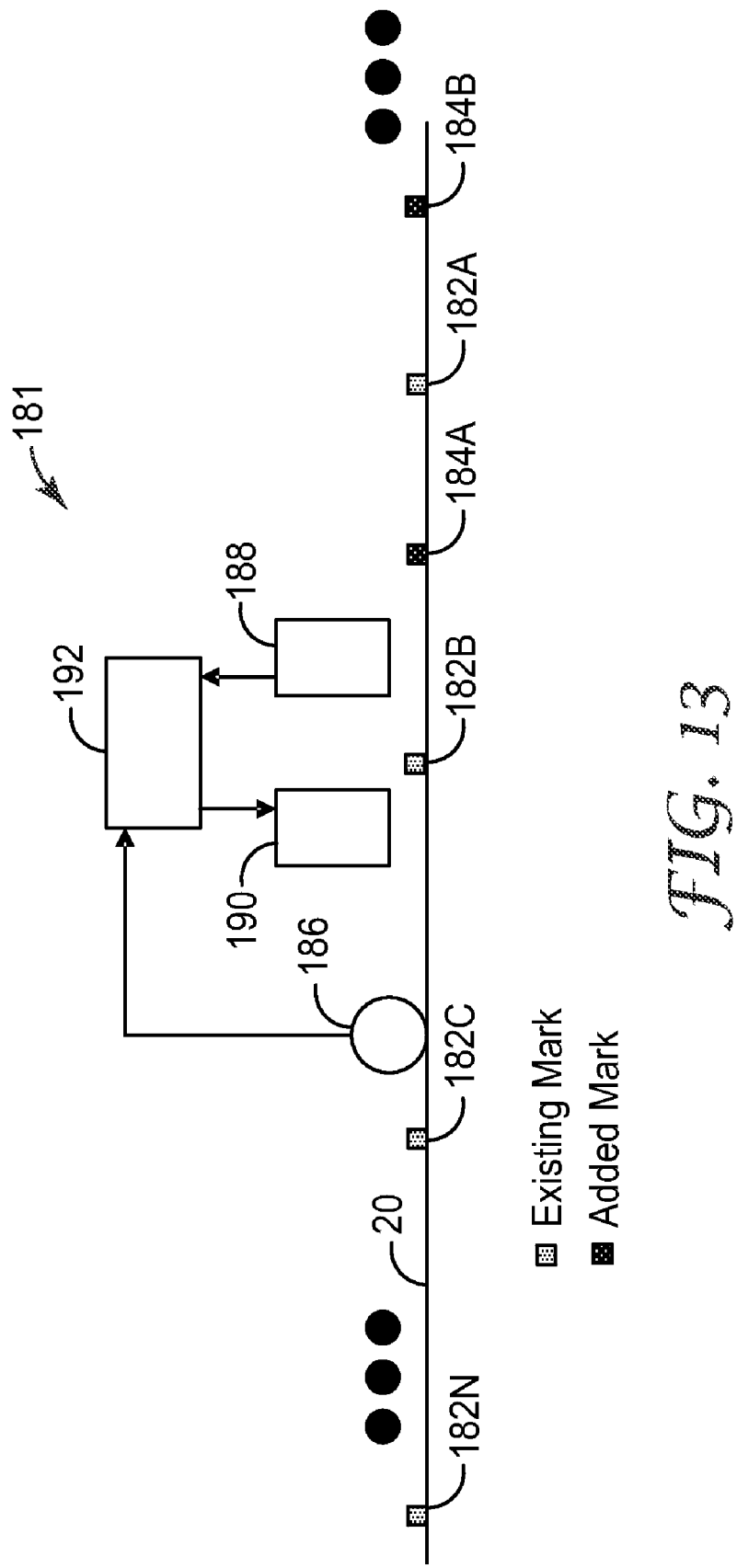
FIG. 13 is a block diagram illustrating an exemplary embodiment of fiducial mark writer.

FIG. 13 is a block diagram illustrating an exemplary embodiment of fiducial mark writer 181. In some embodiments, process line 74A may include fiducial mark writer 181 for application of original or supplemental fiducial marks. In the exemplary embodiment of fiducial mark writer 181, fiducial mark writer 181 comprises encoder 186, reader 188, writer 190, and trigger module 192. Fiducial mark writer 181 is typically positioned such that writer 190 is near the edge of web 20 such that fiducial marks will be written outside of the salable area of web 20. Fiducial mark writer 181 can write an initial set of fiducial marks to a web which has no fiducial marks. Fiducial mark writer 181 can also rewrite fiducial marks to a web which has one or more corrupted fiducial marks. Fiducial mark writer 181 can also interlace a new set of fiducial marks between an existing set of fiducial marks. That is, fiducial mark writer 181 is able to apply a new set of fiducial marks to web 20 such that the new set does not corrupt the existing set. Fiducial mark writer 181 may utilize either of the exemplary fiducial mark embodiments depicted in FIGS. 5A-5B, or fiducial mark writer 181 can be modified to write a different embodiment of a fiducial mark.

FIG. 13 depicts web 20 with a set of existing fiducial marks 182A-182N ("existing fiducial marks 182"). That is, existing fiducial marks 182 were applied to web 20 at some earlier stage of the development of web 20. FIG. 13 depicts fiducial mark writer 181 as interlacing a set of new fiducial marks 184A-184B ("new fiducial marks 184") between existing fiducial marks 182. However, fiducial mark writer 181 is capable of applying a set of new fiducial marks 184 to web 20 without a set of existing fiducial marks 182. The determination of where to write a new fiducial mark is discussed in greater detail with respect to FIG. 15.

In an exemplary embodiment, encoder 186 comprises a wheel pressed firmly against the surface of web 20. Encoder 186 may transmit an encoder pulse for each partial revolution of the wheel to trigger module 192. Trigger module 192 can measure the distance along web 20 according the number of encoder pulses and the circumference of the wheel of encoder 186. For example, if the wheel is ten centimeters in circumference and encoder 186 gives an encoder pulse every hundredth of a rotation, then after fifty encoder pulses trigger module 192 can determine that the web has traveled five centimeters. In this way, trigger module 192 can measure the distance web 20 has traveled extremely accurately.

Reader 188 may be very similar to the fiducial mark reader as depicted in FIG. 6. In the exemplary embodiment of fiducial mark writer 181, reader 188 reads existing fiducial marks 182 and communicates information read from existing fiducial marks 182 to trigger module 192. Trigger module 192, utilizing distance information obtained from encoder 186, can thus determine the position of existing fiducial marks 182 to a high degree of accuracy by being configured with the distance between encoder 186 and reader 188.

Trigger module 192 may instruct printer 190 to write a new fiducial mark, for example, new fiducial mark 184A, onto the surface of web 20. Reader 188 may read the newly applied fiducial mark, e.g. new fiducial mark 184A, once new fiducial mark 184A passes under reader 188. Trigger module 192 may record position information about newly written fiducial marks 184 as well. In one embodiment, printer 190 comprises an inkjet printer. Printer 190 may comprise any device capable of applying a fiducial mark to web 20. For example, printer 190 may comprise a laser printer or a device to secure mechanical or magnetic labels to web 20.

Figure 14A:
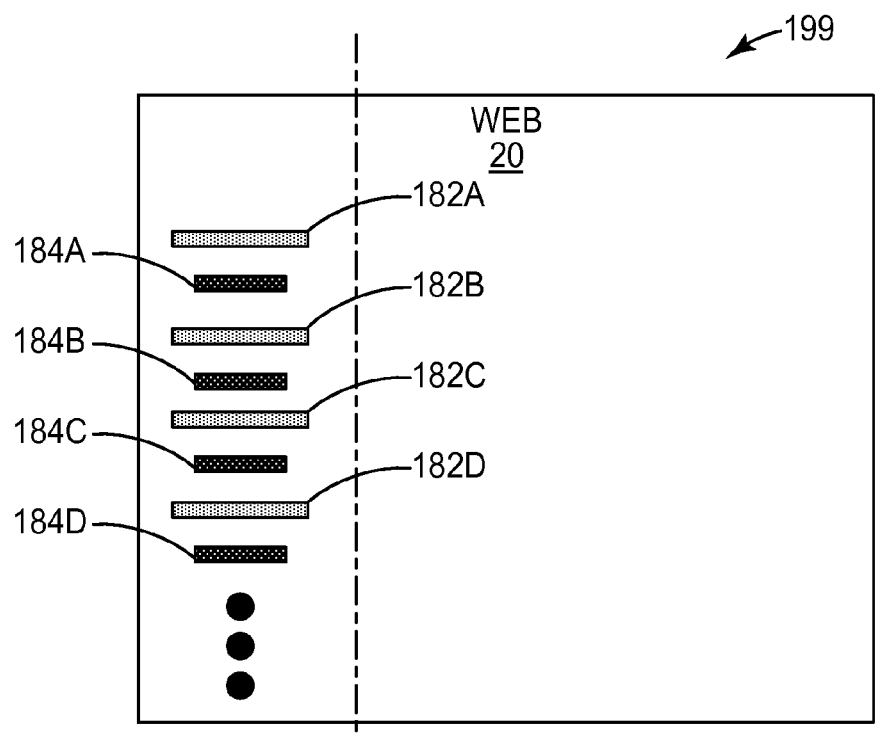
FIGS. 14A-14D are block diagrams illustrating the positions of existing and inserted fiducial marks.

FIGS. 14A-14D are block diagrams illustrating the positions of existing and inserted fiducial marks. FIG. 14A illustrates an example wherein new fiducial marks 184 are interlaced between a full set of existing fiducial marks 182. In this example, web 20 has a set of existing fiducial marks 182. As shown in FIG. 14A, fiducial marks may be near the edge of the web outside of salable area 199 (bounded by a vertical dashed line running parallel to the web and fiducial marks in FIG. 14). Each of existing marks 182, for example existing mark 182A and existing mark 182B, may be spaced at approximately the same distance apart. In one embodiment, this distance may be about 2 meters. New fiducial marks may be inserted, for example, in accordance with the method described with respect to FIG. 15. Suitable fiducial marks for either or both of new fiducial marks 184 and existing fiducial marks 182 are depicted in FIG. 5.

Figure 14B:
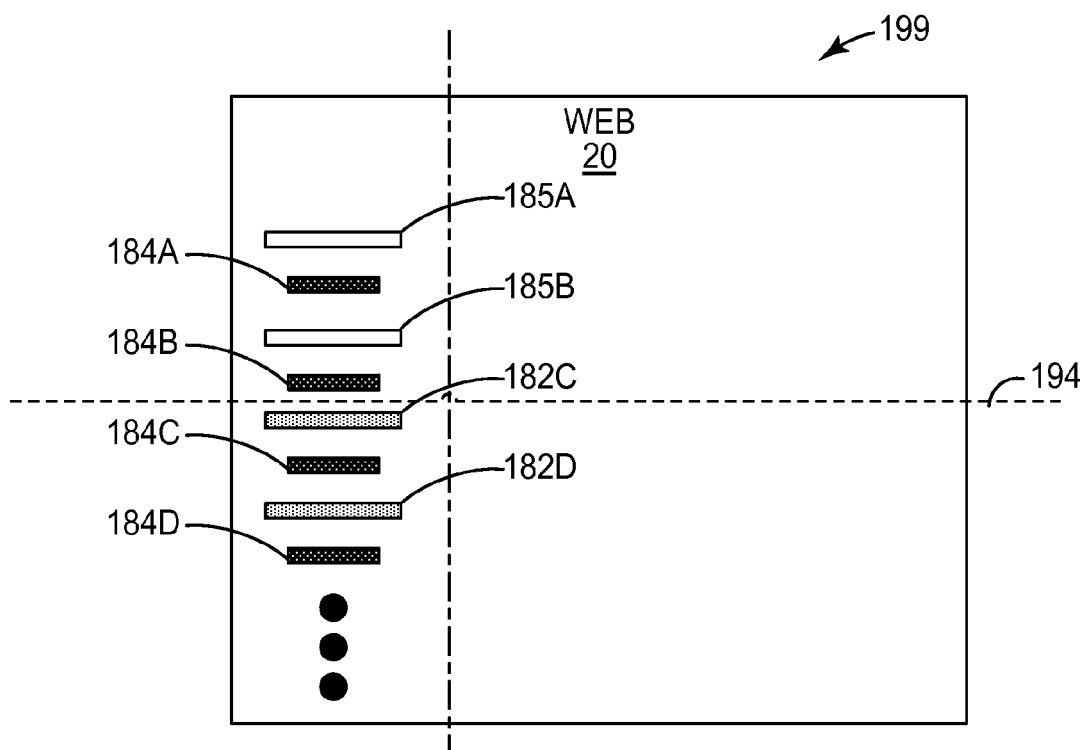

FIG. 14B illustrates an example wherein web 20 has a set of existing fiducial marks 182, but the existing set begins late. That is, there is a space on web 20 from the start of the web to some point 194 down web 20 where the space does not have existing fiducial marks, but from point 194 on, web 20 does have existing fiducial marks 182. FIG. 14B depicts these void spaces as void spaces 185. In one embodiment, for example as discussed with respect to FIG. 15, fiducial mark writer 181 may apply new fiducial marks 184 to spaces between existing fiducial marks 182. In another embodiment fiducial mark writer 181 may in addition apply new fiducial marks to void spaces 185 where fiducial marks should have been present. One may operate fiducial mark writer 181 so as to fill void spaces 185 with marks in a distinct format from new fiducial marks 184. That is, fiducial mark writer 181 may utilize a different format of fiducial marks for filling void spaces 185 than the format used for adding new fiducial marks 184. The format of the fiducial marks for filling void spaces 185 may be calibrated so as to match the format of existing fiducial marks 182. In another embodiment, the format of the fiducial marks for filling void spaces 185 may be the same as the format of new fiducial marks 182. In yet another embodiment, fiducial mark writer 181 will not write any fiducial marks in void spaces 185 but only apply new fiducial marks 184.

Figure 14C:
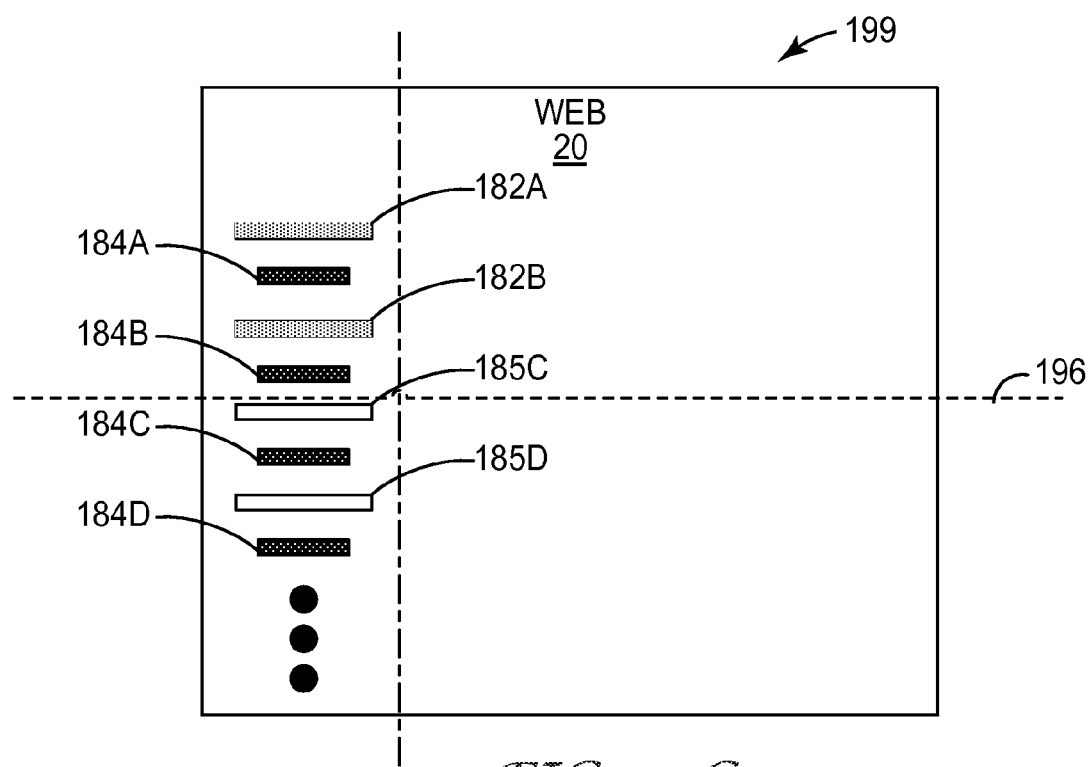

FIG. 14C illustrates an example wherein web 20 has a set of existing fiducial marks 182, but the existing set ends early. That is, there is a space on web 20 from the start of the web to some point 196 down web 20 where the space has existing fiducial marks 182, but from point 196 on, there are no existing fiducial marks. FIG. 14C depicts these void spaces as void spaces 185. In one embodiment, for example as discussed with respect to FIG. 15, fiducial mark writer 181 may apply new fiducial marks 184 to spaces between existing fiducial marks 182, and in addition fiducial mark writer 181 may also apply new fiducial marks to void spaces 185 where fiducial marks should have been present. Again, the format of the fiducial marks for filling void spaces 185 may match the format of existing marks 182 or the fiducial marks for filling void spaces 185 may match new fiducial marks 184.

Figure 14D:
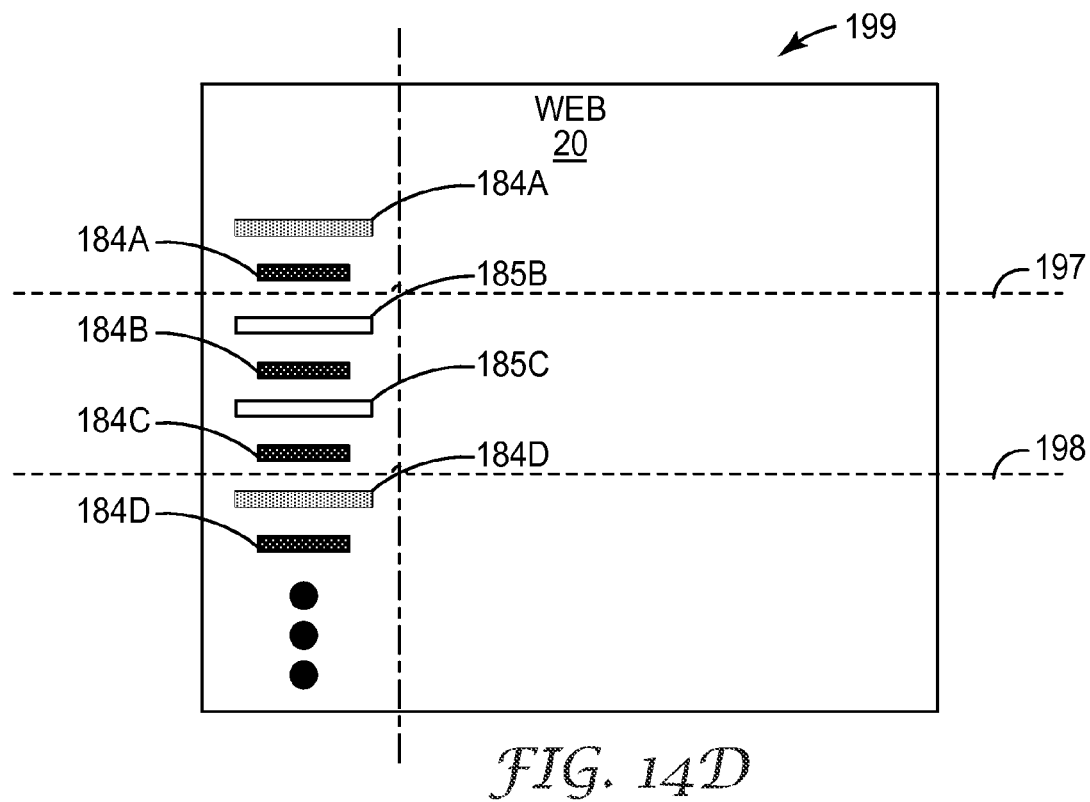

FIG. 14D illustrates an example wherein web 20 has a set of existing fiducial marks 182, but there is a gap in the set. That is, there is a space on web 20 between two points 197, 198, wherein web 20 has existing fiducial marks 182 from the start of the web to point 197, and from point 198 to the end of the web, web 20 has existing fiducial marks 182, yet between points 197 and 198, web 20 has void spaces rather than existing fiducial marks. FIG. 14D depicts these void spaces as void spaces 185. In one embodiment, for example as discussed with respect to FIG. 15, fiducial mark writer 181 may apply new fiducial marks 184 to spaces between existing fiducial marks 182, and in addition fiducial mark writer 181 may also apply new fiducial marks to void spaces 185 where fiducial marks should have been present. Again, the format of the fiducial marks for filling void spaces 185 may match the format of existing marks 182 or the fiducial marks for filling void spaces 185 may match new fiducial marks 184.

FIG. 15 is a flowchart illustrating exemplary operations involved in application of fiducial marks to a web. FIG. 15 depicts an example method by which fiducial mark writer 181 may apply new, interlaced fiducial marks to a web as an example method by which fiducial mark writer 181 may apply fiducial marks to void spaces, that is, spaces where fiducial marks should exist but do not. FIG. 15 also depicts an example method by which fiducial mark writer 181 may apply a set of fiducial marks to a web which has no existing fiducial marks.

First, web 20 must be in place and ready for marking (FIG. 2). At this time, fiducial mark writer 181 is activated (200). Concurrently, web 20 is wound off of a supporting roll and collected onto supporting roll, causing web 20 to travel past fiducial mark writer 181. In response to detecting a leading edge of the web, trigger module 192 initializes a distance counter D to zero (202). In addition, trigger module 192 initializes a global variable FD to represent the fixed distance between fiducial marks. In one embodiment, trigger module 192 presumes that FD is two meters unless it receives contrary instructions from an operator. Trigger module 192 also maintains a position offset variable PO which represents the distance between reader 188 and printer 190.

When web 20 has existing fiducial marks 182, reader 188 sends a fiducial pulse to trigger module 192 when reader 188 detects a fiducial mark. As long as a fiducial pulse has not occurred ("NO" branch of 204), the fiducial writer will continue to wait for a fiducial pulse. Once a fiducial pulse occurs ("YES" branch of 204), trigger module 192 will initialize a new counter N to zero and distance D to zero (206). Trigger module 192 will then enable the new counter N (208), then wait for an encoder pulse from encoder 186 (210), and will continue to wait as long as an encoder pulse has yet not occurred ("NO" branch of 210).

Once an encoder pulse occurs ("YES" branch of 210), however, the fiducial writer will increment N by 1 (that is, N=N+1) (212). Trigger module 192 will then determine whether N is equal to FD/2 (214); if not ("NO" branch of 214), trigger module 192 will wait for a new encoder pulse. If N is equal to FD/2, however, ("YES" branch of 214), trigger 192 will disable the "new" counter (216) and instruct printer 188 to print a new fiducial mark, for example, new fiducial mark 184B (218). In other words, trigger module 192 will instruct printer 188 to print a new fiducial mark half-way between existing fiducial marks. Trigger module 192 will then prepare to print the next fiducial mark by disabling the fiducial present sensor input gate for a distance of (3*PO)/2 (228). Those skilled in the art are capable of modifying the above instructions to print new fiducial marks 184 at other intervals and positions; for example, one could modify the above instructions to print new fiducial marks 184 at one-quarter of the distance between existing fiducial marks 182.

When web 20 has existing fiducial marks 182 but is missing a certain mark, for instance, if existing fiducial mark 182C has been corrupted, fiducial mark writer 181 can replace fiducial mark 182C. Trigger module 192 will be expecting a fiducial pulse but will not receive one, as fiducial mark 182C is corrupted. Therefore, trigger module 192 will use distance counter D to measure a distance FD from the previous fiducial pulse to where existing fiducial mark 182C should be located (220, 222, 224). At this point, trigger module 192 will instruct writer 190 to write fiducial mark in the correct position (226). Trigger module 192 will again prepare to print the next fiducial mark by disabling the fiducial present sensor input gate for a distance of (3*PO)/2 (228).

When web 20 has no existing fiducial marks 182, or when web 20 has a set of existing fiducial marks 182 as well as void spaces 185 as shown in FIG. 14, fiducial mark writer 181 may determine when to print a new fiducial mark in a slightly different way. Initially, trigger module 192 will initialize distance counter D to zero (202). As there are no existing fiducial marks 182, trigger module 192 will never receive a fiducial pulse ("NO" branch of 204), so trigger module 192 will wait for an encoder pulse from encoder 186 (220). Once an encoder pulse occurs ("YES" branch of 220), trigger module 192 will increment D (that is, D=D+1) (222). Trigger module 192 will then determine whether D is equal to FD (224). If not ("NO" branch of 224), trigger module 192 will wait for a new encoder pulse and continue to increment D. If D is equal to FD, however ("YES" branch of 224), trigger module 192 will instruct printer 188 to print a new fiducial mark, for example, new fiducial mark 184B (226). Trigger module 192 will then reinitialize D to zero (202) and start over again. In other words, when no fiducial marks are present, printer 188 will print new fiducial marks 184 at a distance of FD apart. In one embodiment, fiducial mark writer 181 prints new fiducial marks 184 at a distance of 2 m apart.

Using this exemplary method, fiducial mark writer 181 is able to either write new fiducial marks 184 to a web without requiring any existing fiducial marks 182, interlace new fiducial marks 184 between existing fiducial marks 182, or even replace a missing fiducial mark.

Figure 16:
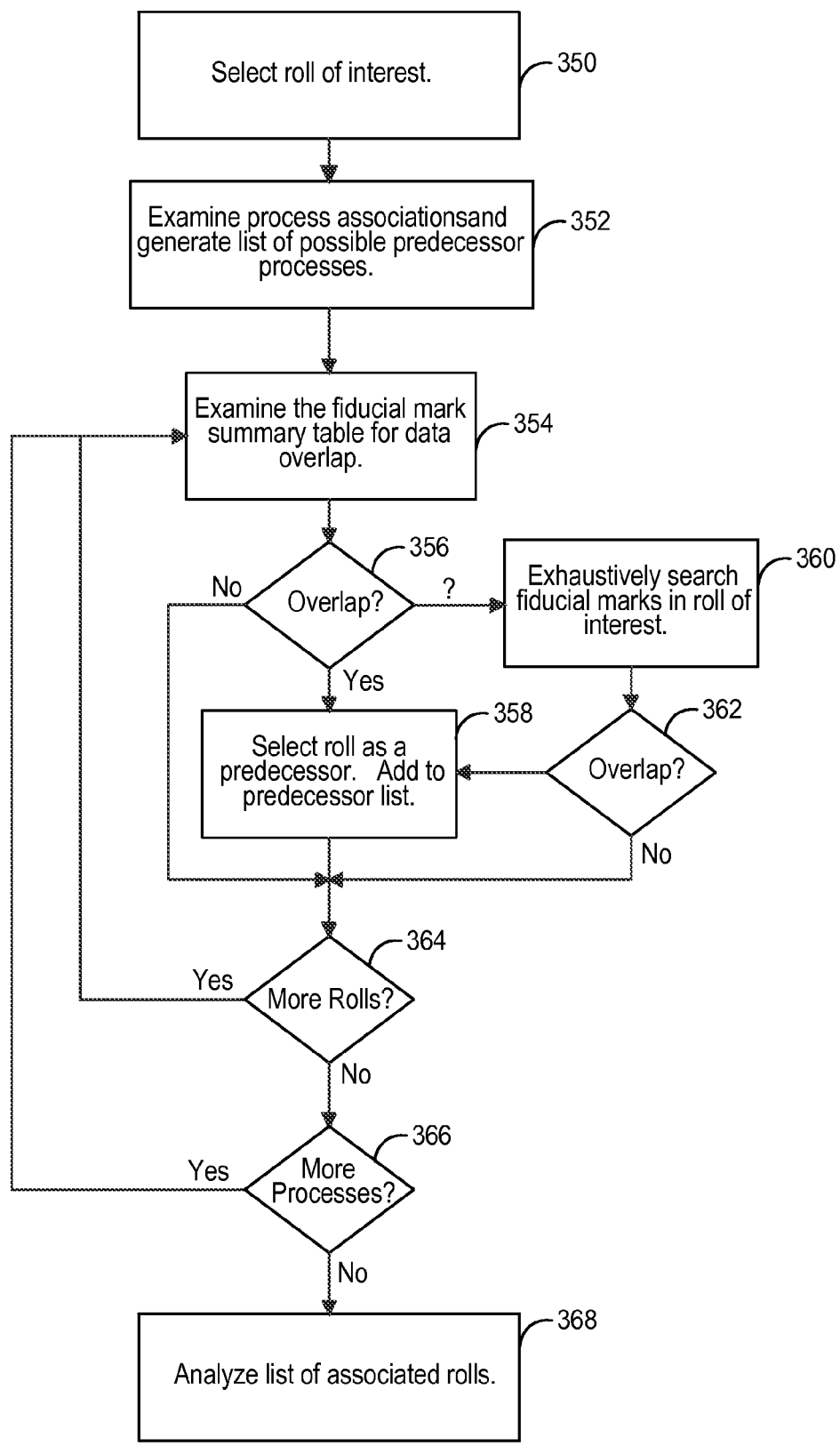
FIG. 16 is a flowchart illustrating exemplary operations involved in identifying spatially synchronized areas of web material throughout multiple manufacturing operations.

FIG. 16 is a flowchart illustrating exemplary operations involved in identifying areas of web material for a given web roll segment that have been processed throughout multiple manufacturing operations and, therefore, are candidates for spatially synchronization. In one embodiment, conversion control system 4 uses fiducial marks to identify various web rolls 7, 10. That is, conversion control system 4 may identify segments of a particular web roll 7, 10 that have been through common manufacturing processes 74 by identifying overlapping fiducial marks from each of the processes that are present on the web roll. In one embodiment of conversion control system 4 uses the example method depicted in FIG. 16 to create a correspondence between data collected from a sequence of the various processes 74 for a particular web roll segment.

First, a particular web roll 10 of interest is selected (350). Typically a user may select a web roll 10 or a portion thereof through a graphical user interface ("GUI") presented by conversion control system 4. However, in other embodiments, other devices may interface with conversion control system 4 to automatically or semi-automatically select a web roll and retrieve data from conversion control system 4. Conversion control system 4 may also permit accessing data collected for unfinished web rolls 7 and in-process web rolls, in addition to final web rolls 10.

Once conversion control system 4 has a particular web roll for which to gather data, conversion control system 4 may begin to search for data gathered by the various processes 74 and collected by consolidation servers 76. Conversion control system 4 then identifies a complete set of possible predecessor processes 74 that may be associated with the web roll (352). For example, conversion control system 4 may identify a most recent processes 74 for a particular web roll and then recursively identify possible predecessor processes 74 to create a tree-like logical construct representing the potential processing history of the web roll. In one embodiment, conversion control system 4 may exhaustively search for data corresponding to the web roll. In another embodiment, conversion control system 4 may use the method described with respect to FIG. 17 below to reduce the search space in which conversion control system 4 will query for data corresponding to the selected web roll.

After conversion control system 4 has assembled the search space for data associated with the web roll, conversion control system 4 may search for data associated with the web roll (354). Specifically, conversion control system 4 may search for fiducial marks that match fiducial marks of the web roll of interest within the data from each of the processes in the search space. Conversion control system 4 may also search an entire roll for specific segments of the roll, defined by a certain range of fiducial marks (for example, segments 376A, 376B, FIG. 18B). Conversion control system 4 may search for overlapping fiducial marks among the processes that form a segment of the web roll (356). In one embodiment, if conversion control system 4 cannot determine whether overlap exists ("?" branch of 356), e.g. due to gaps in the data of the web roll data being triggered (see Table 5, below), then conversion control system 4 will exhaustively search all of the data (360) to look for overlap (362), rather than using an optimized method, such as the method discussed with respect to FIG. 17. If no overlap exists for a particular segment ("NO" branch of 356 or "NO" branch of 362), conversion control system 4 will search for the next web roll segment. If overlap does exist ("YES" branch of 362 or "YES" branch of 356), conversion control system 4 will record data associated with the roll with the overlapping fiducial marks data from a predecessor roll for the web roll of interest selected at step 350.

Conversion control system 4 continues to search if more roll segments exist on the web roll of interest (364). Once conversion control system 4 has finished searching all of the roll segments associated with a particular process, conversion control system 4 will select a next process based on the process list generated at step 354 (366).

After conversion control system 4 has gathered the data, conversion control system 4 may analyze the data (368). Conversion control system 4 may search for and identify all segments of web with overlapping fiducial marks for each process. Briefly referring to the example of FIG. 18A, conversion control system 4 may identify roll segments 376A and 376B, each of which contain web roll segments common to the three processes Process A, Process B, and Process C. Conversion control system 4 may then adjust the data according to the segments and align the data such that the data is usable for analysis to, for example, mark anomalies and/or defects on the surface of the web, or to analyze the processes to determine where anomalies or defects are being introduced so that the processes may be adjusted or corrected.

Figure 17:
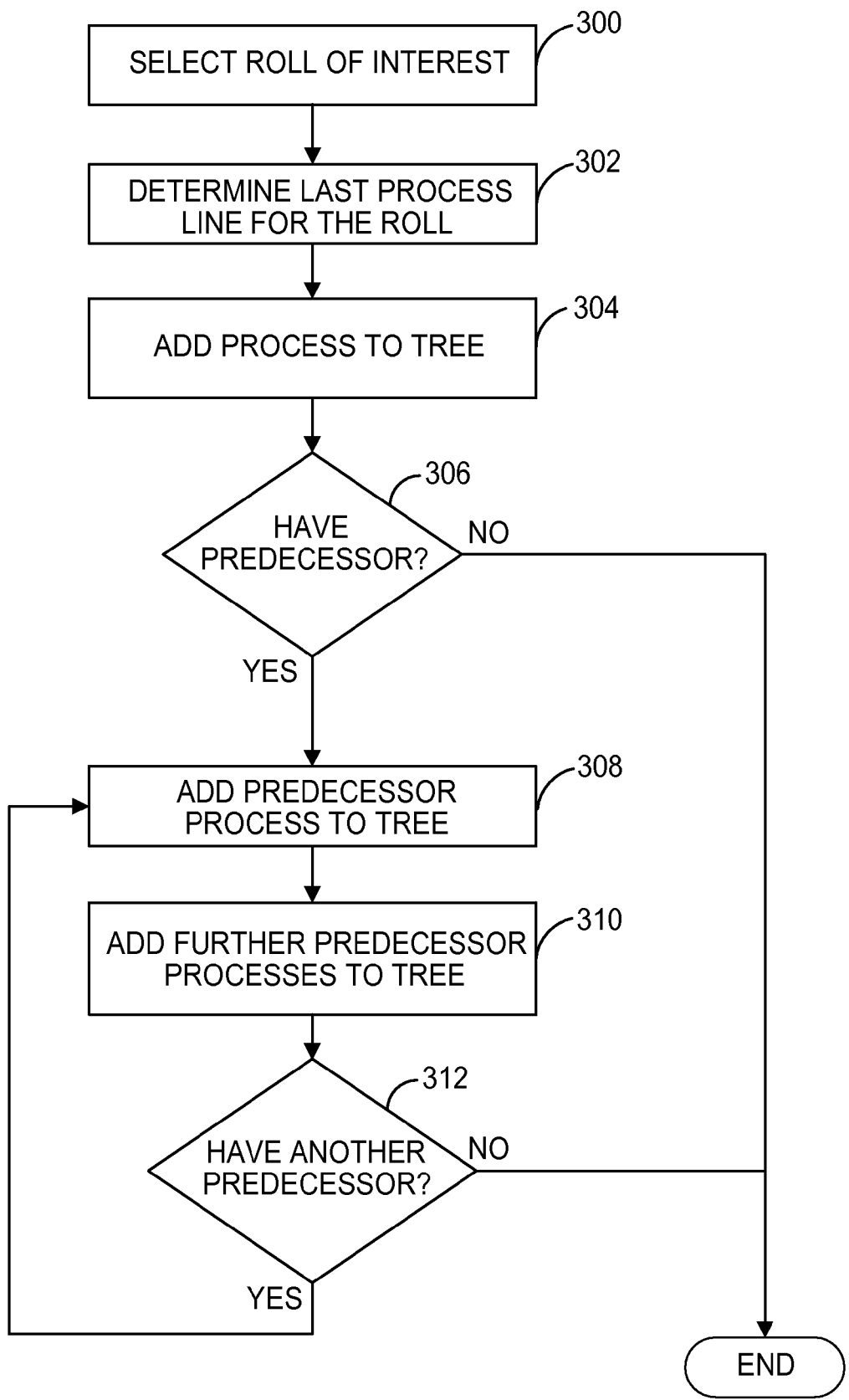
FIG. 17 is a flowchart illustrating exemplary operations involved in reducing search space of data associated with particular web rolls.

FIG. 17 is a flowchart illustrating exemplary operations involved in determining the search space of data associated with particular web rolls 7, 10. In one embodiment, conversion control system 4 uses the example method depicted in FIG. 17 to improve the performance of locating potential processes 74 that may have collected data associated with particular web rolls 10. Conversion control system 4 may, for example, use product and process constraints that occur due to the nature of the constraints to reduce the search space when retrieving data relevant to a particular web roll 10.

As an example, film making operations cannot have predecessor roll operations. To make use of these process constraints, one may assemble a "process association map" that describes the possible interactions between various manufacturing processes 74. The process association map may describe, for example, possible predecessor processes for each of processes 74. Table 4 shows an example process association map.

data could exist for the web roll, as no process could have preceded the most recently analyzed process.

If there could have been a predecessor process, however, ("YES" branch of 306), conversion control system 4 selects one of the predecessor processes (308). Conversion control system 4 may then essentially perform a recursive instance of the method portrayed in FIG. 17, except that in the recursive instance the web roll of interest is already selected. That is, conversion control system 4 may determine whether this predecessor process itself has any predecessors and add them to the tree as one branch from the root (310).

Next, conversion control system 4 determines whether any more predecessor processes exist for the currently selected process (312). If not ("NO branch of 312) then the method may end. However, if there are more possible predecessor processes ("YES" branch of 312), conversion control system 4 will perform the recursion for each of the predecessor processes for the current process and add each of them as respective branches to the root of the tree.

Table 5 below presents an example data set for multiple processes that conversion control system 4 may analyze and optionally present to a user. Table 5 includes fields Roll Name, First, Last, Min, Max Expected #, Actual #, and Comments. Roll Name is the name of a roll segment for a particu-

TABLE 4

| Plant A | Plant B | Plant C | Plant D |
| --- | --- | --- | --- |
| Process A1 | Process B1 | Process C1 | Process D1 |
| Possible Predecessors: none | Possible Predecessors: Plant A, Process A1 Plant A, Process A2 Plant A, Process A3 Plant A, Process A4 Plant C, Process C1 Plant D, Process D2 | Possible Predecessors: Plant A, Process A2 Plant A, Process A5 Plant D, Process D1 | Possible Predecessors: none |
| Process A2 | Process B2 | | Process D2 |
| Possible Predecessors: none | Possible Predecessors: Plant A, Process A1 Plant A, Process A2 Plant A, Process A3 Plant A, Process A4 Plant C, Process C1 Plant D, Process D2 | | Possible Predecessors: Plant A, Process A2 Plant A, Process A3 Plant B, Process B3 Plant C, Process C1 |
| Process A3 | Process B3 | | |
| Possible Predecessors: none | Possible Predecessors: Plant A, Process A5 Plant C, Process C1 | | |
| Process A4 | | | |
| Possible Predecessors: none | | | |
| Process A5 | | | |
| Possible Predecessors: none | | | |

Conversion control system 4 may first select a particular web roll of interest (300), i.e., a web roll for which conversion control system 4 requires data. Conversion control system 4 then determines the last one of processes 74 to have performed operations on the web roll (302). Next, conversion control system 4 adds the process to a hierarchically arranged set of nodes that may form a tree structure, wherein the last process may occupy the root of the tree (304). Conversion control system 4 may then determine whether the last process has any predecessor processes (306). If not ("NO" branch of 306), then there is no reason to continue, because no more lar process. First is the fiducial mark with smallest associated distance in the local coordinate system of the process. Last is the fiducial mark with largest associated distance in the local coordinate system of the process. Min is the fiducial mark with the smallest value. Max is the fiducial mark with the largest value. Expected # is the expected number of fiducial marks of the roll, equal to (Max−Min+1). Actual # is the actual number of fiducial marks on the roll as determined by the process or process inspection system. The comments field describes aspects or status information of the roll, such as potential flaws such as data gaps.

TABLE 5

| | Fiducial Marks | | | | | | |
|---|---|---|---|---|---|---|---|
| Roll Name | First | Last | Min | Max | Expected # | Actual # | Comments |
| AIS1-0001 | 1 | 144 | 1 | 144 | 144 | 144 | forward |
| AIS1-0002 | 192 | 490 | 192 | 490 | 299 | 299 | forward |
| AIS2-0001 | 762 | 952 | 762 | 952 | 191 | 191 | forward |
| AIS3-0011 | 1210 | 1400 | 1210 | 1400 | 191 | 191 | forward |
| BIS2-0007 | 143 | 86 | 86 | 143 | 58 | 58 | reverse |
| BIS2-0008 | 81 | 1 | 1 | 81 | 81 | 81 | reverse |
| BIS2-0009 | 475 | 350 | 350 | 475 | 126 | 126 | reverse |
| BIS2-0010 | 333 | 163 | 163 | 333 | 171 | 171 | reverse |
| BIS2-0011 | 155 | 32 | 32 | 155 | 124 | 124 | reverse |
| BIS3-0125 | 1400 | 1222 | 1222 | 1400 | 179 | 179 | reverse |
| CIS1-0003 | 88 | 140 | 88 | 140 | 53 | 53 | forward |
| CIS2-0001 | 6 | 472 | 6 | 472 | 467 | 197 | forward, data gap |
| CIS3-0001 | 164 | 155 | 33 | 321 | 289 | 280 | discontinuity, data gap? |
| CIS3-0002 | 951 | 779 | 779 | 951 | 173 | 173 | reverse |
| CIS3-0003 | 1225 | 1391 | 1225 | 1391 | 167 | 167 | forward |

To determine whether data for the selected process is associated with the particular web roll, conversion control system 4 uses the fiducial marks of the web roll. If a successor process has not or cannot join two rolls, conversion control system 4 may look for overlap in the fiducial marks between the two processes. If a successor process may have joined two rolls, conversion control system 4 compares the expected fiducial mark and the actual fiducial mark. If the expected fiducial mark count and the actual fiducial mark count differ by a certain percent, conversion control system 4 may determine that a gap exists in the data and will exhaustively search the data. In one embodiment, the certain percent is a five percent difference in the expected fiducial mark count ("Expected #") and the actual fiducial mark count ("Actual #"). If conversion control system 4 determines that First is not equal to either Min or Max, or Last is not equal to either Min or Max, conversion control system 4 may also determine that a data gap exists and will exhaustively search the data. Otherwise, conversion control system 4 may proceed with the optimized search method described herein.

As one example operation of the method, the processes may conform to the hierarchy portrayed in Table 4 above. The last process for a particular web roll may have been process D1 of plant D. In this case, conversion control system 4 will gather all data from process D1 and end, as there are no possible predecessors for process D1.

As another example operation of the method, the processes may again conform to the hierarchy portrayed in Table 4 above. The last process for a particular web roll may have been process D2 of plant D. In this case, conversion control system 4 will gather all data from process D2. Conversion control system 4 will then gather data from each of processes A2 and A3 of plant A related to the web roll. Conversion control system 4 may then gather data from process B3 of plant B. Process B3 itself has possible predecessors A5 and C1, so conversion control system 4 will gather data from processes A5 and C1. Process C1 has predecessor processes A2, A5, and D1. Thus, conversion control system 4 will gather data related to the web roll from each of A2, A5, and D1, none of which has any predecessor processes. Next, conversion control system 4 will gather data from process C1 again, as process C1 is a predecessor to D2 (as well as to process B3). Therefore, conversion control system 4 will gather data from processes A2, A5, and D1.

This method may provide several advantages. For example, the method may reduce the time required to search for data related to a particular web roll or web roll segment. The operating time of searching for data related to a web roll according to the example embodiment of the improved method described with respect to FIG. 17 may be a logarithmic function of the number of processes 74 present in the system, as opposed to being directly related to the number of processes 74 present in the system. That is, conversion control system 4 may create a depth-first search tree from the processes for which a significant number of branches may be pruned to perform the search, as opposed to exhaustively searching for data. Those skilled in the art will recognize that, for the timing functions Big-Theta ($\Theta$), which describes both upper and lower bounds, Big-Oh (O), which describes upper bounds, and Big-Omega ($\Omega$), which describes lower bounds, this method may change the run time from $\Theta(n^*m)$, where "n" is the number of processes and "m" is the maximum amount of data stored for any one process, to $O(n^*m)$ and $\Omega(m^*\log(n))$.

Figure 18A:
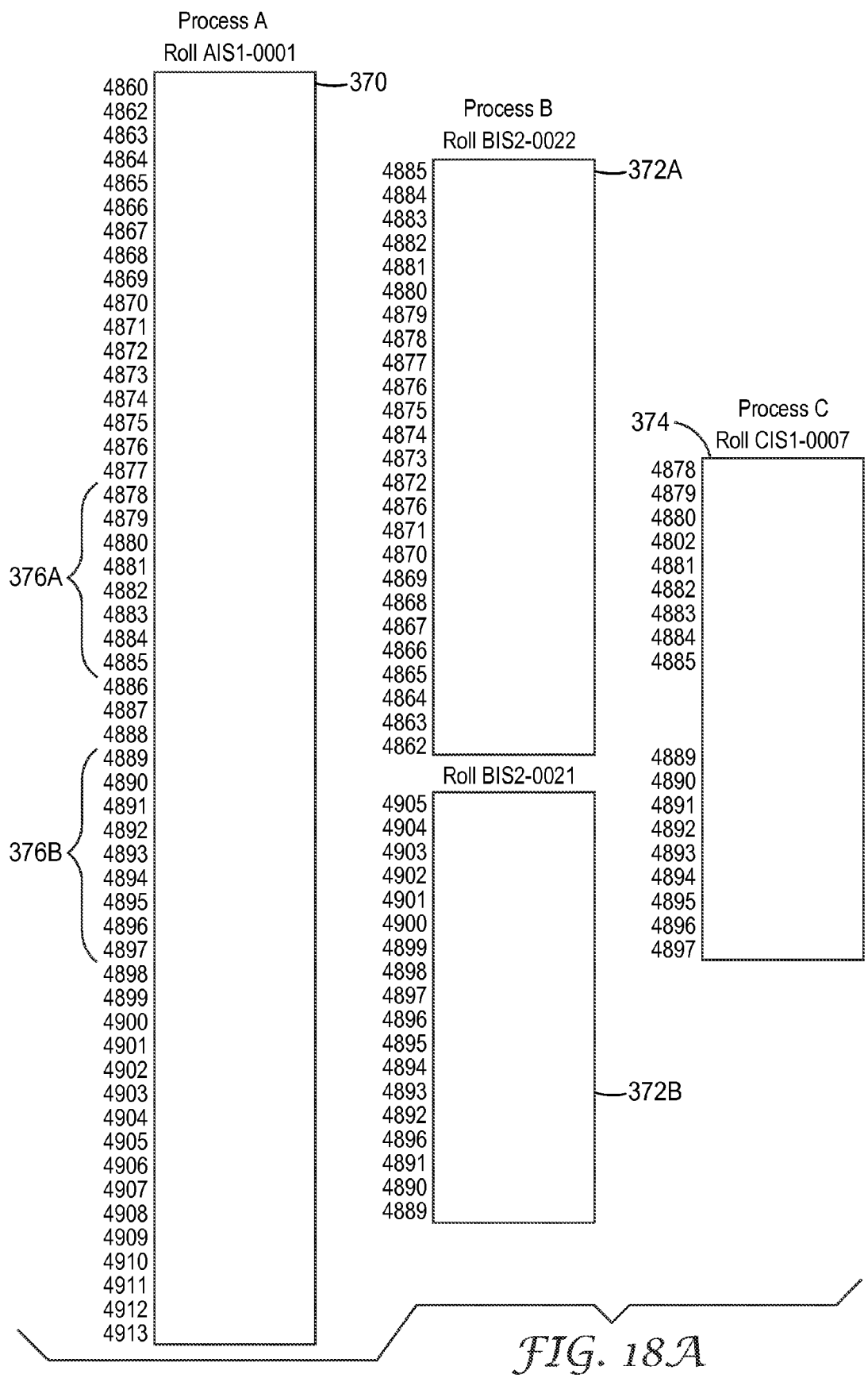
FIGS. 18A-18B are block diagrams illustrating example web segments with overlapping fiducial marks.

FIG. 18A is a block diagram illustrating an example web roll in various stages of manufacturing, wherein the web roll has been split and joined in subsequent processes. Initially, a manufacturing process, i.e. Process A, has processed web roll 370. In a subsequent process, web roll 370 has been split into two web roll segments 372A, 372B, each of which have been processed by a different process, i.e. Process B. Later, web roll segments 372A, 372B have been joined with another web roll segment to form web roll segment 374 which a third process, i.e. Process C, has manufactured. During each process in the evolution of the web roll, certain fiducial marks 376A, 376B identify a segment of the web roll that has undergone the same sequence of manufacturing. In this example, there are two segments of web that have undergone the same sequence of manufacturing: segment 376A, comprising fiducial marks 4878 to 4885, and segment 376B, comprising fiducial marks 4889 to 4897.

Figure 18B:
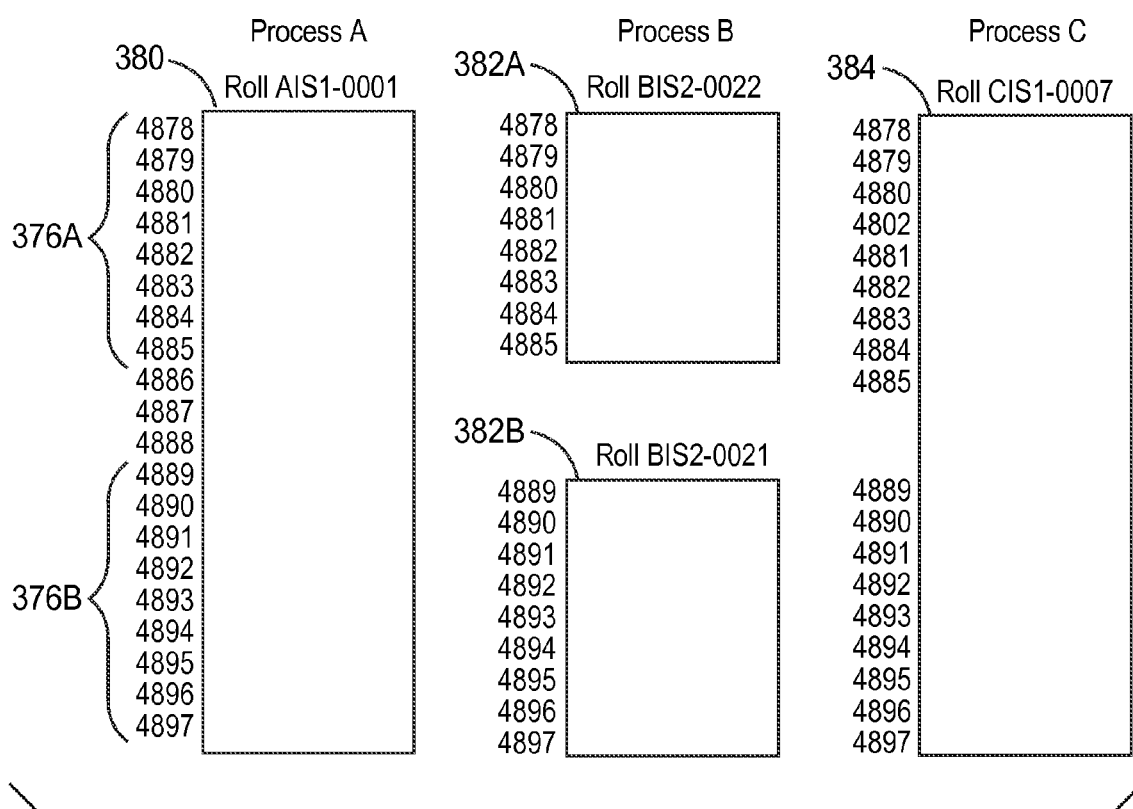

FIG. 18B is a block diagram showing exemplary segments 376A, 376B of FIG. 18A. FIG. 18B depicts how conversion control system 4 may realign the segments to analyze the data from each segment. Each of segments 376A, 376B have passed through the same series of manufacturing processes, i.e. Process A, Process B, and Process C. Conversion control system 4 may use the methods discussed with respect to FIGS. 16 and 17 to determine segments 376A, 376B and to align the segments so that conversion control system 4 may extract data regarding these segments from the pool of data from the processes that may have operated on segments 376A and 376B. Conversion control system 4 may then extract data common to segments 376A, 376B to mark positions of anomalies or defects on the surface of the web as described in detail in co-pending application Floeder et al., U.S. App. No. 2005/0232475, Apparatus and Method for the Automated Marking of Defects on Webs of Material (filed Apr. 19, 2004, published 2005), which is incorporated by reference in its entirety. Conversion control system 4 may use the data in other ways as well, for example, to optimize the processes or to repair or perform maintenance on the processes to reduce the number of anomalies and/or defects occurring in the web as a result of the processes.

Figure 19:
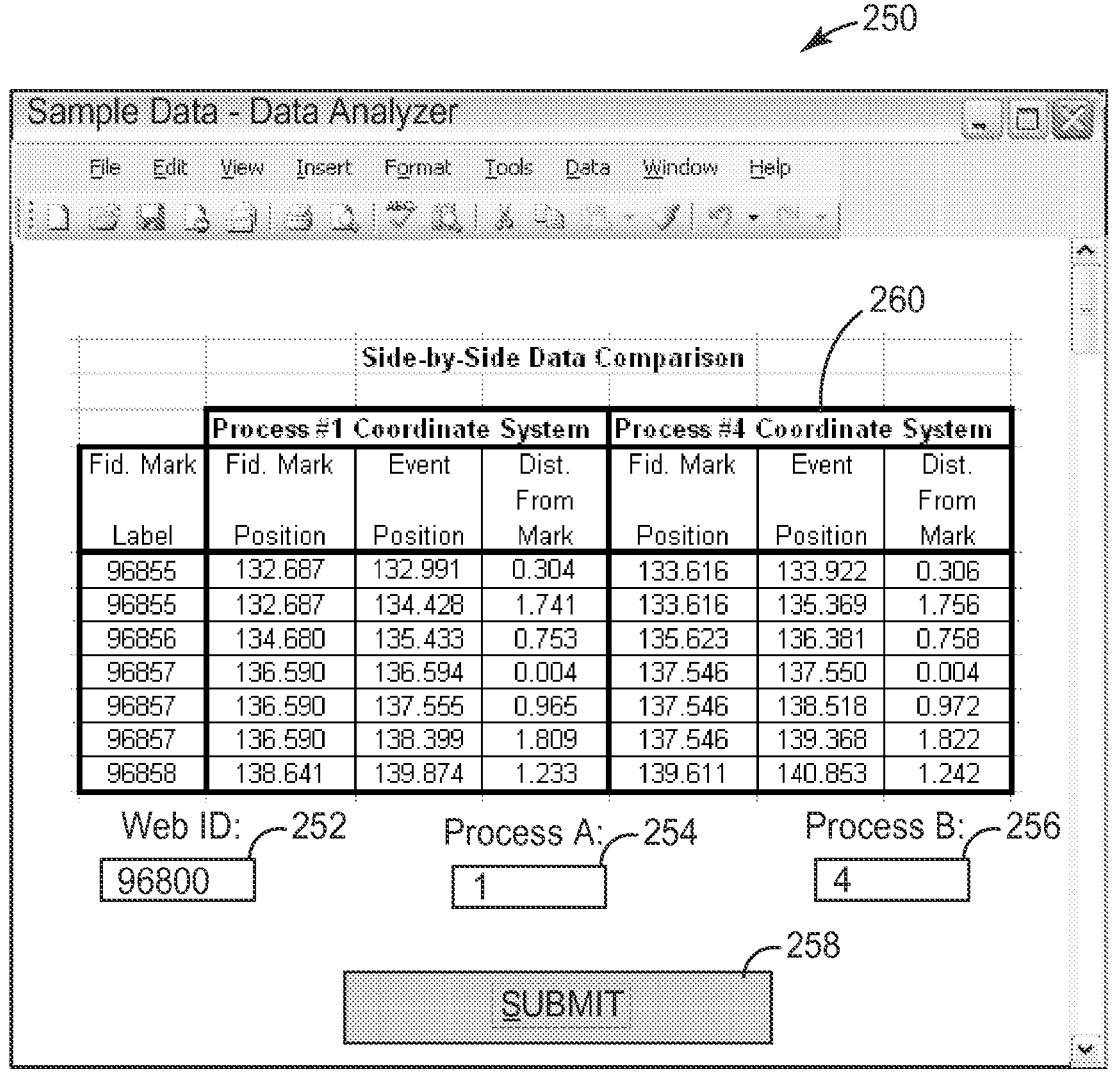
FIG. 19 is a screenshot illustrating a comparison of data gathered from two process lines.

FIG. 19 is a screenshot illustrating a comparison of data gathered from two process lines, for instance, process lines 74A and 74B. In one embodiment, conversion control system 4 comprises a graphical user interface system allowing a user to interact with conversion control system 4. As an example, the graphical user interface may allow a user to observe and compare data collected from a roll from multiple processes. FIG. 19 depicts graphical user interface ("GUI") 250. GUI 250 comprises web ID text box 252, process A text box 254, process B text box 256, submit button 258, and result pane 260.

Conversion control system 4 may present GUI 250 to a user upon a user request to compare data from process lines 74. A user may wish to view this data to optimize a particular process line, for instance, process line 74A. Once conversion control system 4 has received a request to show comparison data, conversion control system 4 will present the user with GUI 250. A user may then enter the numerical identification ("ID") of a particular web roll 10 in web ID text box 252. In one embodiment, web rolls might only be identified by fiducial marks; in that case, web ID text box 252 may be modified by those skilled in the art to retrieve data associated with a particular fiducial mark or a range of fiducial marks. An ID for a web or a process may be numerical, alphabetical, or alphanumerical. In some embodiments, web ID text box 252 may comprise a drop-down text box or may provide a search function; for instance, a user may search for the ID of a particular web roll based on where the web was manufactured, what process lines the web underwent, what types of products 12 the web was eventually converted into, to which of converting sites 8 the web was delivered, or other properties of a web.

A user may also enter the ID of the desired process lines 74 to be compared in text boxes 254, 256. Likewise, in other embodiments text boxes 254, 256 may comprise drop-down boxes or provide search functionality to search for the ID of a particular process line based on which of manufacturing plants 6 the process line is located, whether the process line comprises a fiducial mark writer 181, what type of web (e.g. paper, woven, metal, film, etc.) the process line operates upon, or other features of a process line.

Once a user has entered the information in text boxes 252, 254, 256, the user may then select submit button 258. Submit button 258 triggers conversion control system 4 to retrieve data in text boxes 252, 254, 256. Conversion control system 4 then retrieves data regarding the desired processes with respect to the web ID in accordance with the information entered into text boxes 252, 254, 256. Conversion control system 4 then displays the requested and retrieved information in result pane 260. If an error occurs during retrieval, for example if conversion control system 4 has no information about any web with ID matching that of the requested web ID, conversion control system 4 may instead display an error message in result pane 260 informing the user as to the nature of the error, for example, "ERROR: Web ID not found." In other embodiments, error messages may appear in other forms, for example in a new window or text box.

In the example of FIG. 19, exemplary GUI 250 is shown in response to input by which a user has requested data regarding a web with ID "96800." In addition, the user has also requested to compare data collected from process lines "1" and "4". Having pressed submit button 260, conversion control system 4 has retrieved and displayed data about web "96800" from process lines "1" and "4" in result pane 260. Thus, the user is able to view and compare the data gathered from these process lines to make determinations about the web and possibly to make decisions about how the process lines could be altered to improve product yield and decrease defects.

Figure 20:
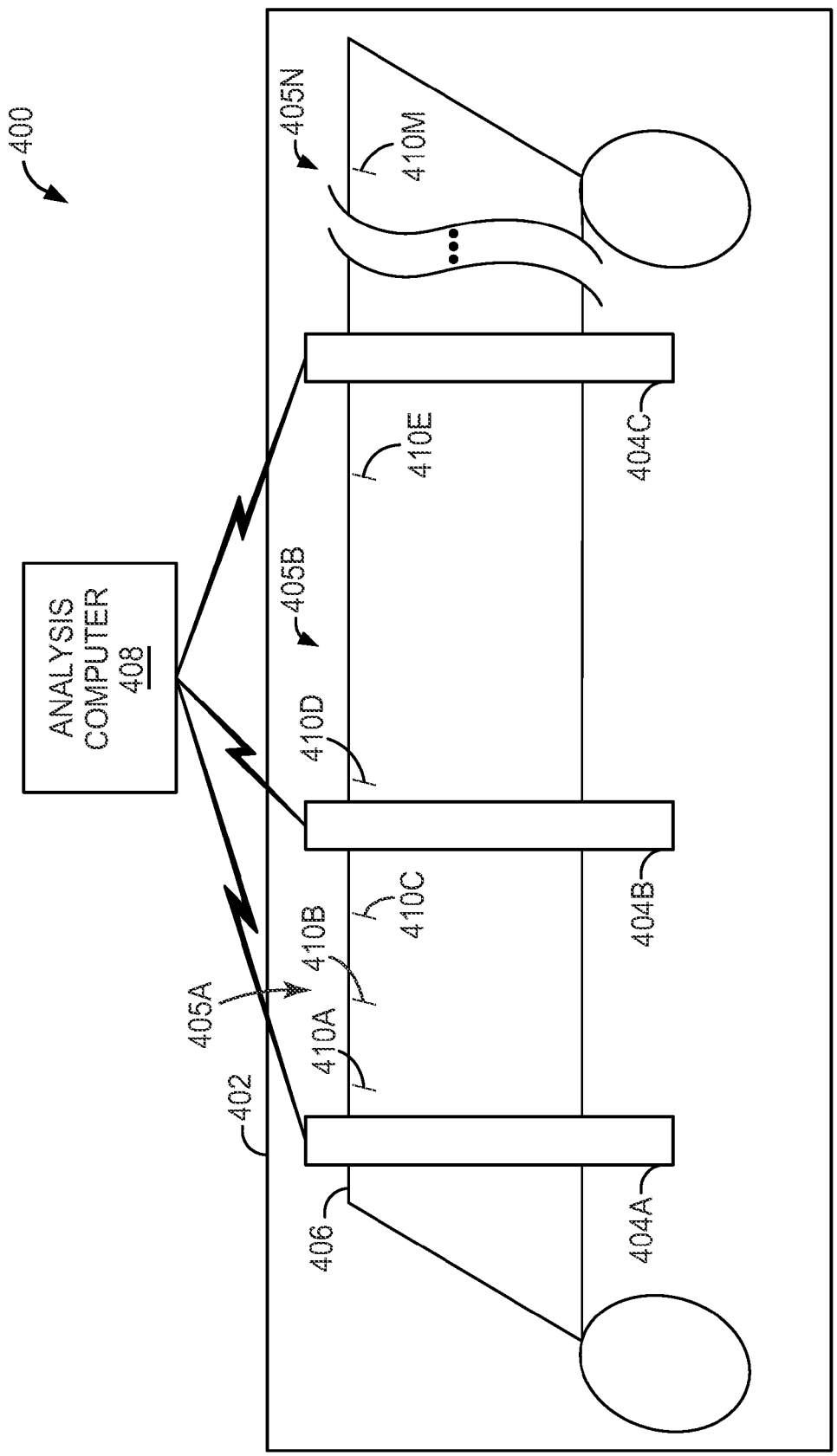
FIG. 20 is a block diagram that depicts an example of an alternative embodiment for applying techniques to spatially synchronize data, such as attribute or anomaly data.

FIG. 20 depicts an example of an alternative embodiment for applying techniques to spatially synchronize position data, such as position data for attributes or anomalies, for a plurality of different stages within a single process line. FIG. 20 depicts system 400 that includes a single process line 402 and analysis computer 408. Process line 402 includes multiple operations 404A-404N ("operations 404") performed within a plurality of distinct stages 405A-405N. As described below, various operations 404 may be applied within each of the different stages 405, and each of the stages may use different coordinate systems and/or fiducial marks in order to obtain position data. As a result, system 400 may logically be viewed as similar to a plurality of different processing lines for which position data may be spatially aligned in accordance with the techniques described herein. Some or all of operations 404 may gather digital information about web 406, which may correspond to a web roll 7. One of operations 404, e.g. operation 404A, may generate digital information according to a first coordinate system, while another one of operations 404, e.g. operation 404B, may generate digital information according to a second coordinate system. In some embodiments, certain operations 404 may only gather digital information without changing web 406. Analysis computer 408 may retrieve and store the data gathered from operations 404. One or more of operations 404 may change web 406 in such a way that analysis computer 408 must spatially synchronize the retrieved data.

As an example, web 406 may begin at operation 404A. Operation 404A may initially apply fiducial marks 410A-410M ("fiducial marks 410") to web 406 at two meter intervals. For example, fiducial marks 410A and 410B may be spaced approximately two meters apart. Once operation 404A has applied fiducial marks 410 to web 406, operation 404A may read each fiducial mark 410 and determine a position corresponding to each of fiducial marks 410. Operation 404A may record data regarding web 406 according to a first coordinate system. Operation 404A may include, for example, a computer to store the collected data according to the first coordinate system and to interface with analysis computer 408. In another embodiment, fiducial marks 410 may already be present on web 406 prior to the first operation, e.g., operation 404A.

Operation 404B may perform processing of web 406 that results in a change in the size, shape, or dimensions of web 406, for example, stretching web 406. As a result of this stretching, fiducial marks, e.g. fiducial marks 410D and 410E, may be spaced approximately six meters apart. In other words, operation 404A may stretch web 406 to, for example, three times the initial length of web 406. Operation 404B may read each fiducial mark 410 and again determine a corresponding position for each of fiducial marks 410. Operation 404B may record data, such as position data, anomaly data, defect data, and/or attribute data, according to a distinct coordinate system. Operation 404B may likewise include a computer to store the collected data according to the distinct coordinate system and to interface with analysis computer 408. Operation 404B may also insert new fiducial marks (not shown) between the fiducial marks applied by operation 404A in accordance with the method discussed, e.g., with respect to FIG. 15. Subsequent processes 404 may similarly process web 406, which may involve manipulating the size, shape, or other dimensions of web 406. Likewise, operations 404 may read fiducial marks 410 and record positions corresponding to fiducial marks 410, as well as data gathered during the operation, if any.

Once web 406 is finished, i.e. once operations 404 have finished processing web 406, analysis computer 408 may spatially synchronize data from operations 404. For example, analysis computer 408 may scale data gathered from operations 404 according to a method similar to the method discussed, e.g., with respect to FIG. 8A. In another embodiment, each of operations 404 subsequent to operation 404A may receive the coordinate system of operation 404A and record data according to the coordinate system 404A, similar to the method discussed, e.g. with respect to FIG. 8A.

Analysis computer 408 may create, for example, a conversion control plan according to the spatially synchronized data. Analysis computer 408 may analyze the spatially synchronized data to detect, for example, anomalies, defects, or attributes of web 406 in order to determine portions of web 406 to convert into various products. For example, a particular customer may require extremely narrow ranges of variation for one or more particular attributes for a particular product, while a different customer may accept a wider range of variation in the attributes. Analysis computer 408 may determine which portions of web 406 fall into the tightly controlled range of variation and determine that those portions of web 406 may be delivered to the first customer, while portions of web 406 that are within the wider range of variation may be delivered to the second customer.

Analysis computer 408 may determine whether anomalies exist in particular portions of web 406. Any of operations 404 may introduce anomalies, which may or may not cause defects, into web 406. Analysis computer 408 may search for anomalies and attempt to determine whether the detected anomalies will cause defects in particular products. Certain anomalies may cause a defect in one product while not necessarily causing a defect in a different product. Analysis computer 408 may use this information to determine which portions of web 406 should be used for creating which products.

Although described primarily with respect to generation and spatial registration of anomaly information (i.e., a deviation from normal product that may or may not be a defect, depending on its characteristics and severity), the techniques may be applied to defect information. That is, a system need not perform the intermediate functions of collecting anomaly information about potential defects and applying an algorithm to identify actual defects. Instead, the system may generate and spatially register defect data directly.

Moreover, although described with respect to imaging for anomaly/defect detection systems, any data gathering means may be used with the techniques as described herein. For example, data may be gathered using X-Rays, beta gauges, physical contact sensors, spectral gauges, capacitance gauges, interferometric sensors, haze measures, three-dimensional (3D) surface profilers, ultrasound, or digital imaging. The data gathered may be, for example, images of the web, thickness of the web, weight of the web, tension of the web, opacity of the web, surface roughness of the web, conductivity of the web, or pressure of the web.

Figure 21:
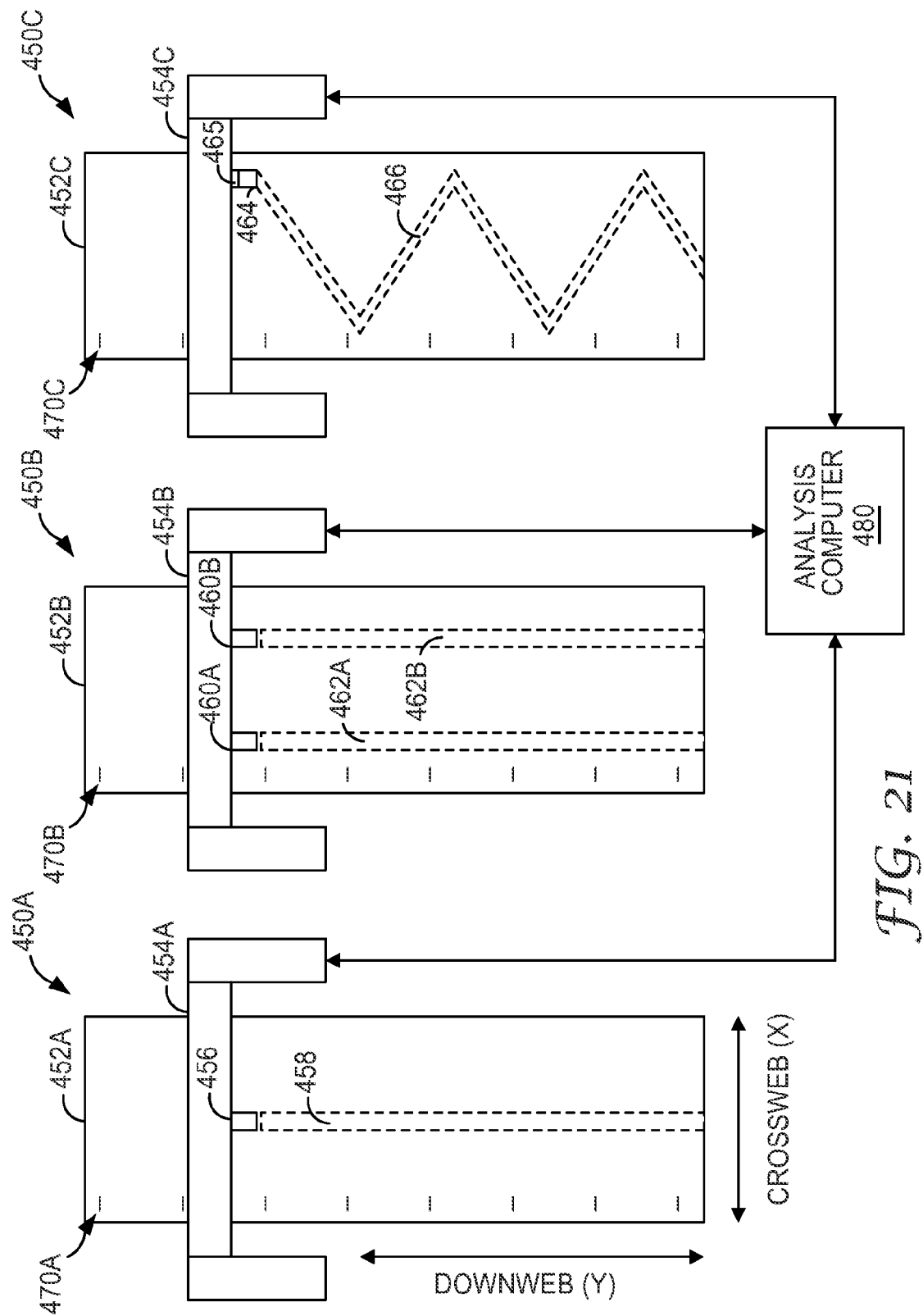
FIG. 21 is a block diagram illustrating an alternative embodiment of the techniques described herein as applied to a system for collecting measurement data from a web.

FIG. 21 is a block diagram illustrating an alternative embodiment of the techniques described herein as applied to a system for collecting measurement data from a web. Although discussed primarily with respect to spatial synchronization of anomaly information, the techniques described herein are not limited to the gathering of anomaly information. For example, the techniques described herein may be readily adapted to any form of gathering of data, such as process measurement data, for web manufacturing. Measurement systems often differ from inspection system previously described in that defects or anomalies are not typically segregated from the generated digital data stream, but rather, quantitative attribute information is acquired through either analog or digital data streams. Measurement systems also tend to collect data at lower data collection rates or lower spatial coverage of the web due to acquisition speed or spatial resolution limitations. However, the general mechanism is analogous to that used with inspection system data.

With measurement systems, product attribute data is acquired and spatially synchronized to the physical web using methods previously described. The techniques for spatially synchronizing data may be applied to any type of measured or determined attributes for a web, gathered using any type of data obtaining means. Examples of attribute data commonly acquired from a web for measurement systems include product thickness, surface roughness, temperature, pressure, reflectivity, transmission, transflection, three dimensional height, detailed surface structure measurements, spectral transmission or reflection, X-Ray images or readings, ultraviolet (UV) images or readings, infrared (IR) images or readings, optical or structural uniformity, pressure variations such as pressure drop, capacitance, haze, flatness, conductivity, color, birefringence, and polarization. Examples of measurement devices to measure such attributes of a web include radiation gauges, optical gauges, Beta gauges, X-Ray devices, UV or IR cameras or sensors, capacitance gauges, physical sensors, machine vision systems, temperature sensors, pressure sensors, and spectral cameras and sensors. One skilled in the art will appreciate that the techniques described herein may readily be applied to other measurements or measurement devices.

A measurement system may acquire information directly from a web, a web segment, a web-based product, or from the neighboring environment. In any case, a measurement system may associate the measurement data with a physical location on the web to a high degree of spatial accuracy. For example, a Beta gauge may provide thickness data for the product itself at regular intervals that are spatially synchronized for analysis across multiple processes. As opposed to the use of anomaly data, attribute data, e.g. thickness data, may describe an attribute, i.e. a characteristic or feature, of the web, rather than identifying defective or potentially defective regions of the web.

A measurement system may also, as another example, obtain data regarding the web indirectly. For example, a measurement system may acquire temperature data from an oven near the web, without necessarily directly measuring temperature of the web itself. However, the measurement system may associate data from this temperature sensor with physical locations of the web material as a product is manufactured from the web. That is, there may be a spatial synchronization between the web material and physical measurement data that can be associated between processes to a high degree of spatial accuracy. Temperature data, for example, may be particularly useful in processes such as annealing.

Measurement data is generally acquired for web processes in one of three exemplary manners. One type of measurement system involves a single point sensor acquiring data at a stationary point in the crossweb or transverse web direction. FIG. 21 illustrates an example of such a measurement system 450A. System 450A includes web 452A and operation 454A that includes stationary sensor 456. Web 452A includes fiducial marks 470A. Operation 454A may perform processing on web 452A and may gather data, such as measurement data, from web 452A and record a position for each unit of data. Operation 454A may also read fiducial marks 470A and record associated positions of each of fiducial marks 470A. Sensor 456 of operation 454A may obtain measurement data for a plurality of downweb, i.e. machine direction, positions, but limited resolution in the crossweb direction. As depicted in the example of FIG. 21, sensor 456 may obtain data for region 458 of web 452A. Operation 454A may also include a computer and/or database to store local attribute information and to interface with conversion computer 480.

A second method of obtaining measurement data involves the use of an array of sensors or measurement devices positioned at multiple locations crossweb. Measurement system 450B of FIG. 21 includes web 452B and operation 454B, which includes two stationary measurement devices 460A-460B ("measurement devices 460"). Other embodiments may use any number of measurement devices. Web 452B includes fiducial marks 470B. Operation 454B may perform processing on web 452B and may gather data, such as measurement data, from web 452B. Measurement devices 460 may obtain data for respective regions 462A-462B ("regions 462") of web 452B. Moreover, operation 454B may read and record position information for each of fiducial marks 470B. This method may provide for arbitrarily high crossweb and downweb spatial resolution of measurement data at the expense of multiple sensors. Operation 454B may also include a computer and/or database to store local attribute information and to interface with conversion computer 480.

A third method of obtaining measurement data involves the use of a single sensor that is capable of moving in the crossweb direction. Measurement system 450C of FIG. 21 includes web 452C and operation 454C, which includes sensor 464. Web 452C includes fiducial marks 470C. Operation 454C may perform processing on web 452C and may gather data measurement data from web 452C. Sensor 464 of operation 454C may include a traversing mechanism, e.g. actuator 465, that enables sensor 464 to traverse operation 454C in the crossweb direction. Actuator 465 may be a motor on a track of operation 454C, a sliding assembly, a fixed attachment to a moving cable, or any other means for enabling sensor 464 to traverse the web in the crossweb direction. Sensor 464 may obtain measurement data in the crossweb direction while web 452C moves in the downweb direction which results in a zigzag pattern of data acquisition, i.e. region 466 of web 452C. Likewise, operation 454C may read and record position information for each of fiducial marks 470C. Operation 454B may also include a computer and/or database to store local attribute information and to interface with conversion computer 480.

Each of operations 454 may be coupled to a remote data storage facility, such as conversion computer 480 as shown in FIG. 21. Conversion computer 480 may retrieve data from each of operations 454 and spatially synchronize the data in order to produce a composite map. The composite map may be used to create a conversion control plan for creating products for various customers from a web. For example, a first customer may require very strict quality control while a second customer may not need products conforming to standards that are so strict. Conversion computer 480 may analyze the data from operations 454 to determine which portions of the final web conform to the strict standard and designate products from those portions for the first customer, while products from other portions of the web may be designated for the second customer.

Figure 22:
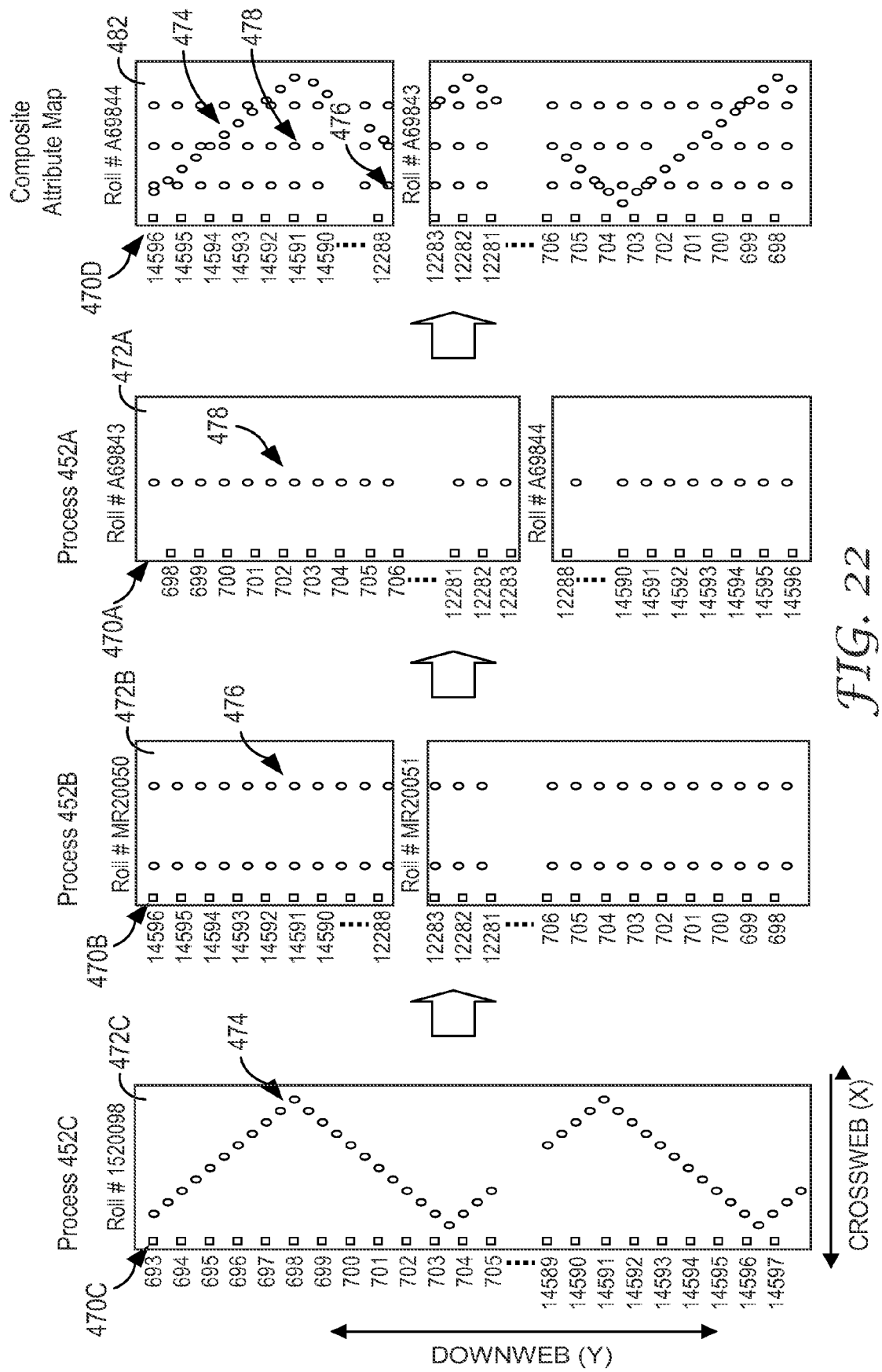
FIG. 22 is a graphical representation of measurement data gathered from various processing and/or measuring operations.

FIG. 22 is a graphical representation of data gathered from operations 454 of FIG. 21. For most data acquisition methods, such as those portrayed in FIG. 21 or other data acquisition methods, each data point conceptually includes a physical X or crossweb position, a Y or downweb position, and a measurement data value. FIG. 22 illustrates examples of each of the measurement values spatially synchronized to the web product through the use of fiducial marks. That is, conversion computer 480 of FIG. 21 spatially synchronizes the measurement values from processes 454. Conversion computer 480 may spatially synchronize the data according to, for example, the method discussed with respect to FIG. 12.

Conversion computer 480 may also generate composite attribute map 482 as a combination of the measurement or inspection data from processes 454. For example, each of processes 454 may perform processing, obtain measurement data, and/or obtain inspection data from a common web segment, e.g. the web segment defined by fiducial marks "698" to "14596" shown in FIG. 22. This web segment may first undergo processing at operation 454C, then proceed to operation 454B, then operation 454A. Operation 454C may generate data 474, corresponding to region 466, using sensor 464. Operation 454B may generate data 476, corresponding to regions 462, using sensors 460. Operation 454A may generate data 478, corresponding to region 458, using sensor 456.

Conversion computer 480 may obtain data (e.g., data 474, 476, 478) from each of operations 454 and spatially synchronize the data using fiducial marks 470D. Fiducial marks 470D may either be registered according to globally unique position information, as discussed with respect to FIG. 8B, or may be position-adjusted to a coordinate system of one of operations 454, as discussed with respect to FIG. 8A. Analysis computer may also adjust positional information regarding the collected data based on the direction of the web to generate composite attribute map 482. Conversion computer 480 may generate composite map 482 so as to include each of data 474, 476, and 478 from processes 454, as shown in FIG. 22. Conversion computer 480 may use composite attribute map 482 to grade or sort the web material quality at any physical location of the web. Composite attribute map 482 can also be used to selectively sort material with specifically desired attributes that are most desired by particular customers.

Various embodiments of the invention have been described. These and other embodiments are within the scope of the following claims.

The invention claimed is:

1. A method comprising:
performing a plurality of operations on a web at a plurality of manufacturing process lines;
imaging a sequential portion of the web to provide digital information at each of the manufacturing process lines;
processing the digital information to produce local anomaly information for each of the manufacturing process lines, wherein the local anomaly information for each of the manufacturing process lines includes position data for a set of regions on the web containing anomalies;
registering the position data of the local anomaly information for the plurality of manufacturing process lines to produce aggregate anomaly information;
analyzing at least a portion of the aggregate anomaly information to determine which of the anomalies represent actual defects in the web; and
outputting a conversion control plan.

2. The method of claim 1, wherein registering the position data includes translating the position data of the local anomaly information for one of the manufacturing process lines into a coordinate system associated with the different one of the manufacturing process to produce the aggregate anomaly information.

3. The method of claim 1, wherein registering the position data includes translating the position data for the local anomaly information for each of the manufacturing process lines into a common coordinate system.

4. The method of claim 1, wherein registering the position data comprises creating a correspondence within a specified tolerance between the position data gathered from a plurality of the manufacturing lines regarding a segment of the web on which each of the manufacturing lines have performed processing.

5. The method of claim 1, wherein registering the position data comprises associating data generated by the different manufacturing lines for substantially the same physical locations on the web within an acceptable tolerance.

6. The method of claim 1,
wherein processing the digital information comprises:
  (i) when performing one or more operations on the web at a first one of the manufacturing process lines, generating first local anomaly information to include position data for the anomalies detected from the digital information associated with the first manufacturing process to locate the anomalies within a first coordinate system, and
  (ii) when performing one or more operations on the web at a second one of the manufacturing process lines, generating second local anomaly information to include position data for the anomalies detected from the digital information associated with the first manufacturing process to locate the anomalies within a second coordinate system, and
wherein registering the position data includes translating the position data for the second local anomaly information to reposition the anomalies from the second coordinate system to locations within the first coordinate system.

7. The method of claim 1, wherein performing a plurality of operations on a web at a plurality of manufacturing process lines comprises:
  performing a first set of operations on the web at a first manufacturing process line;
  reloading the web on the first manufacturing process line; and
  performing a second set of operations on the web at the first manufacturing process line.

8. The method of claim 1, wherein the plurality of manufacturing process lines comprises a single manufacturing process line that has been reloaded with the same web two or more times.

9. The method of claim 1, further comprising, after completion of a first one of the manufacturing process lines, shipping the web from a first manufacturing plant containing the first manufacturing process line to a second manufacturing plant containing a second one of the manufacturing process lines.

10. The method of claim 1, wherein the position data registration is performed after completion of all of the manufacturing process lines have applied the operations to the web and prior to the conversion of the web to the products.

11. The method of claim 1, further comprising communicating the local anomaly information from the manufacturing process lines to a central server for registration of the position data.

12. The method of claim 1, further comprising:
  communicating first local anomaly information from an analysis server within a first manufacturing plant to a conversion control system external to the first manufacturing plant;
  communicating the second local anomaly information from an analysis server within a second manufacturing plant to a conversion control system external to the first manufacturing plant;
  registering the first and second local anomaly information with the conversion control system;
  generating, with the conversion control system, a conversion plan for the web based on the actual defects determined from the aggregate anomaly information; and
  communicating the conversion control plan from the conversion control system to one or more conversion plants for converting the web in accordance with the generated conversion plan.

13. The method of claim 1, further comprising forming, from the aggregate anomaly information, a composite defect map having defects corresponding to at least a portion of the anomalies from a first one of the manufacturing process lines and at least a portion of the anomalies from a second one of the first manufacturing process lines.

14. The method of claim 1, wherein the plurality of manufacturing process lines apply different coordinate systems when imaging the web.

15. The method of claim 1, wherein the plurality of manufacturing process lines apply the same coordinate system when imaging the web.

16. The method of claim 1, further comprising:
  applying a set of fiducial marks to the web;
  recording a position for each of the fiducial marks when applied to the web;
  after applying the fiducial marks, detecting positions of the fiducial marks at one of the manufacturing process lines; and
  determining, based on the detected positions of the fiducial marks, the position data for the local anomaly information produced at the subsequent manufacturing processes lines.

17. The method of claim 16, wherein registering the local anomaly information comprises translating the position data for the anomalies of the local anomaly information based on the recorded position data of the fiducial marks.

18. The method of claim 17, further comprising:
  measuring locations of the fiducial marks at a first one of the manufacturing process lines;
  measuring locations of the fiducial marks at a second one of the manufacturing process lines;
  calculating one or more offsets based on differences between the measured locations for the fiducial marks at the first one of the manufacturing process lines and the measured locations for the second one of the manufacturing process lines; and
  applying the offsets to the position data to register the local anomaly information.

19. The method of claim 18, wherein calculating one or more offsets comprises, for each of the manufacturing process lines, calculating an offset for each segment of the web between two adjacent fiducial marks.

20. The method of claim 19, wherein calculating one or more offsets comprises applying a linear transformation to the position data for each of the anomalies, wherein the linear transformation includes a scaling factor calculated based on a ratio of: (1) a distance between at least two of the fiducial marks within the first one of the manufacturing process, and (2) a distance between the at least two of the fiducial marks determined within the second one of the manufacturing process.

21. The method of claim 18, wherein calculating one or more offsets comprises applying a nonlinear transformation to the position data for each of the anomalies, wherein the nonlinear transformation is calculated using previously generated mathematical models of the web process.

22. The method of claim 16, wherein applying a set of fiducial marks comprises specifying, within one or more of the fiducial marks, an identifier for the manufacturing process line within which the fiducial marks were applied.

23. The method of claim 22, wherein registering the position data comprises:
reading the fiducial marks to identify the manufacturing process line within which the fiducial marks were applied;
determining a coordinate system for the manufacturing process line within which the fiducial marks were applied;
determining a formula to translate from the coordinate system for the a formula to translate the position data to a target coordinate system; and
applying the formula to the position data.

24. The method of claim 16, wherein each of the fiducial marks include a plurality of bar codes, each of the plurality of bar codes conforming to the interleaved 2 of 5 symbology.

25. The method of claim 16, wherein one or more of the fiducial marks includes a first field for uniquely identifying one of a plurality of manufacturing plants, and a second field for uniquely identifying each of a plurality of manufacturing process lines associated with the plant.

26. The method of claim 16, further comprising, for each of the manufacturing process lines:
determining whether each of the fiducial marks is absent from the web; and
printing a replacement fiducial mark on the on the web for any absent fiducial mark.

27. The method of claim 16, further comprising printing an additional fiducial mark between two sequential fiducial marks upon determining that the two sequential fiducial marks are present on the web.

28. The method of claim 1,
wherein a subset of the anomalies detectable from an inspection system for a first one of the manufacturing process lines is hidden from at least one inspection system associated with a subsequent one of the manufacturing process lines, and
wherein registering the position data includes producing aggregate anomaly information to include data specifying the hidden anomalies.

29. The method of claim 28, wherein registering the position data comprises generating, from the aggregate anomaly information, a composite map that specifies the anomalies detected at each of the plurality of manufacturing process lines.

30. The method of claim 1,
wherein a subset of the anomalies detectable from an inspection system for a first one of the manufacturing process lines is corrected by a subsequent manufacturing process as determined by at least one inspection system associated with the subsequent manufacturing operation, and
wherein registering the position data includes producing aggregate anomaly information to adjust inspection system sensitivity for the first manufacturing process operation.

31. The method of claim 1, further comprising
analyzing at least a portion of the aggregate anomaly information to determine which of the anomalies represent actual defects in the web for a plurality of different products;
determining a value of at least one product selection parameter for each of the products;
selecting at least one of the products based on the determined value for each of the products; and
adding the selected product to the conversion control plan corresponding to the analyzed portion of aggregate anomaly information.

32. The method of claim 1, further comprising converting the web into the one or more product or products.

33. The method of claim 1, wherein registering comprises registering to a high degree of accuracy when a physical location of an anomaly on the web represented within the position data for one of the manufacturing process lines is within +−2 mm of the same physical location on the web within the position data for a second one of the manufacturing process lines.

34. The method of claim 1, wherein registering comprises registering to a standard degree of accuracy when a physical location of an anomaly on the web represented within the position data for one of the manufacturing process lines is within +−5 mm of the same physical location on the web within the position data for a second one of the manufacturing process lines.

35. The method of claim 1, wherein when a physical location of an anomaly on the web represented within the position data for one of the manufacturing process lines is greater than 150 mm of the same physical location on the web within the position data for a second one of the manufacturing process lines, the physical location of the anomaly is a failed registration.

36. The method of claim 1, wherein registering comprises:
identifying a set of fiducial marks forming a segment of the web upon which a first one of the manufacturing process lines has performed an operation;
determining whether a second one of the manufacturing process lines has performed an operation on the segment or a sub-segment of the segment; and
extracting data from each of the first manufacturing process and the second manufacturing process corresponding to the segment or the sub-segment upon which both the first manufacturing process and the second manufacturing process have performed operations; and
aligning the extracted data.

37. The method of claim 35,
wherein determining whether the second one of the manufacturing process lines has performed an operation comprises:
creating a tree data structure according to a process association map describing interactions between the first manufacturing process line and the second manufacturing process line;
determining whether the second manufacturing process line is a possible predecessor process to the first manufacturing process line according to the tree data structure; and
wherein extracting data comprises searching for and extracting data from the second manufacturing process line corresponding to the segment of the web only when the second manufacturing process line is a possible predecessor process to the first manufacturing process line.

38. A system comprising:
a plurality of manufacturing process lines that perform a plurality of operations on a web;
a plurality of imaging devices positioned within a plurality of manufacturing process lines, wherein each of the imaging devices sequentially images at least a portion of the web to provide digital information;
one or more analysis computers to process the digital information to produce local anomaly information for each of the manufacturing process lines, wherein the local anomaly information for each of the manufacturing processes includes position data for a set of regions on the web containing anomalies;
a computer that registers the position data of the local anomaly information for the plurality of manufacturing process lines to produce aggregate anomaly information; and
a conversion control system that analyzes at least a portion of the aggregate anomaly information to determine which anomalies represent actual defects in the web for a plurality of different products.

39. The system of claim 38, wherein the computer that registers the position data is a component of the conversion control system.

40. The system of claim 38, wherein the computer that registers the position data also operates as one of the analysis computers.

41. The system of claim 38, wherein the plurality of manufacturing process lines and the analysis computers are located within a plurality of manufacturing plants, 42. The system of claim 41, further including a consolidation server located within each of the manufacturing plants and configured to collect data from each analysis computer of the respective manufacturing plant and transmit the local anomaly information to the conversion control system.

43. The system of claim 42, wherein the conversion control system executes software to collect the local anomaly information from each of consolidation servers and register all of the local anomaly information to form a composite map.

44. The system of claim 38, wherein the conversion control system determines a value of at least one product selection parameter for each of the products, and selects one of the products for conversion of the web based on the determined value for each of the products.

45. A conversion control system comprising:
a database storing data defining a set of rules;
an interface to receive local anomaly information from a plurality of different analysis machines associated with a plurality of manufacturing process lines that perform a plurality of operations on a web of material, wherein each of the manufacturing process lines includes position data for a set of regions on the web containing anomalies;
a computer that registers the position data of the local anomaly information for the plurality of manufacturing process lines to produce aggregate anomaly information;
a conversion control engine that applies the rules to the aggregate anomaly information to determine which anomalies represent actual defects in the web for a plurality of different products.

46. The conversion control system of claim 45, wherein the conversion control engine applies the rules to determine a value for at least one product selection parameter for each of a plurality of products, wherein the conversion control engine selects one of the products for conversion of the web based on the determined values.

* * * * *